United States Patent
Yasuda et al.

(10) Patent No.: US 12,122,768 B2
(45) Date of Patent: Oct. 22, 2024

(54) BENZONITRILE DERIVATIVE, LIGHT-EMITTING MATERIAL, AND LIGHT-EMITTING ELEMENT USING SAME

(71) Applicants: KYUSHU UNIVERSITY, NATIONAL UNIVERSITY CORPORATION, Fukuoka (JP); NIPPON SODA CO., LTD., Tokyo (JP)

(72) Inventors: Takuma Yasuda, Fukuoka (JP); In Seob Park, Fukuoka (JP); Katsunori Tanaka, Odawara (JP); Yasuhiro Miyashita, Odawara (JP); Yasuhiko Ashikari, Odawara (JP)

(73) Assignees: KYUSHU UNIVERSITY, NATIONAL UNIVERSITY CORPORATION, Fukuoka (JP); NIPPON SODA CO., LTD., Tokyo (JP)

( * ) Notice: Subject to any disclaimer, the term of this patent is extended or adjusted under 35 U.S.C. 154(b) by 825 days.

(21) Appl. No.: 17/272,550

(22) PCT Filed: Aug. 29, 2019

(86) PCT No.: PCT/JP2019/033913
§ 371 (c)(1),
(2) Date: Mar. 1, 2021

(87) PCT Pub. No.: WO2020/050127
PCT Pub. Date: Mar. 12, 2020

(65) Prior Publication Data
US 2021/0332032 A1    Oct. 28, 2021

(30) Foreign Application Priority Data

Sep. 5, 2018  (JP) .................. 2018-165955
Feb. 1, 2019  (JP) .................. 2019-017156

(51) Int. Cl.
C07D 403/14   (2006.01)
H10K 50/11    (2023.01)
H10K 85/60    (2023.01)

(52) U.S. Cl.
CPC ......... *C07D 403/14* (2013.01); *H10K 85/654* (2023.02); *H10K 85/6572* (2023.02); *H10K 50/11* (2023.02)

(58) Field of Classification Search
CPC .............. H01K 85/654; C07D 403/14
See application file for complete search history.

(56) References Cited

U.S. PATENT DOCUMENTS

| | | | | |
|---|---|---|---|---|
| 2009/0072727 A1* | 3/2009 | Takeda | ............ | H10K 85/654 313/504 |
| 2015/0105564 A1* | 4/2015 | Adachi | ............ | C07D 209/08 548/440 |
| 2016/0126478 A1* | 5/2016 | Zheng | ............ | C09K 11/06 548/440 |
| 2016/0380205 A1* | 12/2016 | Adachi | ............ | H10K 85/631 544/102 |
| 2018/0108857 A1* | 4/2018 | Adachi | ............ | H10K 50/15 |
| 2018/0175294 A1* | 6/2018 | Duan | ............ | H10K 85/6572 |
| 2019/0013481 A1 | 1/2019 | Nasu et al. | | |
| 2019/0016704 A1* | 1/2019 | Nasu | ............ | C07D 403/10 |
| 2019/0058130 A1* | 2/2019 | Aguilera-Iparraguirre | ............ | H10K 85/654 |
| 2019/0062312 A1* | 2/2019 | Zink | ............ | C07D 403/14 |
| 2019/0194131 A1 | 6/2019 | Yokoyama et al. | | |
| 2019/0241549 A1* | 8/2019 | Yang | ............ | C07D 491/048 |
| 2020/0083460 A1* | 3/2020 | Duan | ............ | H10K 85/322 |
| 2020/0119287 A1* | 4/2020 | Aguilera-Iparraguirre | ............ | C09K 11/06 |
| 2020/0235313 A1* | 7/2020 | Nakanotani | ............ | C09K 11/06 |
| 2021/0202864 A1* | 7/2021 | Nakanotani | ............ | H10K 85/636 |

(Continued)

FOREIGN PATENT DOCUMENTS

| | | | | |
|---|---|---|---|---|
| CN | 106316924 A | * | 1/2017 | ............ C07D 209/82 |
| JP | 2016-526025 A | | 9/2016 | |
| JP | 2016-539182 A | | 12/2016 | |

(Continued)

OTHER PUBLICATIONS

Machine translation of CN 106316924, 2023 (Year: 2023).*
Nov. 19, 2019 International Search Report issued in International Patent Application No. PCT/JP2019/033913.

*Primary Examiner* — Liam J Heincer
(74) *Attorney, Agent, or Firm* — Oliff PLC

(57) ABSTRACT

A compound represented by formula (I).

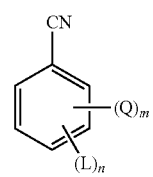

(I)

In formula (I), each L independently represents a substituted or unsubstituted aryl group, or a substituted or unsubstituted heteroaryl group, n indicates the number of L groups, and is either 1 or 2, each Q independently represents a substituted or unsubstituted 3,6-di-t-butyl-9H-carbazol-9-yl group, a substituted or unsubstituted 3,6-diphenyl-9H-carbazol-9-yl group, or a substituted or unsubstituted 3-phenyl-6-t-butyl-9H-carbazol-9-yl group, and m indicates the number of Q groups, and has a value of 5−n.

5 Claims, 10 Drawing Sheets

(56) References Cited

U.S. PATENT DOCUMENTS

2021/0359217 A1\* 11/2021 Yoshida ............... C07D 401/14
2022/0242822 A1\* 8/2022 Yasuda .............. H10K 85/6572

FOREIGN PATENT DOCUMENTS

| JP | 2018-519663 | A | 7/2018 |
|----|----|----|----|
| WO | 2014/183080 | A1 | 11/2014 |
| WO | 2015/066354 | A1 | 5/2015 |
| WO | 2016/138077 | A1 | 9/2016 |
| WO | 2016/152605 | A1 | 9/2016 |
| WO | 2017/115834 | A1 | 7/2017 |
| WO | 2018/047948 | A1 | 3/2018 |
| WO | 2018/155642 | A1 | 8/2018 |
| WO | 2018/237389 | A1 | 12/2018 |

\* cited by examiner

BENZONITRILE DERIVATIVE, LIGHT-EMITTING MATERIAL, AND LIGHT-EMITTING ELEMENT USING SAME

TECHNICAL FIELD

The present invention relates to a 2,3,4,5,6-pentasubstituted benzonitrile compound that exhibits excellent light emission characteristics, a light-emitting material, and a light-emitting element using the same.

Priority is claimed on Japanese Patent Application No. 2018-165955, filed Sep. 5, 2018, and Japanese Patent Application No. 2019-017156, filed Feb. 1, 2019, the contents of which are incorporated herein by reference.

BACKGROUND ART

It is known that certain types of carbazol-9-yl-substituted benzonitrile compounds can be used as light-emitting materials.

For example, Patent Document 1 discloses compounds such as 3,5-di(3,6-diphenyl-9H-carbazol-9-yl)-2,4,6-tri(4-cyanophenyl)-benzonitrile. Patent Document 2 discloses compounds such as 2,3,5,6-tetra(3,6-diphenyl-9H-carbazol-9-yl)-4-(4-cyanophenyl)-benzonitrile. Patent Document 3 discloses compounds such as 2,3,5,6-tetra(9H-carbazol-9-yl)-4-phenyl-benzonitrile.

PRIOR ART LITERATURE

Patent Documents

Patent Document 1: Japanese Translation of PCT International Application, Publication No. 2016-539182
Patent Document 2: International Patent Publication No. WO2016/138077A
Patent Document 3: International Patent Publication No. WO2014/183080A

SUMMARY OF INVENTION

Problems to be Solved by the Invention

Objects of the present invention are to provide a 2,3,4,5,6-pentasubstituted benzonitrile compound (hereafter sometimes referred to as "the compound of the present invention") that exhibits excellent light emission characteristics, a light-emitting material, and a light-emitting element using the same.

Means for Solving the Problems

In order to achieve the above objects, the present invention including the following aspects was completed.
[1] A compound represented by formula (I).

[Chemical formula 1]

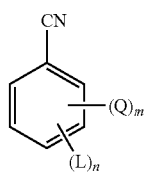

(I)

In formula (I),
each L independently represents a substituted or unsubstituted aryl group, or a substituted or unsubstituted heteroaryl group,
n indicates the number of L groups, and is either 1 or 2,
each Q independently represents a substituted or unsubstituted 3,6-di-t-butyl-9H-carbazol-9-yl group, a substituted or unsubstituted 3,6-diphenyl-9H-carbazol-9-yl group, or a substituted or unsubstituted 3-phenyl-6-t-butyl-9H-carbazol-9-yl group, and
m indicates the number of Q groups, and has a value of 5−n.
[2] The compound according to [1] above, represented by formula (IIa).

[Chemical formula 2]

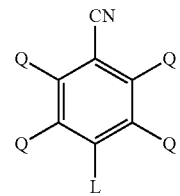

(IIa)

In formula (IIa), L represents a substituted or unsubstituted aryl group, or a substituted or unsubstituted heteroaryl group, and each Q independently represents a substituted or unsubstituted 3,6-di-t-butyl-9H-carbazol-9-yl group.
[3] The compound according to [1] above, represented by formula (IIb).

[Chemical formula 3]

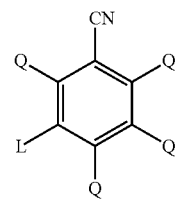

(IIb)

In formula (IIb), L represents a substituted or unsubstituted aryl group, or a substituted or unsubstituted heteroaryl group, and each Q independently represents a substituted or unsubstituted 3,6-di-t-butyl-9H-carbazol-9-yl group.
[4] The compound according to [1] above, represented by formula (IIc).

[Chemical formula 4]

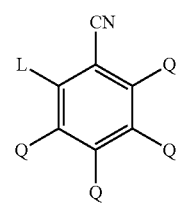

(IIc)

In formula (IIc), L represents a substituted or unsubstituted aryl group, or a substituted or unsubstituted heteroaryl group, and each Q independently represents a substituted or unsubstituted 3,6-di-t-butyl-9H-carbazol-9-yl group.

[5] The compound according to [1] above, represented by formula (IIIa).

[Chemical formula 5]

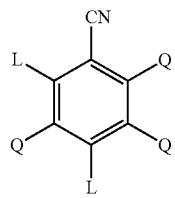

(IIIa)

In formula (IIIa), each L independently represents a substituted or unsubstituted aryl group, or a substituted or unsubstituted heteroaryl group, and each Q independently represents a substituted or unsubstituted 3,6-di-t-butyl-9H-carbazol-9-yl group, or a substituted or unsubstituted 3,6-diphenyl-9H-carbazol-9-yl group.

[6] The compound according to [1] above, represented by formula (IIIb).

[Chemical formula 6]

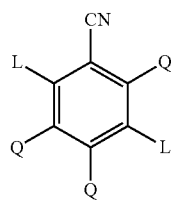

(IIIb)

In formula (IIIb), each L independently represents a substituted or unsubstituted aryl group, or a substituted or unsubstituted heteroaryl group, and each Q independently represents a substituted or unsubstituted 3,6-di-t-butyl-9H-carbazol-9-yl group, or a substituted or unsubstituted 3,6-diphenyl-9H-carbazol-9-yl group.

[7] The compound according to [1] above, represented by formula (IIIc).

[Chemical formula 7]

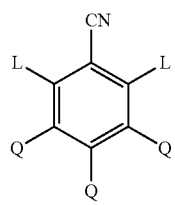

(IIIc)

In formula (IIIc), each L independently represents a substituted or unsubstituted aryl group, or a substituted or unsubstituted heteroaryl group, and each Q independently represents a substituted or unsubstituted 3,6-di-t-butyl-9H-carbazol-9-yl group, or a substituted or unsubstituted 3,6-diphenyl-9H-carbazol-9-yl group.

[8] The compound according to [1] above, represented by formula (IVa).

[Chemical formula 8]

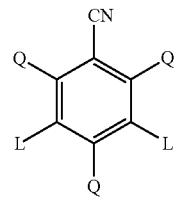

(IVa)

In formula (IVa), each L independently represents a substituted or unsubstituted aryl group, or a substituted or unsubstituted heteroaryl group, and each Q independently represents a substituted or unsubstituted 3,6-di-t-butyl-9H-carbazol-9-yl group, or a substituted or unsubstituted 3,6-diphenyl-9H-carbazol-9-yl group.

[9] The compound according to any one of [1] to [8] above, wherein L represents a substituted or unsubstituted, nitrogen-containing or oxygen-containing, 5-membered ring or 6-membered ring heteroaryl group.

[10] The compound according to any one of [1] to [8] above, wherein L represents a substituted or unsubstituted phenyl group, a substituted or unsubstituted biphenyl group, a substituted or unsubstituted naphthyl group, a substituted or unsubstituted anthryl group, a substituted or unsubstituted phenanthryl group, a substituted or unsubstituted pyridinyl group, a substituted or unsubstituted pyrimidinyl group, a substituted or unsubstituted furyl group, a substituted or unsubstituted thienyl group, a substituted or unsubstituted oxazolyl group, a substituted or unsubstituted thiazolyl group, a substituted or unsubstituted imidazolyl group, a substituted or unsubstituted indolyl group, a substituted or unsubstituted quinolinyl group, a substituted or unsubstituted benzofuranyl group, a substituted or unsubstituted benzothienyl group, a substituted or unsubstituted benzoxazolyl group, a substituted or unsubstituted benzothiazolyl group, or a substituted or unsubstituted benzimidazolyl group.

[11] The compound according to any one of [1] to [8] above, wherein L represents a substituted or unsubstituted phenyl group, a substituted or unsubstituted pyridinyl group, or a substituted or unsubstituted pyrimidinyl group.

[12] A light-emitting material containing the compound according to any one of [1] to [11] above.

[13] A light-emitting element containing the light-emitting material according to [12] above.

Effects of the Invention

The compound of the present invention is useful as a light-emitting material. Among the light-emitting materials according to the present invention are compounds which emit delayed fluorescence. A light-emitting element containing the light-emitting material according to the present invention is able to realize excellent luminous efficiency.

EMBODIMENTS FOR CARRYING OUT THE INVENTION

Figure 1:
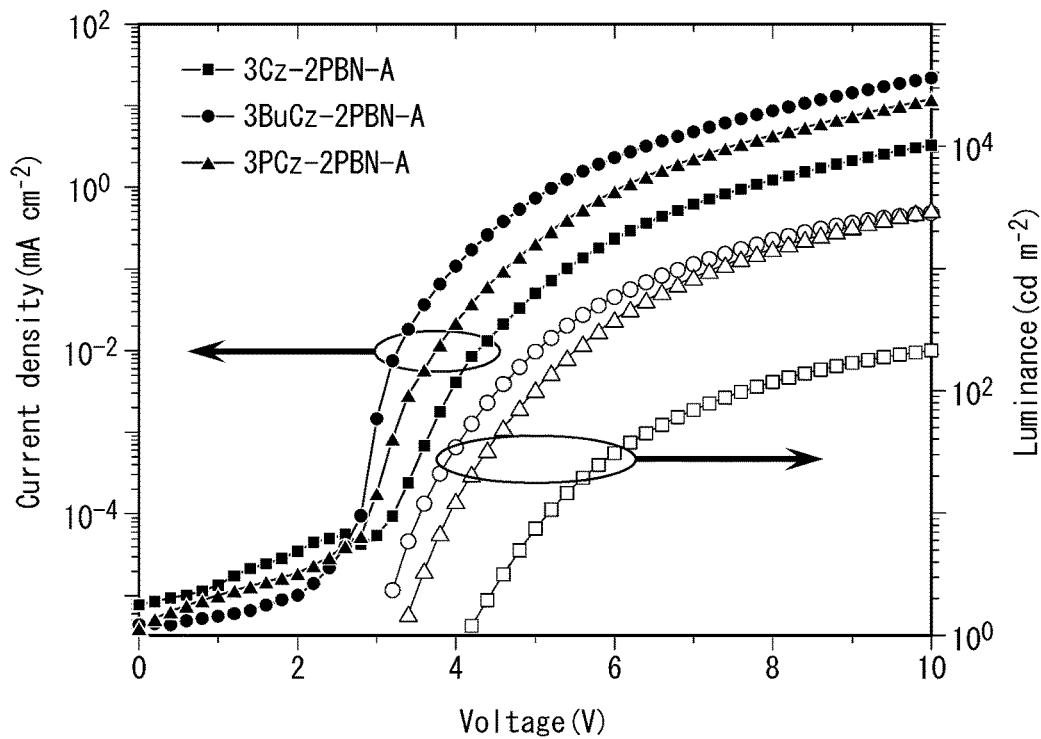
FIG. 1 is a diagram illustrating the voltage-current density-luminance characteristics for 3Cz-2PBN-A, 3BuCz-2PBN-A and 3PCz-2PBN-A.

The 2,3,4,5,6-pentasubstituted benzonitrile compound of the present invention is a compound represented by formula (I).

[Chemical formula 9]

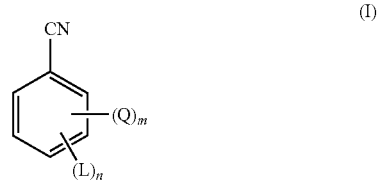

In formula (I), each L independently represents a substituted or unsubstituted aryl group, n indicates the number of L groups, and is either 1 or 2, each Q independently represents a substituted or unsubstituted 3,6-di-t-butyl-9H-carbazol-9-yl group, a substituted or unsubstituted 3,6-diphenyl-9H-carbazol-9-yl group, or a substituted or unsubstituted 3-phenyl-6-t-butyl-9H-carbazol-9-yl group, and m indicates the number of Q groups, and has a value of 5−n.

The 2,3,4,5,6-pentasubstituted benzonitrile compound of the present invention is preferably a compound represented by formula (IIa), formula (IIb), formula (IIc), formula (IIIa), formula (IIIb), formula (IIIc) or formula (IVa), and is more preferably a compound represented by formula (IIa). The 2,3,4,5,6-pentasubstituted benzonitrile compound of the present invention may also be a compound represented by formula (IIId) or formula (IIIe).

[Chemical formula 10]

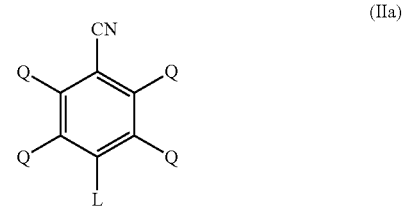

In formula (IIa), L represents a substituted or unsubstituted aryl group, and each Q independently represents a substituted or unsubstituted 3,6-di-t-butyl-9H-carbazol-9-yl group.

[Chemical formula 11]

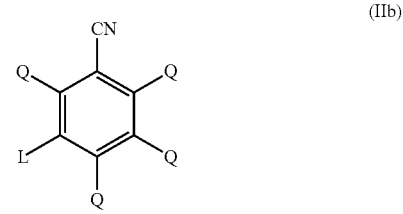

In formula (IIb), L represents a substituted or unsubstituted aryl group, and each Q independently represents a substituted or unsubstituted 3,6-di-t-butyl-9H-carbazol-9-yl group.

[Chemical formula 12]

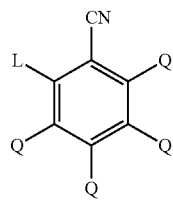

(IIc)

In formula (IIc), L represents a substituted or unsubstituted aryl group, and each Q independently represents a substituted or unsubstituted 3,6-di-t-butyl-9H-carbazol-9-yl group.

[Chemical formula 13]

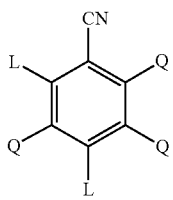

(IIIa)

In formula (IIIa), each L independently represents a substituted or unsubstituted aryl group, and each Q independently represents a substituted or unsubstituted 3,6-di-t-butyl-9H-carbazol-9-yl group, or a substituted or unsubstituted 3,6-diphenyl-9H-carbazol-9-yl group.

[Chemical formula 14]

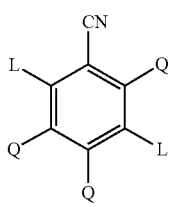

(IIIb)

In formula (IIIb), each L independently represents a substituted or unsubstituted aryl group, and each Q independently represents a substituted or unsubstituted 3,6-di-t-butyl-9H-carbazol-9-yl group, or a substituted or unsubstituted 3,6-diphenyl-9H-carbazol-9-yl group.

[Chemical formula 15]

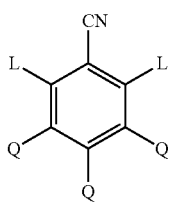

(IIIc)

In formula (IIIc), each L independently represents a substituted or unsubstituted aryl group, and each Q independently represents a substituted or unsubstituted 3,6-di-t-butyl-9H-carbazol-9-yl group, or a substituted or unsubstituted 3,6-diphenyl-9H-carbazol-9-yl group.

[Chemical formula 16]

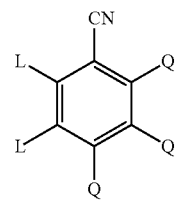

(IIId)

In formula (IIId), each L independently represents a substituted or unsubstituted aryl group, and each Q independently represents a substituted or unsubstituted 3,6-di-t-butyl-9H-carbazol-9-yl group, or a substituted or unsubstituted 3,6-diphenyl-9H-carbazol-9-yl group.

[Chemical formula 17]

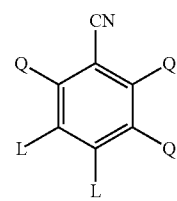

(IIIe)

In formula (IIIe), each L independently represents a substituted or unsubstituted aryl group, and each Q independently represents a substituted or unsubstituted 3,6-di-t-butyl-9H-carbazol-9-yl group, or a substituted or unsubstituted 3,6-diphenyl-9H-carbazol-9-yl group.

[Chemical formula 18]

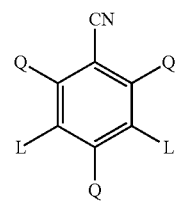

(IVa)

In formula (IVa), each L independently represents a substituted or unsubstituted aryl group, and each Q independently represents a substituted or unsubstituted 3,6-di-t-butyl-9H-carbazol-9-yl group, or a substituted or unsubstituted 3,6-diphenyl-9H-carbazol-9-yl group.

The substituted or unsubstituted 3,6-di-t-butyl-9H-carbazol-9-yl group is preferably a group represented by formula (A).

[Chemical formula 19]

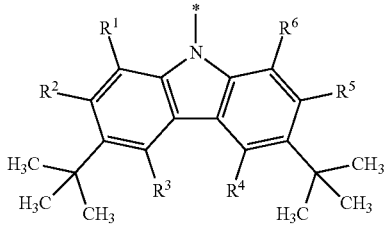

(A)

The substituted or unsubstituted 3,6-diphenyl-9H-carbazol-9-yl group is preferably a group represented by formula (B).

[Chemical formula 20]

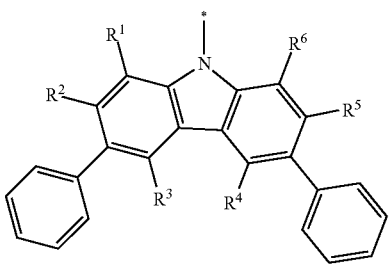

(B)

The substituted or unsubstituted 3-phenyl-6-t-butyl-9H-carbazol-9-yl group is preferably a group represented by formula (C).

[Chemical formula 21]

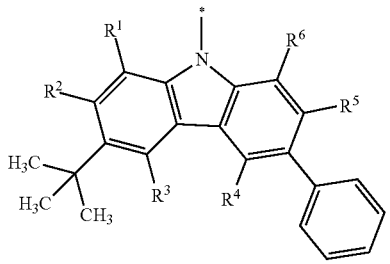

(C)

In formulas (A), (B) and (C), each of $R^1$, $R^2$, $R^3$, $R^4$, $R^5$ and $R^6$ independently represents a hydrogen atom or a substituent, and * represents a bonding site.

In the present invention, the term "unsubstituted" means only the core group. When a group is described using only the name of the core group, this means the unsubstituted group unless specifically stated otherwise.

On the other hand, the term "substituted" means a hydrogen atom of the core group has been substituted with a group having the same structure as the core group, or a different structure from the core group. Accordingly, a "substituent" is another group that is bonded to the core group. There may be one substituent, or two or more substituents. In the case of two or more substituents, the substituents may be the same or different.

There are no particular limitations on the "substituent", provided the substituent is chemically permissible, and the compound has the effects of the present invention.

Specific examples of groups that may function as a "substituent" include the groups exemplified below.

Halogeno groups such as a fluoro group, chloro group, bromo group and iodo group;

C1 to C20 alkyl groups (and preferably C1 to C6 alkyl groups) such as a methyl group, ethyl group, n-propyl group, i-propyl group, n-butyl group, s-butyl group, i-butyl group, t-butyl group, n-pentyl group and n-hexyl group;

C2 to C10 alkenyl groups (and preferably C2 to C6 alkenyl groups) such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group;

C2 to C10 alkynyl groups (and preferably C2 to C6 alkynyl groups) such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group;

C3 to C8 cycloalkyl groups such as a cyclopropyl group, cyclobutyl group, cyclopentyl group, cyclohexyl group, cycloheptyl group and cubanyl group;

C3 to C8 cycloalkenyl groups such as a 2-cyclopropenyl group, 2-cyclopentenyl group, 3-cyclohexenyl group and 4-cyclooctenyl group;

C6 to C40 aryl groups (and preferably C6 to C10 aryl groups) such as a phenyl group and naphthyl group;

5-membered ring heteroaryl groups such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group and tetrazolyl group;

6-membered ring heteroaryl groups such as a pyridyl group, pyrazinyl group, pyrimidinyl group, pyridazinyl group and triazinyl group;

condensed ring heteroaryl groups such as an indolyl group, benzofuryl group, benzothienyl group, benzimidazolyl group, benzoxazolyl group, benzothiazolyl group, quinolyl group, isoquinolyl group and quinoxalinyl group;

cyclic ether groups such as an oxiranyl group, tetrahydrofuryl group, dioxolanyl group and dioxiranyl group;

cyclic amino groups such as an aziridinyl group, pyrrolidinyl group, piperidyl group, piperazinyl group and morpholinyl group;

a hydroxy group; an oxo group;

C1 to C20 alkoxy groups (and preferably C1 to C6 alkoxy groups) such as a methoxy group, ethoxy group, n-propoxy group, i-propoxy group, n-butoxy group, s-butoxy group, i-butoxy group and t-butoxy group;

C2 to C6 alkenyloxy groups such as a vinyloxy group, allyloxy group, propenyloxy group and butenyloxy group;

C2 to C6 alkynyloxy groups such as an ethynyloxy group and a propargyloxy group;

C6 to C10 aryloxy groups such as a phenoxy group and a naphthoxy group;

5- and 6-membered ring heteroaryloxy groups such as a thiazolyloxy group and a pyridyloxy group;

a carboxyl group;

C1 to C6 alkylcarbonyl groups such as a formyl group, acetyl group and propionyl group;

C1 to C6 alkylcarbonyloxy groups such as a formyloxy group, acetyloxy group and propionyloxy group;

C1 to C6 alkoxycarbonyl groups such as a methoxycarbonyl group, ethoxycarbonyl group, n-propoxycarbonyl group, i-propoxycarbonyl group, n-butoxycarbonyl group and t-butoxycarbonyl group;

C1 to C6 haloalkyl groups such as a chloromethyl group, chloroethyl group, trifluoromethyl group, 1,2-dichloro-n-propyl group, 1-fluoro-n-butyl group and perfluoro-n-pentyl group;

C2 to C6 haloalkenyl groups such as a 2-chloro-1-propenyl group and a 2-fluoro-1-butenyl group;

C2 to C6 haloalkynyl groups such as a 4,4-dichloro-1-butynyl group, 4-fluoro-1-pentynyl group and 5-bromo-2-pentynyl group;

C3 to C6 halocycloalkyl groups such as a 3,3-difluorocyclobutyl group;

C1 to C6 haloalkoxy groups such as a 2-chloro-n-propoxy group, 2,3-dichlorobutoxy group, trifluoromethoxy group and 2,2,2-trifluoroethoxy group;

C2 to C6 haloalkenyloxy groups such as a 2-chloropropenyloxy group and a 3-bromobutenyloxy group;

C1 to C6 haloalkylcarbonyl groups such as a chloroacetyl group, trifluoroacetyl group and trichloroacetyl group;

a cyano group; a nitro group; an amino group;

C1 to C20 alkylamino groups (and preferably C1 to C6 alkylamino groups) such as a methylamino group, dimethylamino group and diethylamino group;

C6 to C40 arylamino groups (and preferably C6 to C10 arylamino groups) such as an anilino group and a naphthylamino group;

C1 to C6 alkylcarbonylamino groups such as a formylamino group, acetylamino group, propanoylamino group, butyrylamino group and i-propylcarbonylamino group;

C1 to C6 alkoxycarbonylamino groups such as a methoxycarbonylamino group, ethoxycarbonylamino group, n-propoxycarbonylamino group and i-propoxycarbonylamino group;

C1 to C6 alkylsulfoxyimino groups such as an S,S-dimethylsulfoxyimino group;

an aminocarbonyl group;

C1 to C6 alkylaminocarbonyl groups such as a methylaminocarbonyl group, dimethylaminocarbonyl group, ethylaminocarbonyl group and i-propylaminocarbonyl group;

imino C1 to C6 alkyl groups such as an iminomethyl group, (1-imino)ethyl group and (1-imino)-n-propyl group;

hydroxyimino C1 to C6 alkyl groups such as a hydroxyiminomethyl group, (1-hydroxyimino)ethyl group and (1-hydroxyimino)propyl group;

C1 to C6 alkoxyimino C1 to C6 alkyl groups such as a methoxyiminomethyl group and a (1-methoxyimino)ethyl group;

a mercapto group;

C1 to C20 alkylthio groups (and preferably C1 to C6 alkylthio groups) such as a methylthio group, ethylthio group, n-propylthio group, i-propylthio group, n-butylthio group, i-butylthio group, s-butylthio group and t-butylthio group;

C1 to C6 haloalkylthio groups such as a trifluoromethylthio group and a 2,2,2-trifluoroethylthio group;

C2 to C6 alkenylthio groups such as a vinylthio group and an allylthio group;

C2 to C6 alkynylthio groups such as an ethynylthio group and a propargylthio group;

C1 to C6 alkylsulfinyl groups such as a methylsulfinyl group, ethylsulfinyl group and t-butylsulfinyl group;

C1 to C6 haloalkylsulfinyl groups such as a trifluoromethylsulfinyl group and a 2,2,2-trifluoroethylsulfinyl group;

C2 to C6 alkenylsulfinyl groups such as an allylsulfinyl group;

C2 to C6 alkynylsulfinyl groups such as a propargylsulfinyl group;

C1 to C6 alkylsulfonyl groups such as a methylsulfonyl group, ethylsulfonyl group and t-butylsulfonyl group;

C1 to C6 haloalkylsulfonyl groups such as a trifluoromethylsulfonyl group and a 2,2,2-trifluoroethylsulfonyl group;

C2 to C6 alkenylsulfonyl groups such as an allylsulfonyl group;

C2 to C6 alkynylsulfonyl groups such as a propargylsulfonyl group;

C2 to C20 alkylamido groups such as an acetamido group, N-methylamido group, N-ethylamido group, N-(n-propyl)amido group, N-(n-butyl)amido group, N-isobutylamido group, N-(sec-butyl)amido group, N-(t-butyl)amido group, N,N-dimethylamido group, N,N-diethylamido group, N,N-di(n-propyl)amido group, N,N-di(n-butyl)amido group, N,N-diisobutylamido group, N-methylacetamido group, N-ethylacetamido group, N-(n-propyl)acetamido group, N-(n-butyl)acetamido group, N-isobutylacetamido group, N-(sec-butyl)acetamido group, N-(t-butyl)acetamido group, N,N-dimethylacetamido group, N,N-diethylacetamido group, N,N-di(n-propyl)acetamido group, N,N-di(n-butyl)acetamido group and N,N-diisobutylacetamido group;

C6 to C20 arylamido groups such as a phenylamido group, naphthylamido group, phenylacetamido group and naphthylacetamido group;

tri-C1 to C10 alkylsilyl groups (and preferably tri-C1 to C6 alkylsilyl groups) such as a trimethylsilyl group, triethylsilyl group and t-butyldimethylsilyl group; and tri-C6 to C10 arylsilyl groups such as a triphenylsilyl group.

Further, any hydrogen atom in any of these "substituents" may be substituted with a group of a different structure.

Expressions such as "C1 to C6" indicate that the number of carbon atoms in the core group is within a range from 1 to 6. This number of carbon atoms does not include carbon atoms that exist in any substituents. For example, an ethoxybutyl group has a butyl group as the core group and an ethoxy group as a substituent, and is therefore classified as a C2 alkoxy C4 alkyl group.

Examples of preferred substituents include a hydroxy group, halogeno groups, a cyano group, alkyl groups of 1 to 20 carbon atoms, alkoxy groups of 1 to 20 carbon atoms, alkylthio groups of 1 to 20 carbon atoms, alkyl-substituted amino groups of 1 to 20 carbon atoms, acyl groups of 2 to 20 carbon atoms, aryl groups of 6 to 40 carbon atoms, heteroaryl groups of 3 to 40 carbon atoms, diarylamino groups of 12 to 40 carbon atoms, substituted or unsubstituted carbazolyl groups of 12 to 40 carbon atoms, alkenyl groups of 2 to 10 carbon atoms, alkynyl groups of 2 to 10 carbon atoms, alkoxycarbonyl groups of 2 to 10 carbon atoms, alkylsulfonyl groups of 1 to 10 carbon atoms, haloalkyl groups of 1 to 10 carbon atoms, an amido group, alkylamido groups of 2 to 10 carbon atoms, trialkylsilyl groups of 3 to 20 carbon atoms, trialkylsilylalkyl groups of 4 to 20 carbon atoms, trialkylsilylalkenyl groups of 5 to 20 carbon atoms, trialkylsilylalkynyl groups of 5 to 20 carbon atoms, and a nitro group.

Examples of more preferred substituents include halogeno groups, a cyano group, alkyl groups of 1 to 20 carbon atoms, alkoxy groups of 1 to 20 carbon atoms, aryl groups of 6 to 40 carbon atoms, heteroaryl groups of 3 to 40 carbon atoms, diarylamino groups of 12 to 40 carbon atoms, and carbazolyl groups of 12 to 40 carbon atoms.

Examples of even more preferred substituents include a fluoro group, chloro group, cyano group, alkyl groups of 1 to 10 carbon atoms, alkoxy groups of 1 to 10 carbon atoms, dialkylamino groups of 1 to 10 carbon atoms, aryl groups of 6 to 15 carbon atoms, and heteroaryl groups of 3 to 12 carbon atoms. Among these substituents, substituents which are capable of being further substituted may themselves be substituted with an aforementioned substituent.

The substituted or unsubstituted aryl group for L is preferably a substituted or unsubstituted phenyl group, substituted or unsubstituted biphenyl group, substituted or unsubstituted naphthyl group, substituted or unsubstituted anthryl group, or substituted or unsubstituted phenanthryl group. Among these, a substituted or unsubstituted phenyl group is particularly preferred.

The compound of the present invention is not particularly limited in terms of production method, and for example, can be obtained by applying the methods disclosed in Patent Document 1 or Patent Document 2, or the methods described in the examples, using compounds corresponding with the pertinent substituents as starting materials.

Purification of the synthesized compound of the present invention may be conducted by purification by column chromatography, adsorption purification using silica gel, activated carbon, or activated clay or the like, or recrystallization or crystallization using solvents. Identification of the compound may be conducted by NMR analysis or the like.

The compound of the present invention can be used as a light-emitting material. Using the light-emitting material of the present invention, a light-emitting element such as an organic photoluminescent element or an organic electroluminescent element can be provided. The compound of the present invention has a function of assisting light emission from another light-emitting material (a host material), and can therefore be used to dope the other light-emitting material.

An organic photoluminescent element that represents one light-emitting element of the present invention has a light-emitting layer containing the light-emitting material of the present invention provided on a substrate. The light-emitting layer can be obtained by a coating method such as spin coating, a printing method such as inkjet printing, or a vapor deposition method or the like.

An organic electroluminescent element of the present invention is prepared by providing an organic layer between an anode and a cathode. In the present invention, the term "organic layer" means a layer composed substantially of organic matter which is positioned between an anode and a cathode, although this type of layer may also contain inorganic material provided the performance of the light-emitting element of the present invention is not impaired.

Examples of the structure in one embodiment of an organic electroluminescent element of the present invention include structures having an anode, a hole injection layer, a hole transport layer, an electron-blocking layer, a light-emitting layer, a hole-blocking layer, an electron transport layer and a cathode formed sequentially on a substrate, as well as structures having an additional electron injection layer between the electron transport layer and the cathode. In these multilayer structures, one or more of the organic layers may be omitted, and for example, structures having an anode, a hole transport layer, a light-emitting layer, an electron transport layer, an electron injection layer and a cathode formed sequentially on a substrate, or structures having an anode, a hole transport layer, a light-emitting layer, an electron transport layer and a cathode formed sequentially on a substrate may also be formed.

The light-emitting material of the present invention may be used to dope not only the light-emitting layer, but also the hole injection layer, hole transport layer, electron-blocking layer, hole-blocking layer, electron transport layer or electron injection layer.

The substrate acts as a support body for the light-emitting element, and a silicon plate, quartz plate, glass plate, metal plate, metal foil, resin film, or resin sheet or the like can be used as the substrate. Glass plates and plates of transparent synthetic resins such as polyesters, polymethacrylates, polycarbonates and polysulfones are particularly preferred. In those cases where a synthetic resin plate is used, the gas barrier properties must also be considered. If the gas barrier properties of the substrate are insufficient, then the light-emitting element may sometimes deteriorate due to external gas that has passed through the substrate. Accordingly, a dense silicon oxide film or the like is preferably provided on either one or both surfaces of the synthetic resin substrate to ensure favorable gas barrier properties.

An anode is provided on the substrate. A material having a large work function is generally used for the anode. Examples of the material for the anode include metals such as aluminum, gold, silver, nickel, palladium and platinum, metal oxides such as indium oxide, tin oxide, ITO, zinc oxide, $In_2O_3$—ZnO and IGZO, halogenated metals such as copper iodide, carbon black, and conductive polymers such as poly(3-methylthiophene), polypyrrole and polyaniline. Formation of the anode is typically conducted by a sputtering method or vacuum vapor deposition method or the like. Further, in the case of fine particles of metals such as silver, fine particles of copper iodide or the like, carbon black, fine particles of conductive metal oxides, or fine powders of conductive polymers, the anode can also be formed by dispersion in a suitable binder resin solution, and then application of the dispersion to the substrate. Moreover, in the case of conductive polymers, the anode can also be formed by forming a thin film directly on the substrate by electrolytic polymerization, or by applying the conductive polymer to the substrate.

The anode may also be formed by stacking two or more different types of materials. The thickness of the anode varies depending on the level of transparency required. In those cases where transparency is required, it is desirable that the transmittance of visible light is typically at least 60%, and preferably 80% or greater, and in such cases, the thickness of the anode is typically within a range from 10 to 1,000 nm, and preferably from 10 to 200 nm. In the case of a non-transparent anode, the anode may be of a similar thickness to the substrate. The sheet resistance of the anode is preferably at least several hundred $\Omega$/square.

The optionally provided hole injection layer may be formed using a porphyrin compound typified by copper phthalocyanine, or a naphthalenediamine derivative, starburst-type triphenylamine derivative, a triphenylamine trimer or tetramer such as an arylamine compound having a structure in which three or more triphenylamine structures are connected via single bonds or divalent groups containing no hetero atoms, an acceptor heterocyclic compound such as hexacyanoazatriphenylene, or a coating-type polymer material. These materials may be used to form a thin film by a vapor deposition method or other known methods such as a spin coating method or inkjet method.

The hole transport material used for the optionally provided hole transport layer preferably exhibits high hole injection efficiency from the anode and is capable of efficiently transporting the injected holes. Accordingly, the material preferably has a small ionization potential and high transparency relative to visible light, and also exhibits large hole mobility, has superior stability, and is unlikely to form impurities that may act as traps during production or use. In addition to these general requirements, if application to vehicle displays is also taken into consideration, then the element preferably also has high heat resistance. Accordingly, a material having a Tg value of at least 70° C. is desirable.

Examples of the material for the optionally provided hole transport layer include triazole derivatives, oxadiazole derivatives, imidazole derivatives, carbazole derivatives, indolocarbazole derivatives, polyarylalkane derivatives, pyrazoline derivatives, pyrazolone derivatives, phenylenediamine derivatives, arylamine derivatives, amin-substituted chalcone derivatives, oxazole derivatives, styrylanthracene derivatives, fluorenone derivatives, hydrazone derivatives, stilbene derivatives, silazane derivatives, aniline-based copolymers, and conductive polymer oligomers.

More specific examples include compounds containing an m-carbazolylphenyl group, benzidine derivatives such as N,N'-diphenyl-N,N'-di(m-tolyl)-benzidine (hereafter abbreviated as TPD), N,N'-diphenyl-N,N'-di(α-naphthyl)-benzidine (hereafter abbreviated as NPD) and N,N,N',N'-tetrabiphenylylbenzidine, 1,1-bis[(di-4-tolylamino)phenyl] cyclohexane (hereafter abbreviated as TAPC), various triphenylamine trimers and tetramers, and carbazole derivatives. These compounds may be used individually, or a combination of two or more compounds may be used. The hole transport layer may be a film with a single-layer structure, or a film with a layered structure. Further, a coating-type polymer material such as poly(3,4-ethylenedioxythiophene) (hereafter abbreviated as PEDOT)/poly(styrene sulfonate) (hereafter abbreviated as PSS) may be used for a hole injection-transport layer. These materials may be used to form a thin film by a vapor deposition method or other known methods such as a spin coating method or inkjet method.

Furthermore, for the hole injection layer or the hole transport layer, a material obtained by P-doping of a material typically used for these layers with trisbromophenylamine hexachloroantimony, or a polymer compound having a PD structure as a partial structure may also be used. Examples of materials that can be used as the host material for the hole injection-transport layer include carbazole derivatives such as PPF, PPT, CBP, TCTA and mCP.

Examples of compounds that can be used favorably as the hole injection material include compounds (hi1) to (hi7) shown below.

[Chemical formula 22]

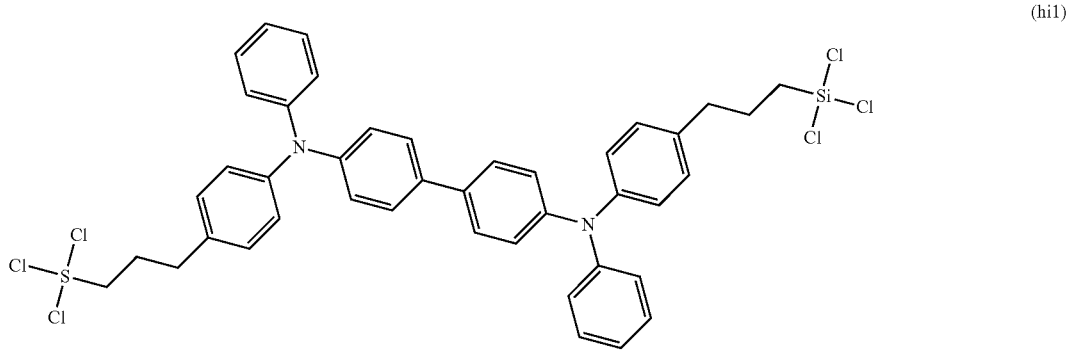

(hi1)

[Chemical formula 23]

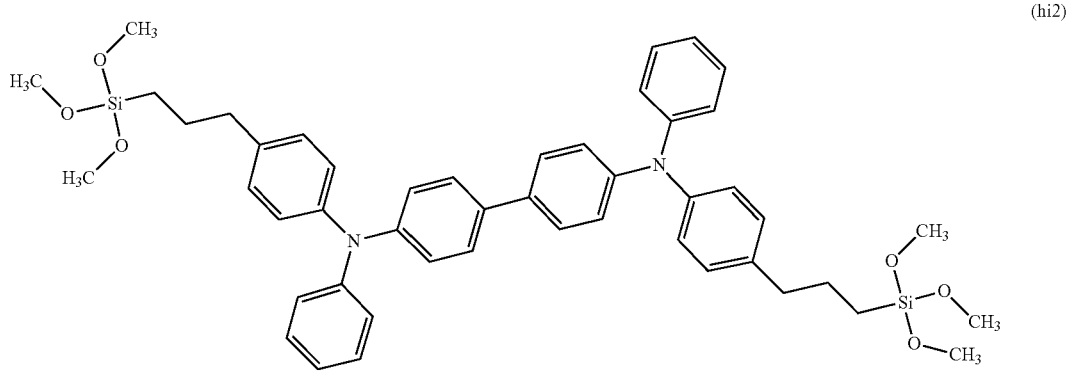

(hi2)

[Chemical formula 24]
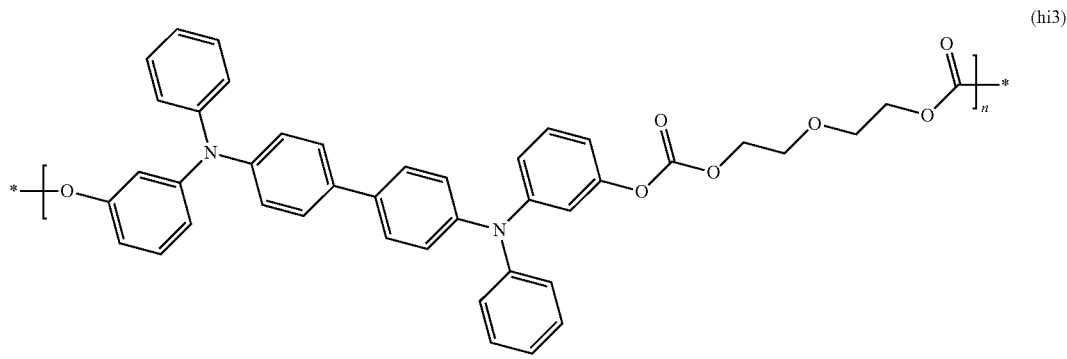
(hi3)
[Chemical formula 25]
(hi4)
[Chemical formula 26]
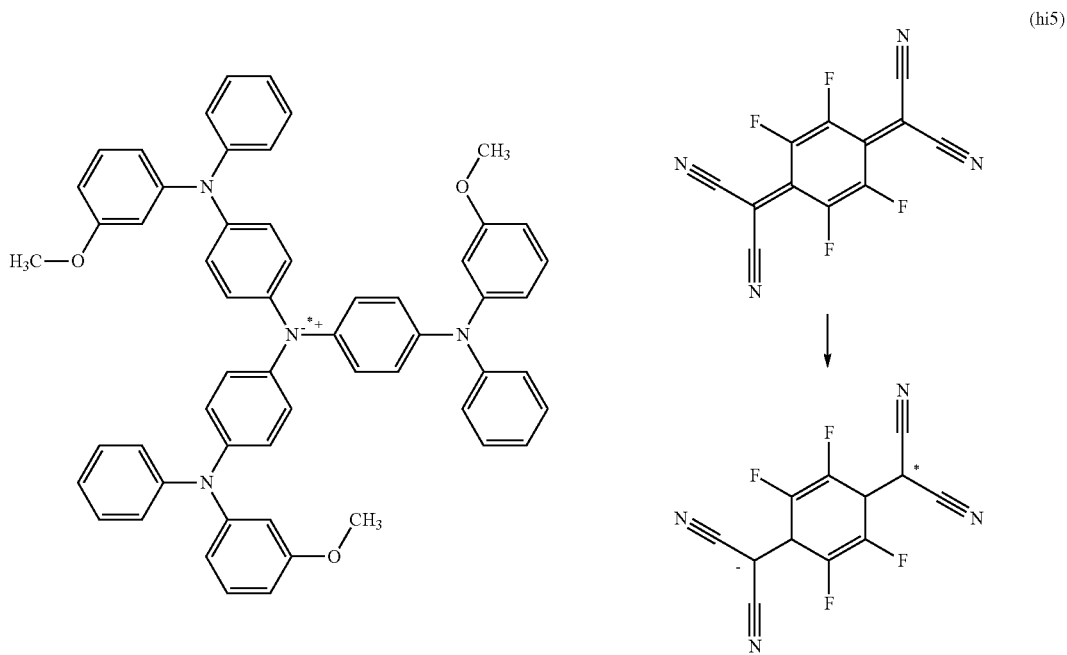
(hi5)

[Chemical formula 27]
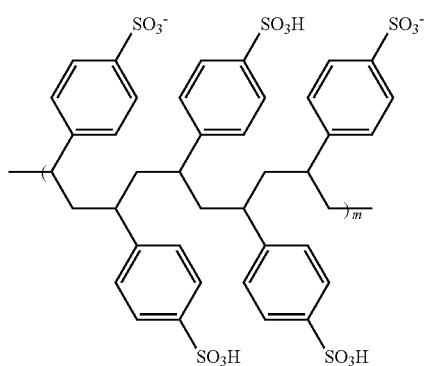
(hi6)
[Chemical formula 28]
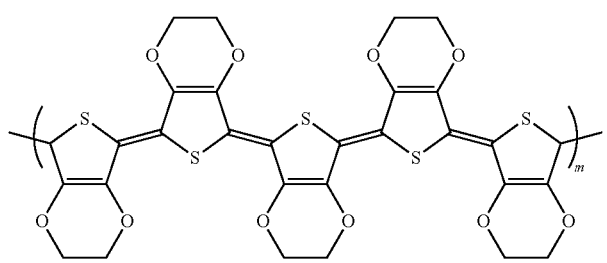
(hi7)
Examples of compounds that can be used favorably as the hole transport material include compounds (ht1) to (ht38) shown below.
[Chemical formula 29]
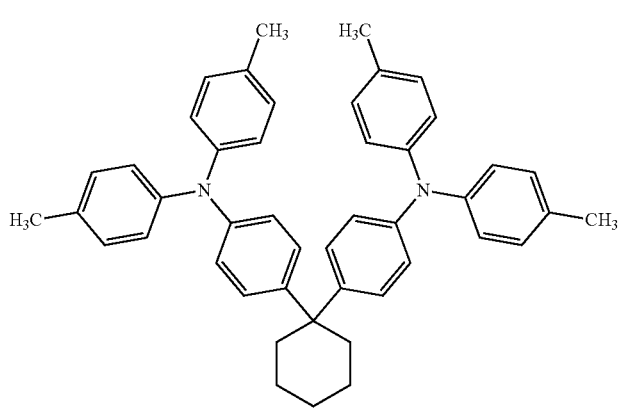
(ht1)
[Chemical formula 30]
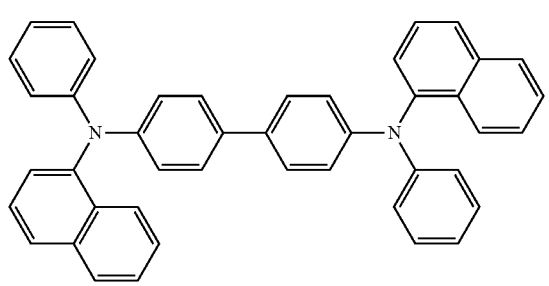
(ht2)

-continued
[Chemical formula 31]
(ht3)
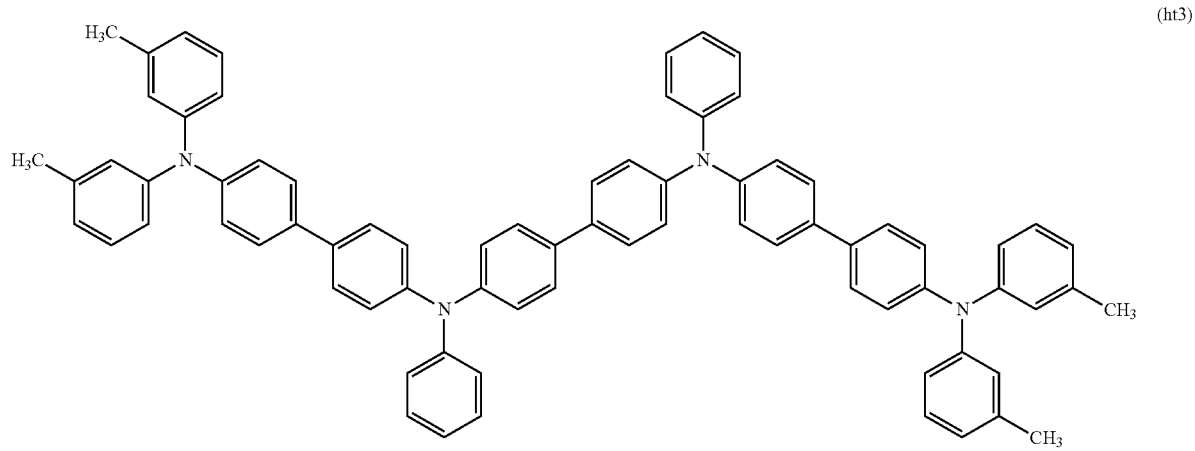
[Chemical formula 32]
(ht4)
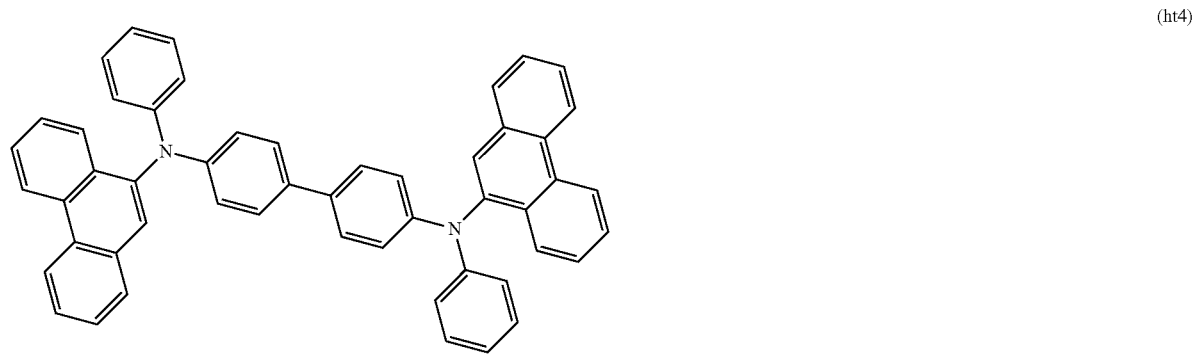
[Chemical formula 33]
(ht5)
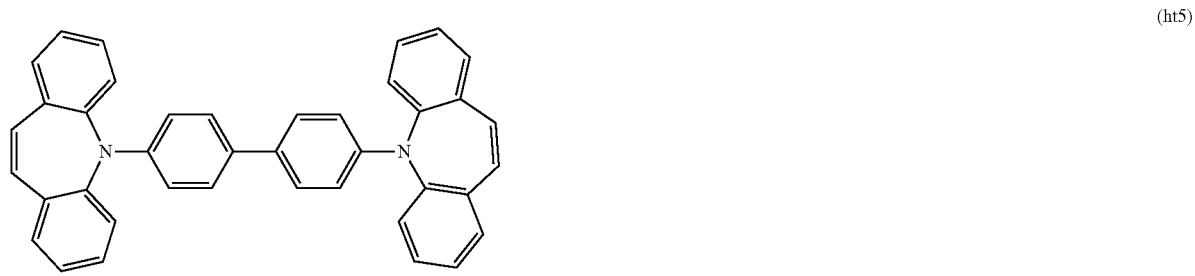
[Chemical formula 34]
(ht6)
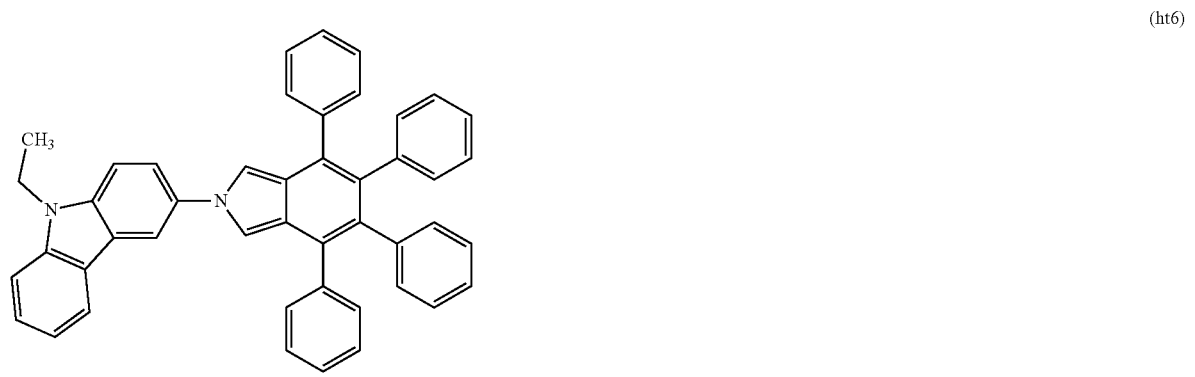

[Chemical formula 35]
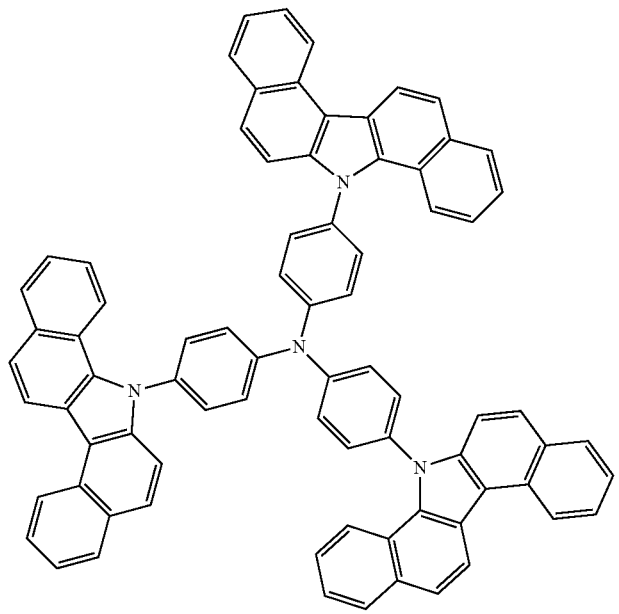
(ht7)
[Chemical formula 36]
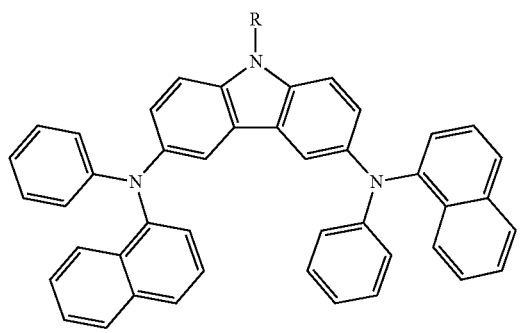
(ht8)
[Chemical formula 37]
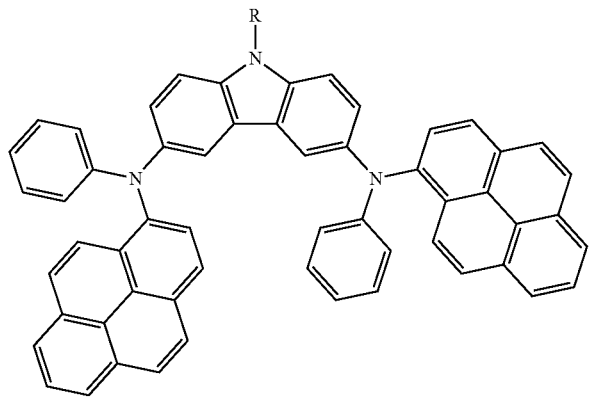
(ht9)

[Chemical formula 38]
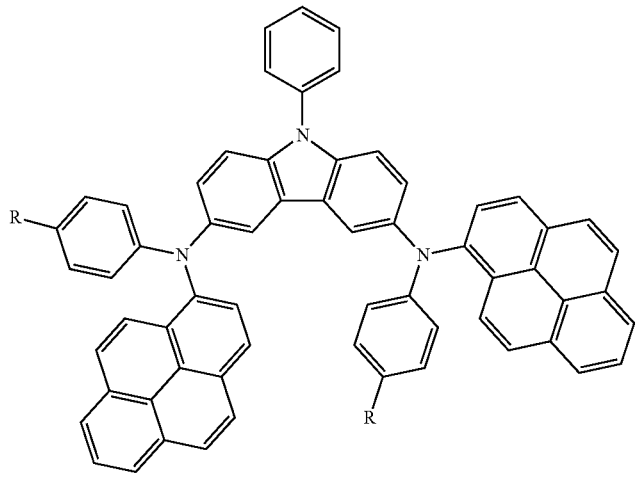
(ht10)
[Chemical formula 39]
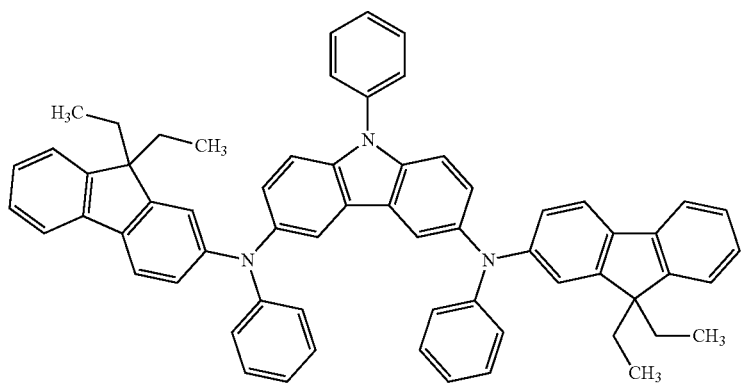
(ht11)
[Chemical formula 40]
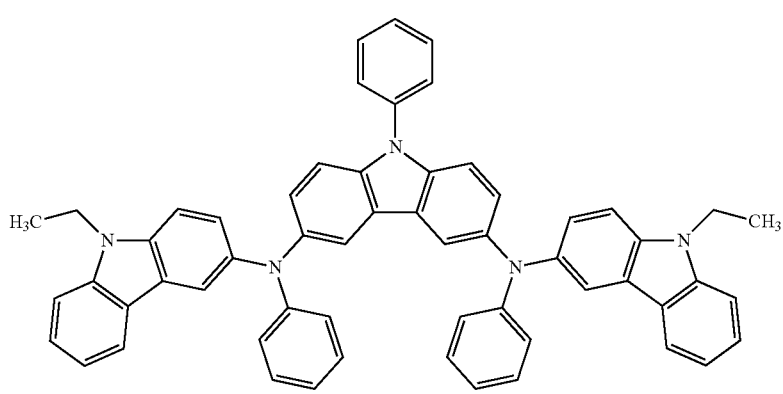
(ht12)

-continued
[Chemical formula 41]
(ht13)
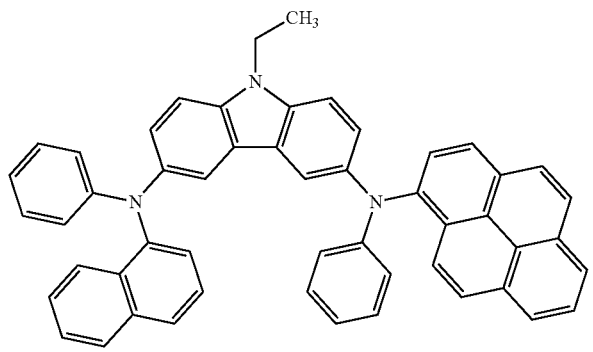
[Chemical formula 42]
(ht14)
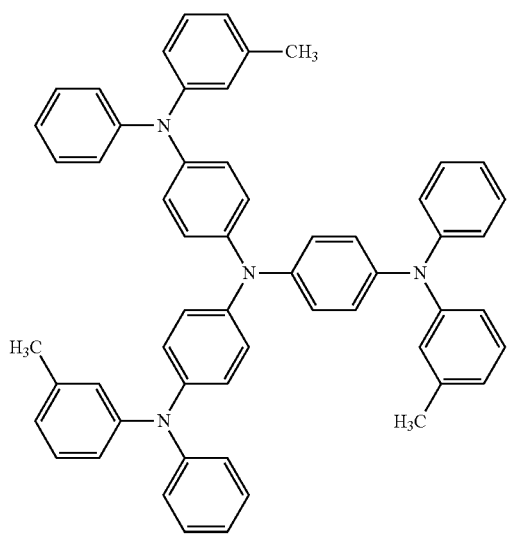
[Chemical formula 43]
(ht15)
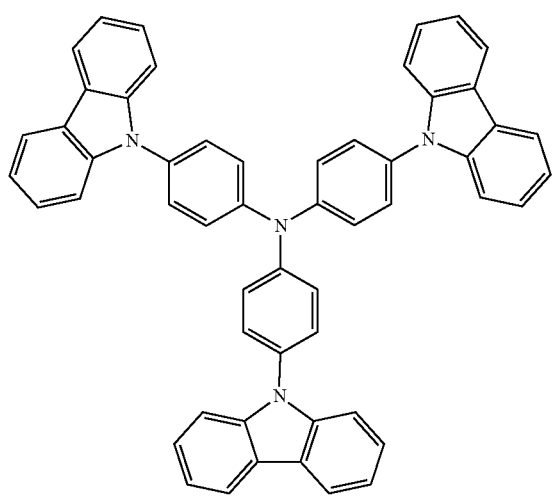

[Chemical formula 44]
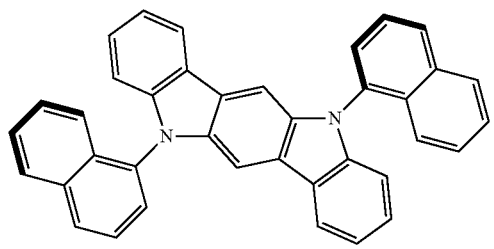
(ht16)
[Chemical formula 45]
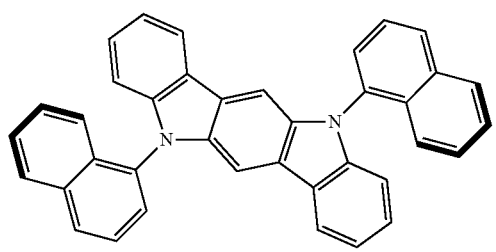
(ht17)
[Chemical formula 46]
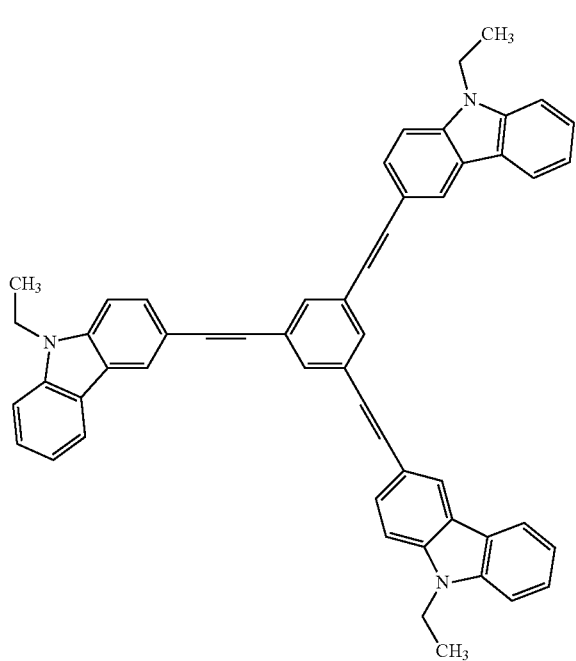
(ht18)

[Chemical formula 47]
(ht19)
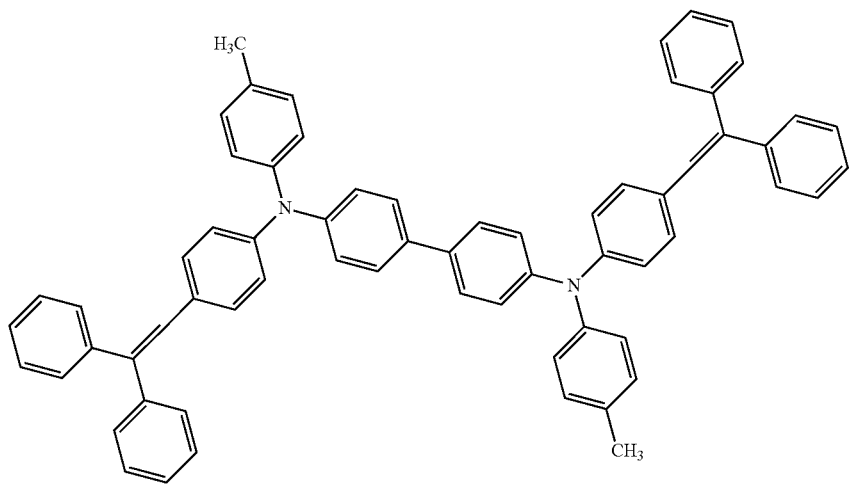
[Chemical formula 48]
(ht20)
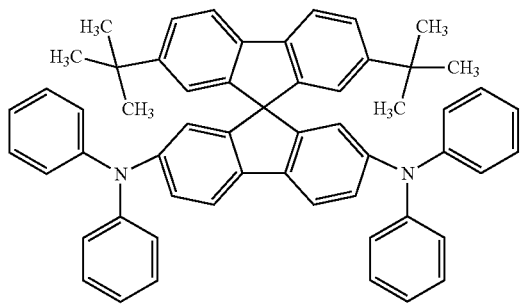
[Chemical formula 49]
(ht21)
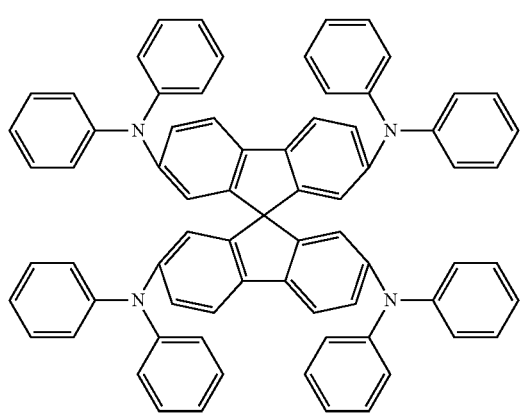

[Chemical formula 50]
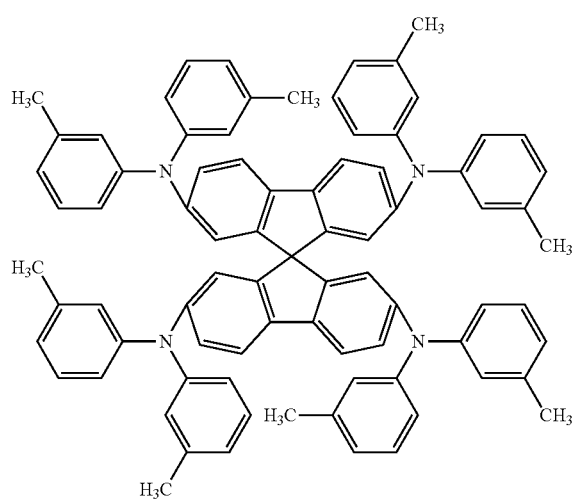
(ht22)
[Chemical formula 51]
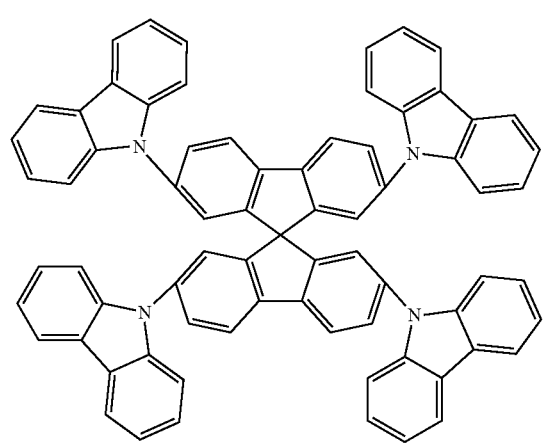
(ht23)
[Chemical formula 52]
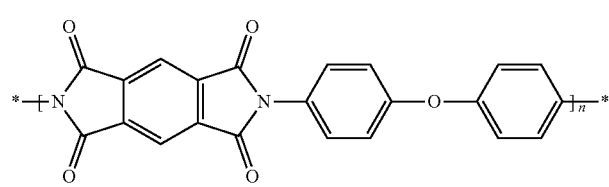
(ht24)
[Chemical formula 53]
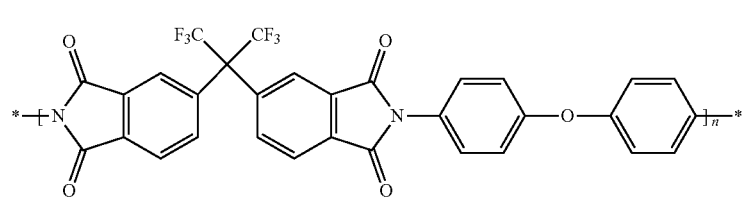
(ht25)

[Chemical formula 54]
(ht26)
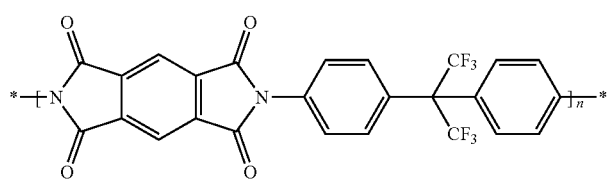
[Chemical formula 55]
(ht27)
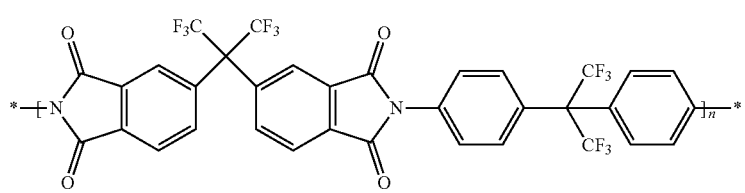
[Chemical formula 56]
(ht28)
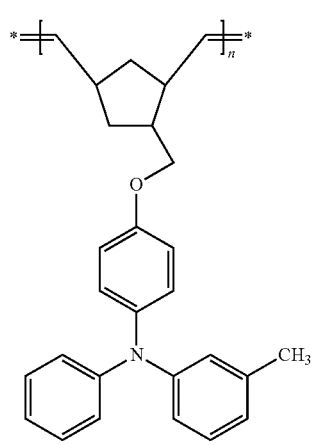
[Chemical formula 57]
(ht29)
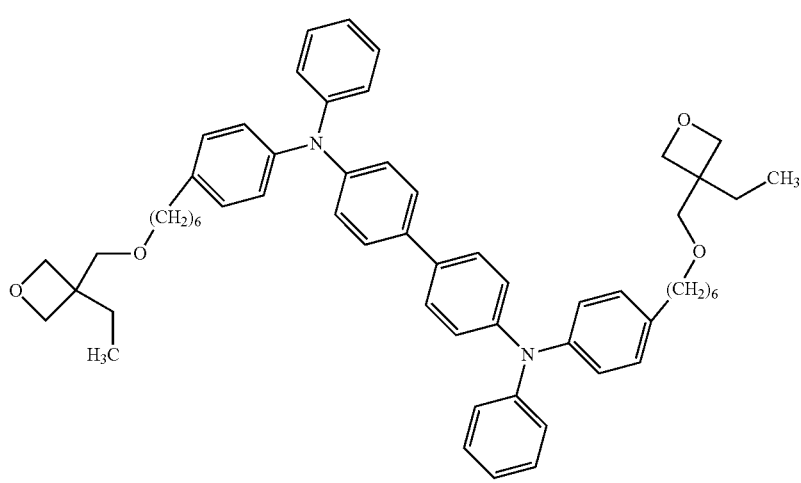

[Chemical formula 58]
(ht30)
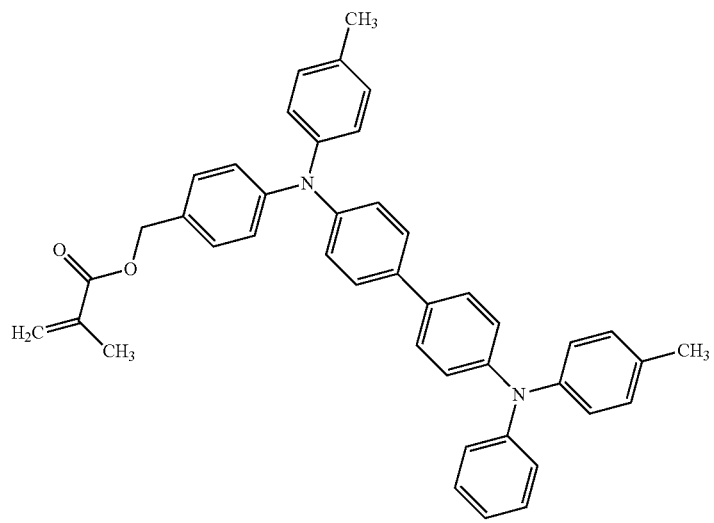
[Chemical formula 59]
(ht31)
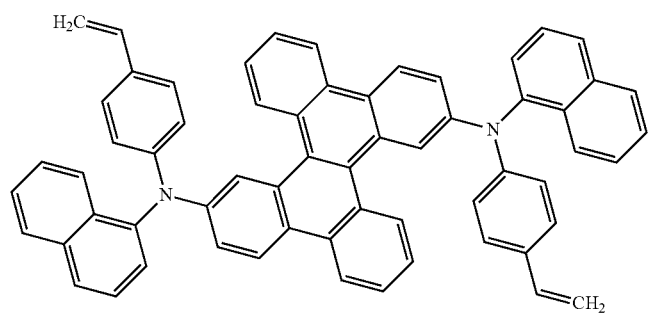
[Chemical formula 60]
(ht32)
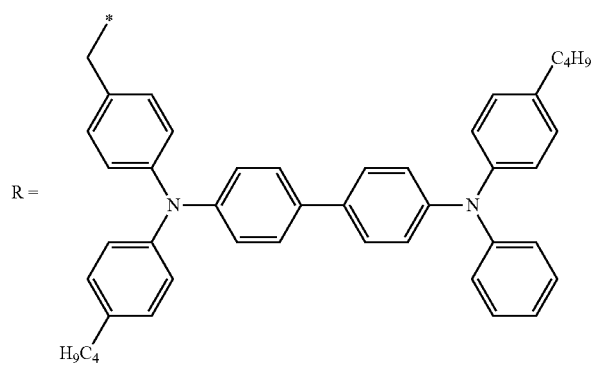

[Chemical formula 61]
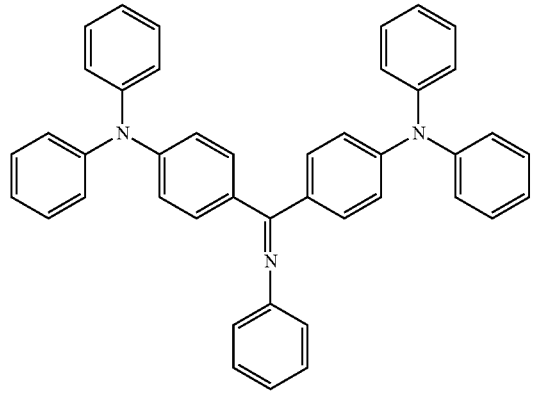
(ht33)
[Chemical formula 62]
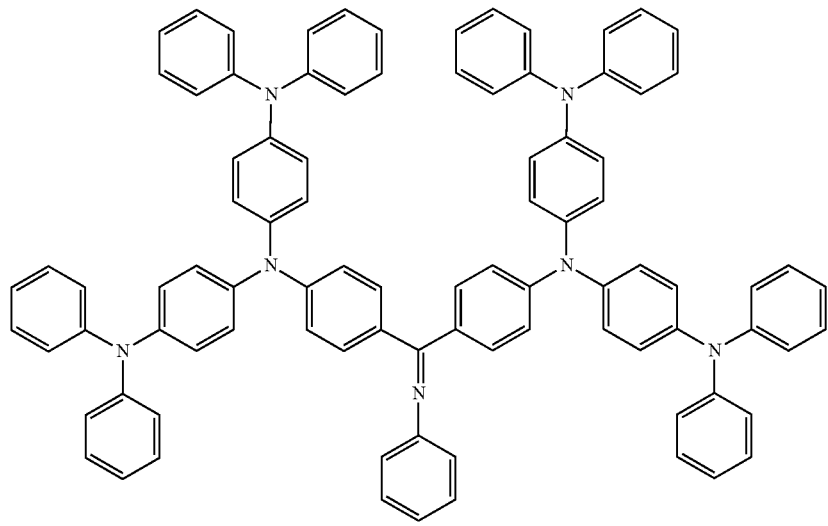
(ht34)
[Chemical formula 63]
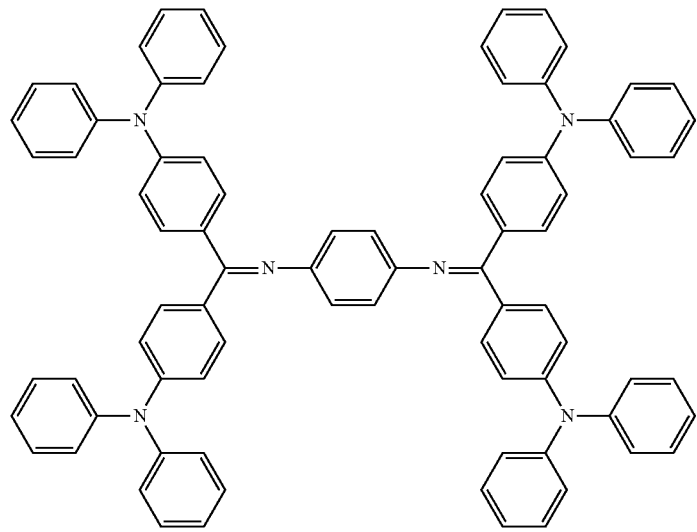
(ht35)

-continued
[Chemical formula 64]
(ht36)
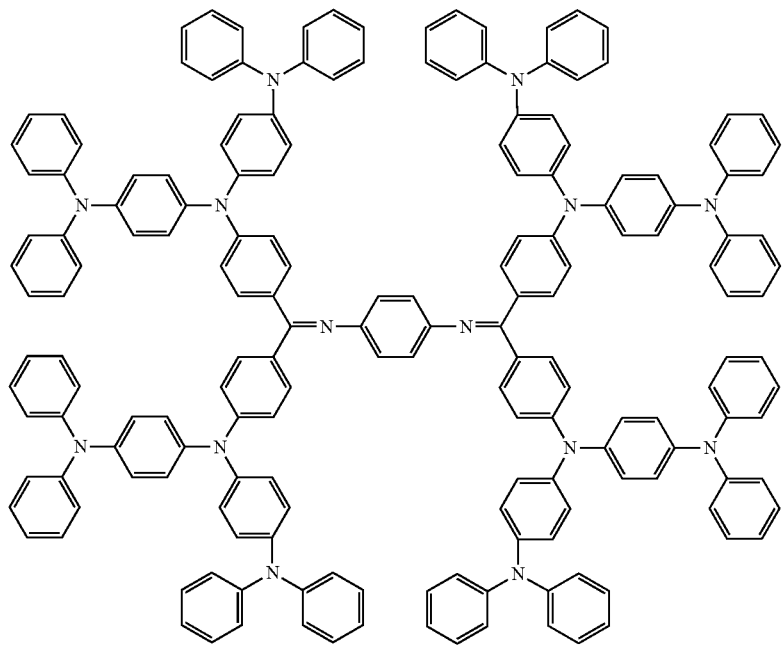
[Chemical formula 65]
(ht37)
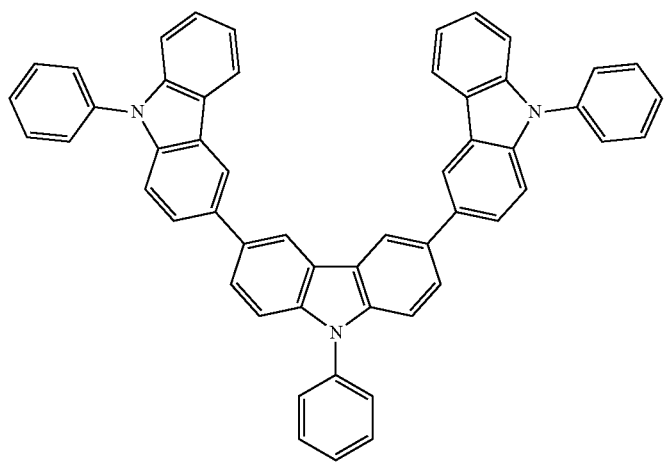
[Chemical formula 66]
(ht38)
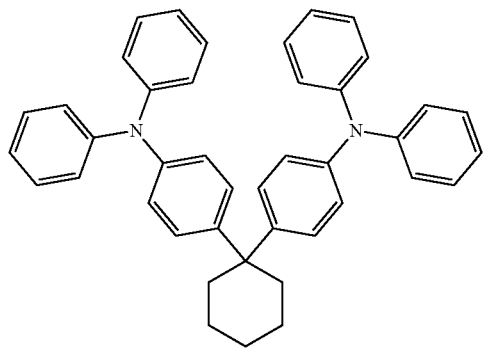

Examples of compounds that can be used as the optionally provided electron-blocking layer include compounds having an electron-blocking action, including carbazole derivatives such as 4,4',4"-tri(N-carbazolyl)triphenylamine (hereafter abbreviated as TCTA), 9,9-bis[4-(carbazol-9-yl)phenyl] fluorene, 1,3-bis(carbazol-9-yl)benzene (hereafter abbreviated as mCP), 2,2-bis(4-carbazol-9-ylphenyl)adamantane (hereafter abbreviated as Ad-Cz), and compounds having a triphenylsilyl group and a triarylamine structure typified by 9-[4-carbazol-9-yl]phenyl]-9-[4-(triphenylsilyl)phenyl]-9H-fluorene. These compounds may be used individually, or a combination of two or more compounds may be used. The electron-blocking layer may be a film with a single-layer structure, or a film with a layered structure. These materials may be used to form a thin film by a vapor deposition method or other known methods such as a spin coating method or inkjet method.

Examples of compounds that can be used favorably as the electron-blocking material include compounds (es1) to (es5) shown below.

[Chemical formula 67]

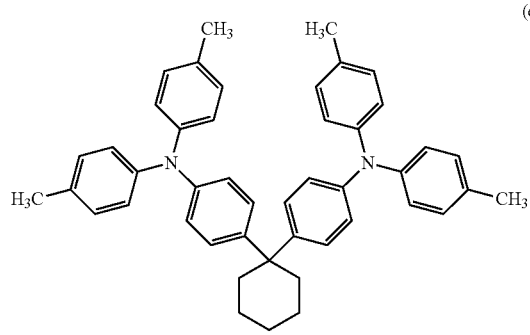

(es1)

[Chemical formula 68]

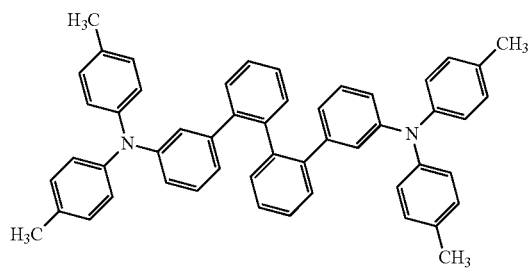

(es2)

[Chemical formula 69]

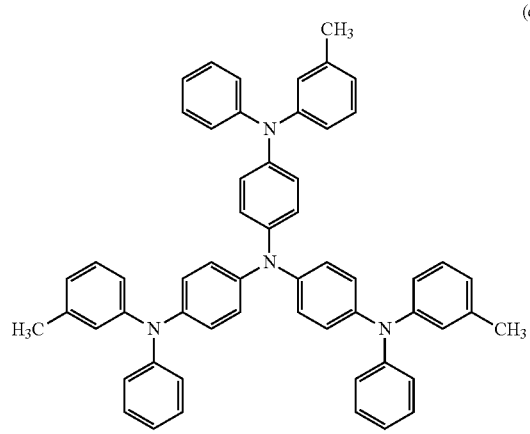

(es3)

[Chemical formula 70]

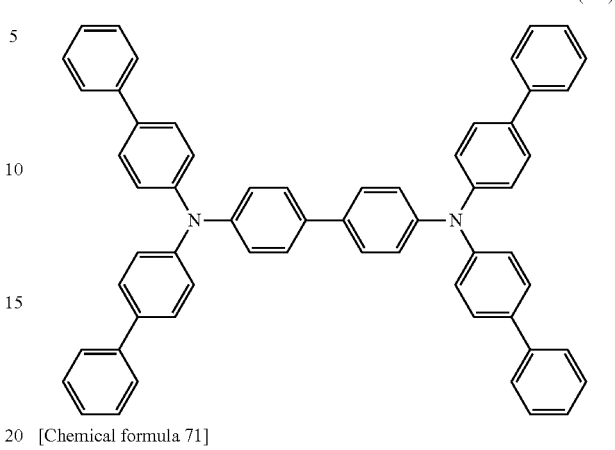

(es4)

[Chemical formula 71]

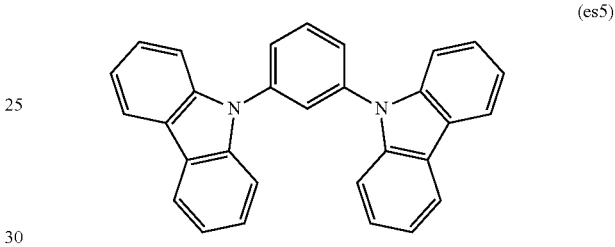

(es5)

The light-emitting layer is a layer that has the function of producing excitons and emitting light through the recombination of holes and electrons injected from the anode and cathode respectively. The light-emitting layer may be formed solely from the light-emitting material of the present invention, or may be formed by doping a host material with the light-emitting material of the present invention. Examples of the host material include PPF, PPT, metal complexes of quinolinol derivatives such as tris(8-hydroxyquinoline)aluminum (hereafter abbreviated as Alq3), anthracene derivatives, bisstyrylbenzene derivatives, pyrene derivatives, oxazole derivatives, polyparaphenylenevinylene derivatives, compounds having a bipyridyl group and an ortho-terphenyl structure, mCP, thiazole derivatives, benzimidazole derivatives, and polydialkylfluorene derivatives. The light-emitting layer may also contain a conventional dopant. Examples of such dopants include quinacridone, coumarin, rubrene, anthracene, perylene, and derivatives of these compounds, as well as benzopyran derivatives, rhodamine derivatives and aminostyryl derivatives. Further, phosphorescent light emitters including green phosphorescent emitters such as Ir(ppy)3, blue phosphorescent emitters such as FIRpic and FIr6, and red phosphorescent emitters such as Btp2Ir(acac) may also be used. These compounds may be used individually, or a combination of two or more compounds may be used. The light-emitting layer may be a film with a single-layer structure, or a film with a layered structure. These materials may be used to form a thin film by a vapor deposition method or other known methods such as a spin coating method or inkjet method.

In those cases where a host material is used, the amount of the light-emitting material of the present invention that may be included in the light-emitting layer has a lower limit that is preferably 0.1% by mass, and more preferably 1% by mass, and an upper limit that is preferably 50% by mass, more preferably 20% by mass, and even more preferably 10% by mass.

Examples of compounds that can be used favorably as the host material of the light-emitting layer include compounds (el1) to (el42) shown below.
[Chemical formula 72]
(e11)
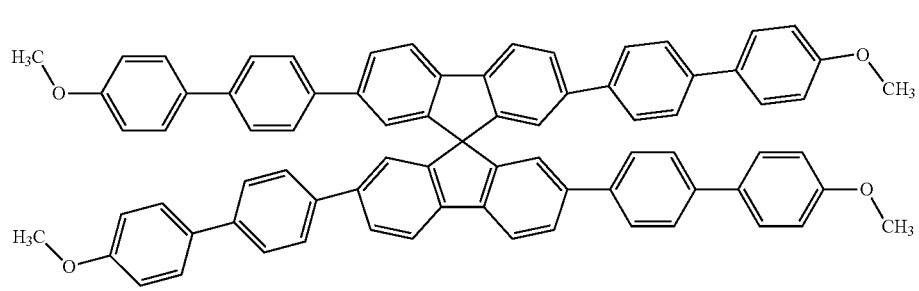
[Chemical formula 73]
(e12)
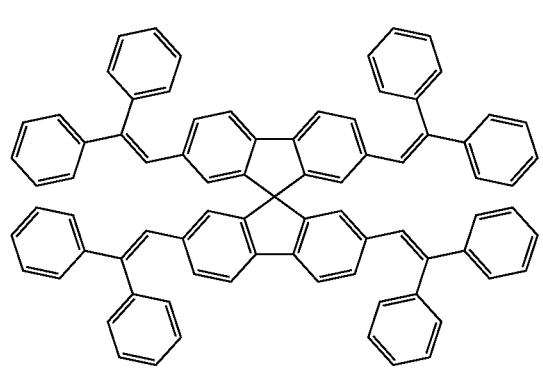
[Chemical formula 74]
(e13)
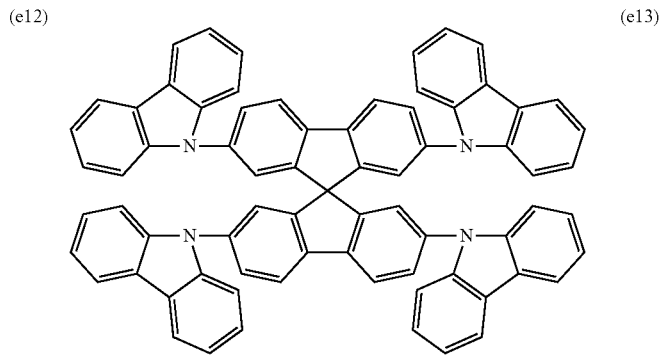
[Chemical formula 75]
(e14)
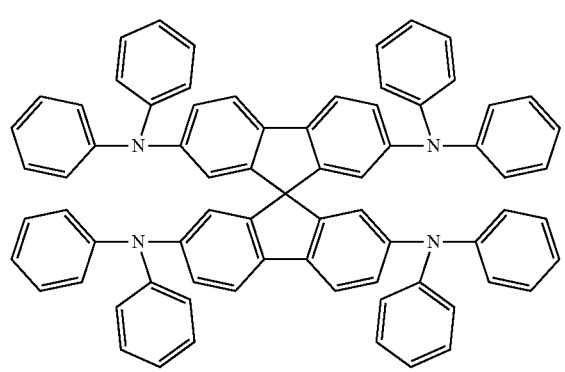
[Chemical formula 76]
(e15)
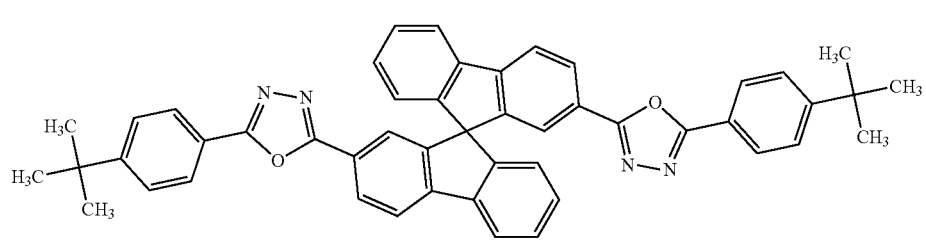

[Chemical formula 77]
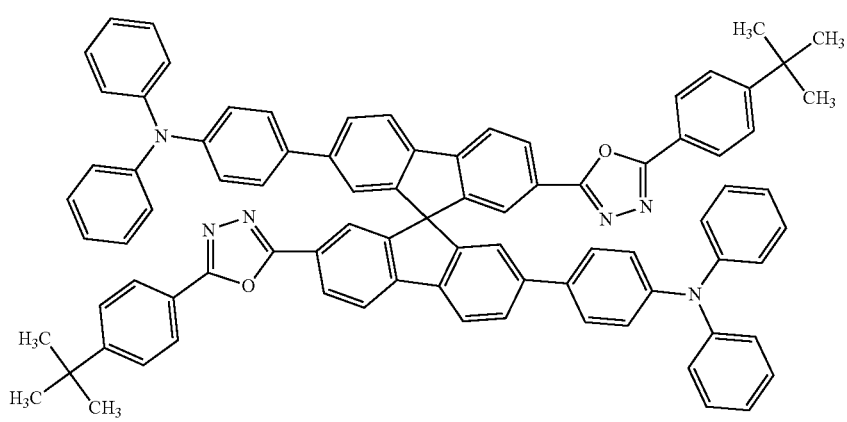
(e16)
[Chemical formula 78]
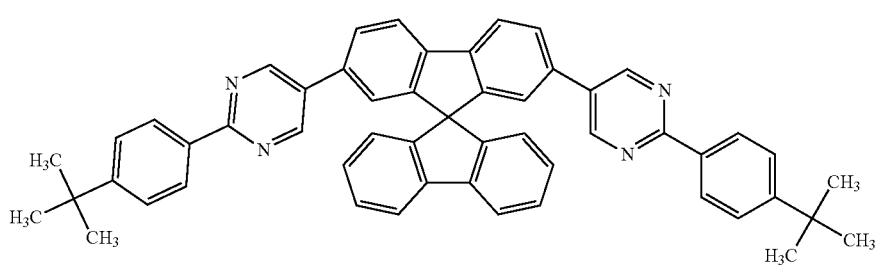
(e17)
[Chemical formula 79]
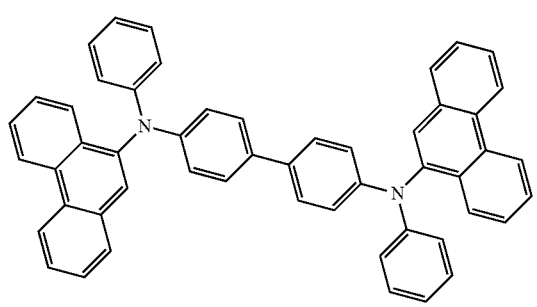
(e18)
[Chemical formula 80]
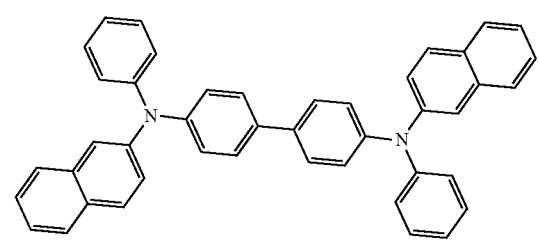
(e19)
[Chemical formula 81]
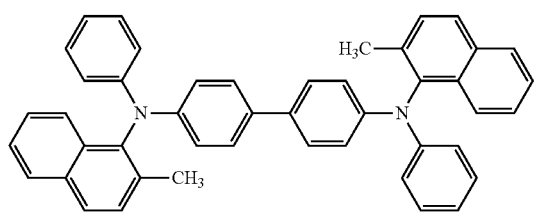
(e110)
[Chemical formula 82]
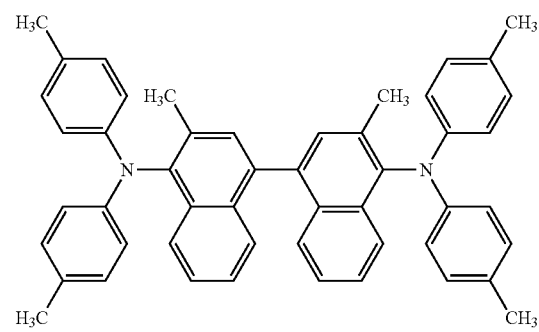
(e111)

-continued
[Chemical 83]
(e112)
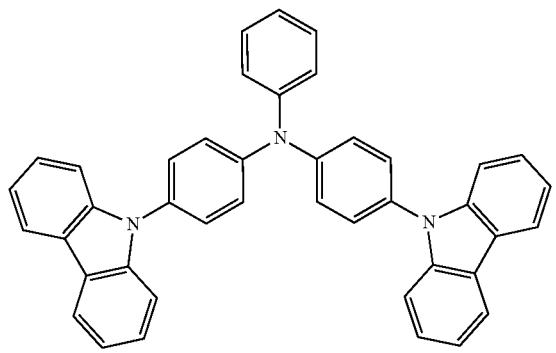
[Chemical 84]
(e113)
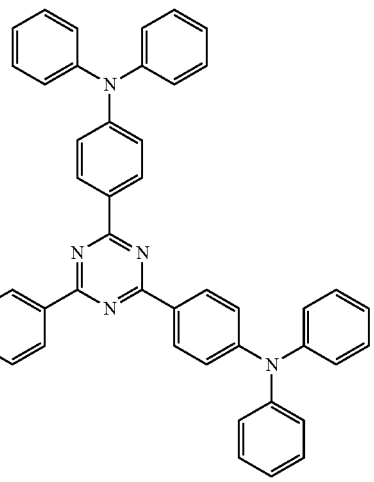
[Chemical 85]
(e114)
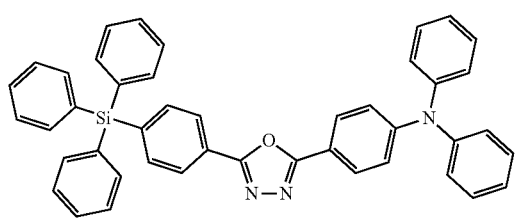
[Chemical 86]
(e115)
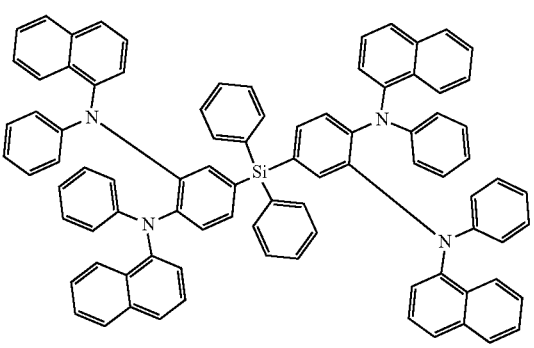
[Chemical 87]
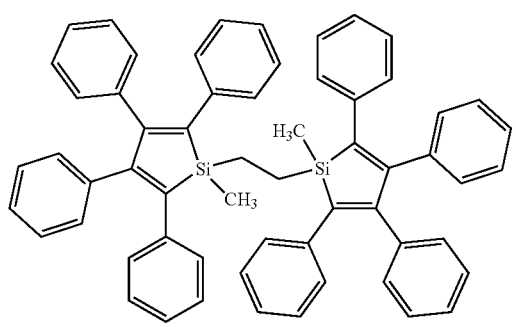
[Chemical 88]
(e116)
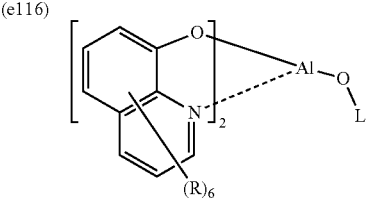
[Chemical 89]
(e118)
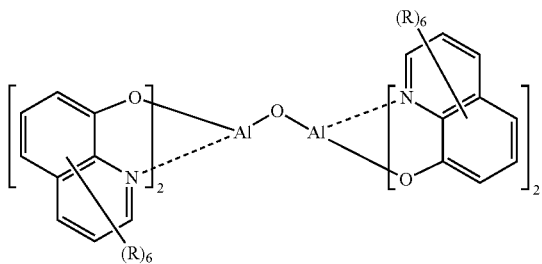
[Chemical 90]
(e119)
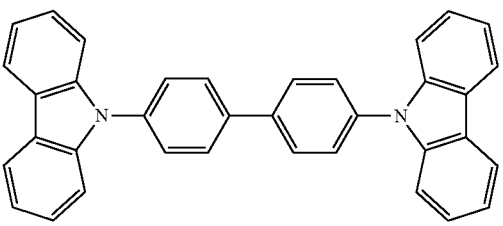

-continued
[Chemical formula 91]
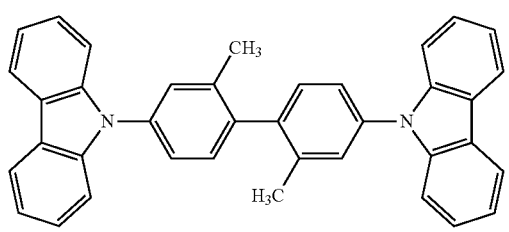
(e120)
[Chemical formula 92]
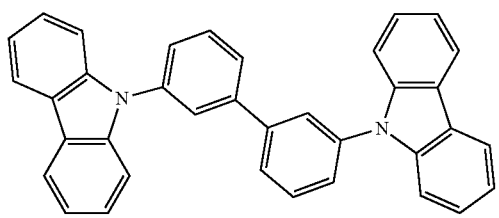
(e121)
[Chemical formula 93]
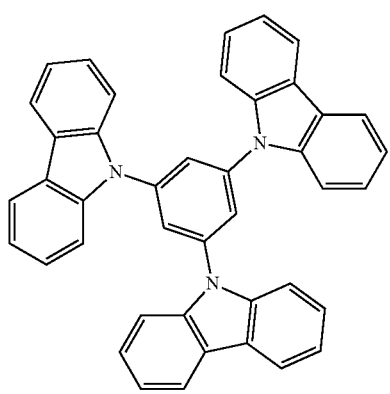
(e122)
[Chemical formula 94]
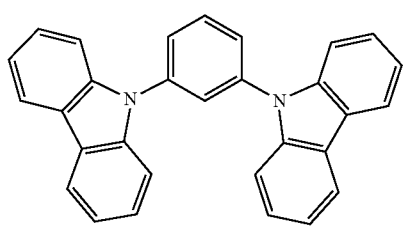
(e123)
[Chemical formula 95]
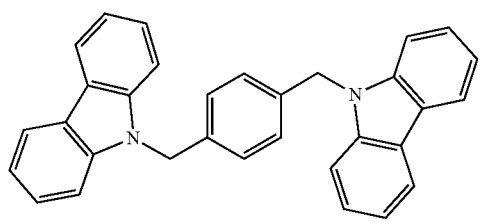
(e124)
[Chemical formula 96]
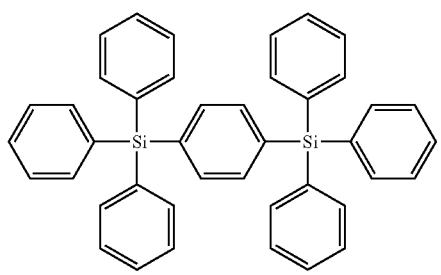
(e125)
[Chemical formula 97]
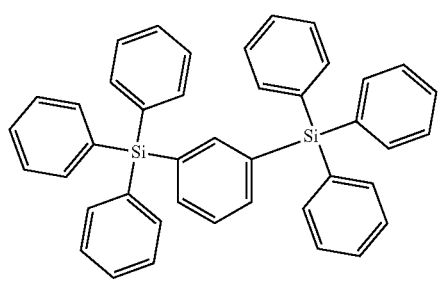
(e126)
[Chemical formula 98]
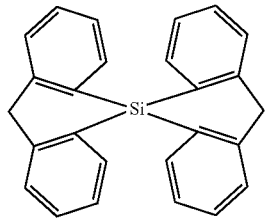
(e127)

[Chemical formula 99]
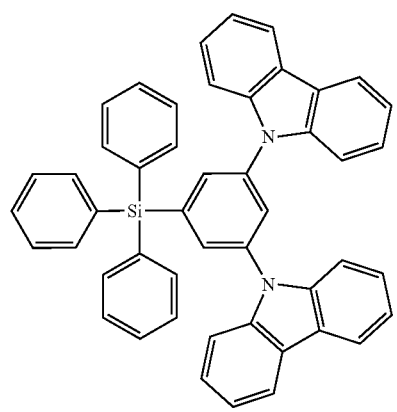
(e128)
[Chemical formula 100]
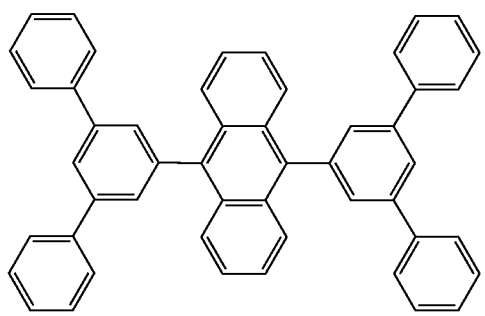
(e129)
[Chemical formula 101]
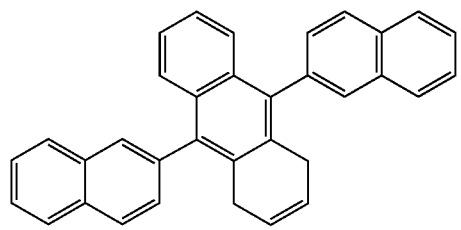
(e130)
[Chemical formula 102]
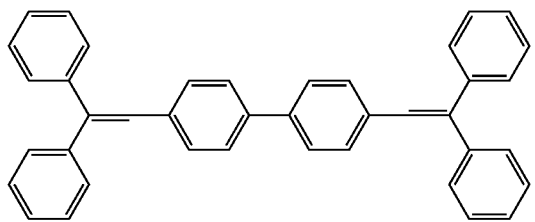
(e131)
[Chemical formula 103]
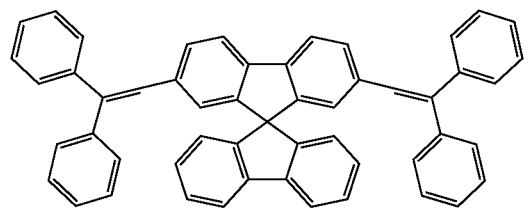
(e132)
[Chemical formula 104]
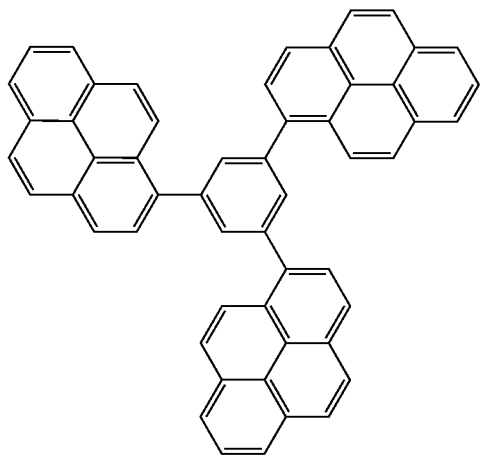
(e133)
[Chemical formula 105]
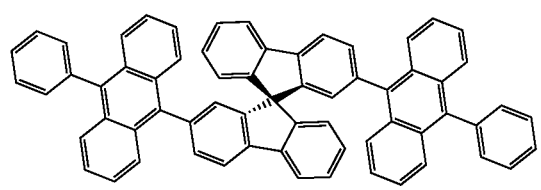
(e134)
[Chemical formula 106]
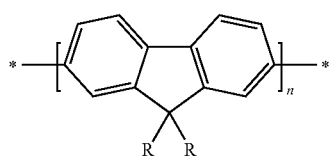
(e135)

[Chemical formula 107]
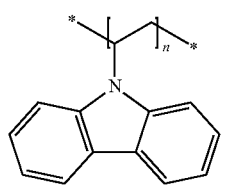
[Chemical formula 108]
(e136)
(e137)
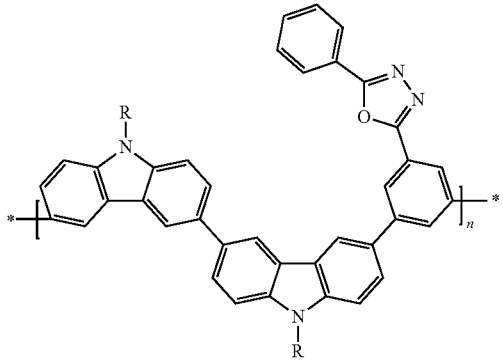
[Chemical formula 109]
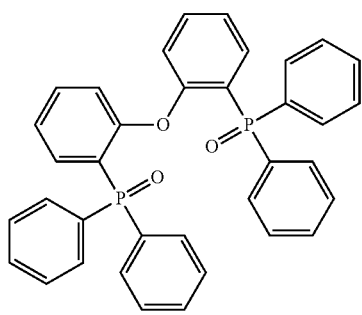
(e138)
[Chemical formula 110]
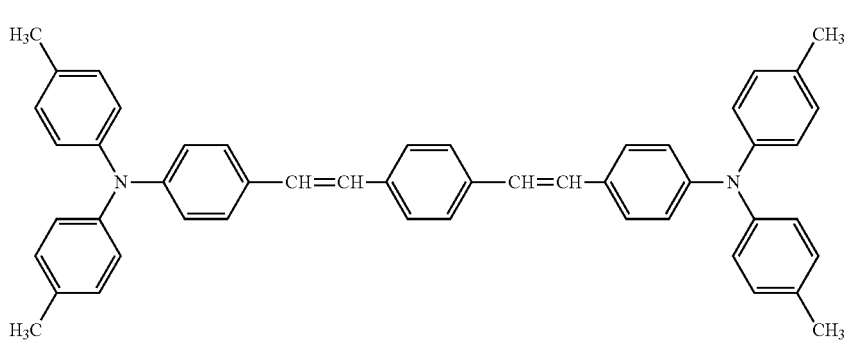
(e139)
[Chemical formula 111]
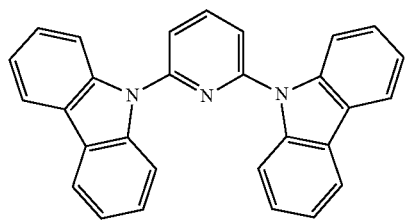
[Chemical formula 112]
(e140)
(e141)
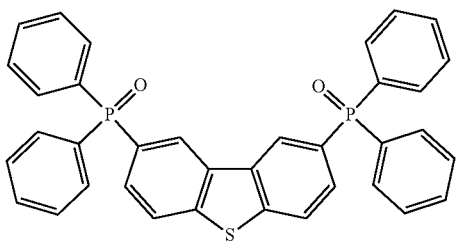

[Chemical formula 113]

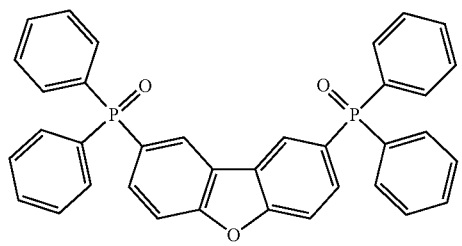

Examples of compounds that can be used as the optionally provided hole-blocking layer include compounds having a hole-blocking action, including compounds having a bipyridyl group and an ortho-terphenyl structure, phenanthroline derivatives such as bathocuproine (hereafter abbreviated as BCP), metal complexes of quinolinol derivatives such as aluminum (III) bis(2-methyl-8-quinolinate)-4-phenylphenolate (hereafter abbreviated as BAlq), various rare earth complexes, oxazole derivatives, triazole derivatives and triazine derivatives. These materials may also function as an electron transport material. These compounds may be used individually, or a combination of two or more compounds may be used. The hole-blocking layer may be a film with a single-layer structure, or a film with a layered structure. These materials may be used to form a thin film by a vapor deposition method or other known methods such as a spin coating method or inkjet method.

Examples of compounds that can be used favorably as the hole-blocking material include compounds (hs1) to (hs11) shown below.

[Chemical formula 114]

(hs1)

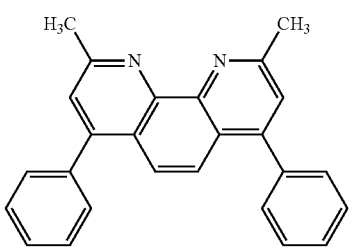

[Chemical formula 115]

(hs2)

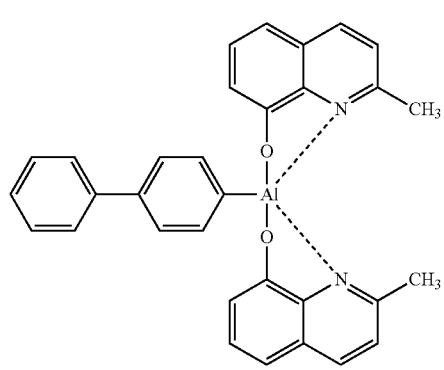

-continued (e142)

-continued

[Chemical formula 116]

(hs3)

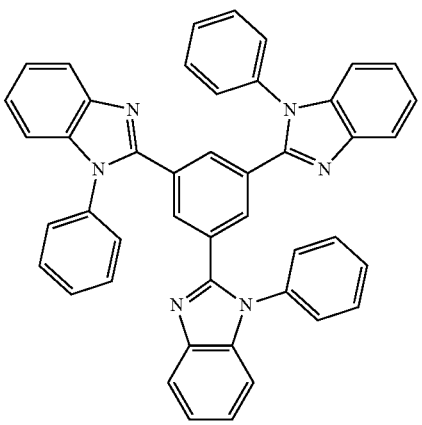

[Chemical formula 117]

(hs4)

-continued

[Chemical formula 118]

(hs5)

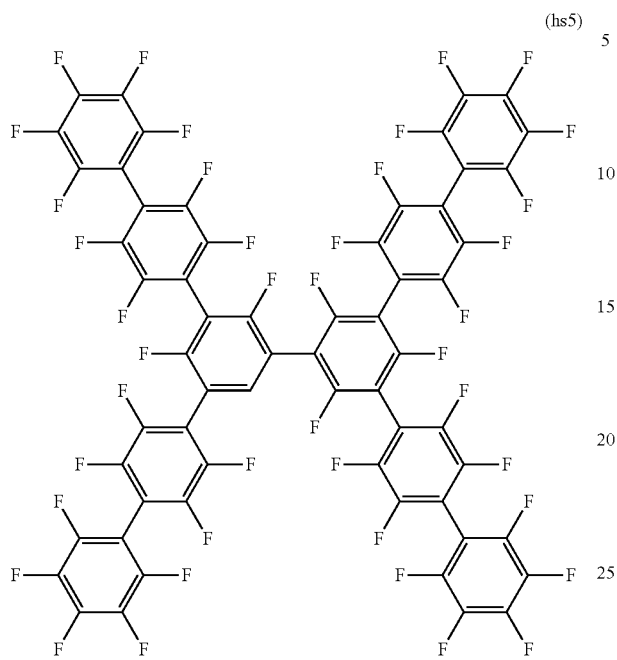

[Chemical formula 119]

(hs6)

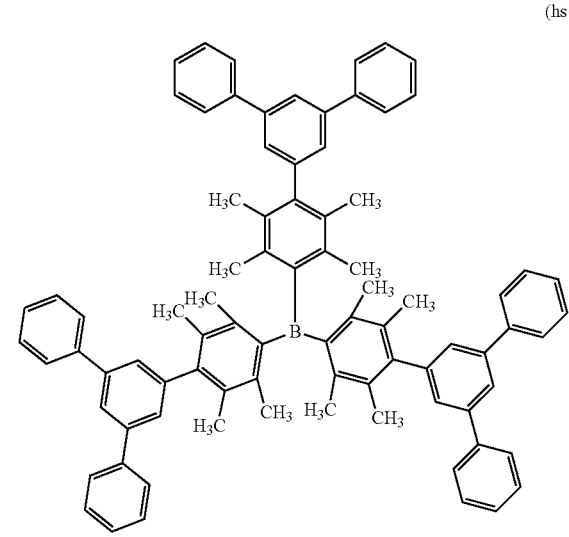

[Chemical formula 120]

(hs7)

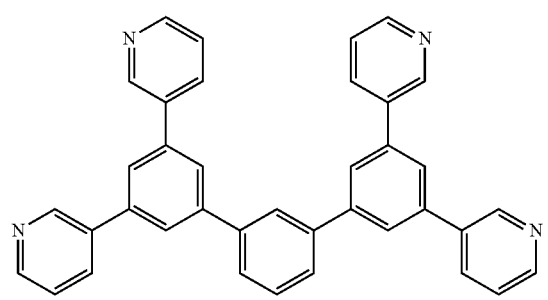

[Chemical formula 121]

(hs8)

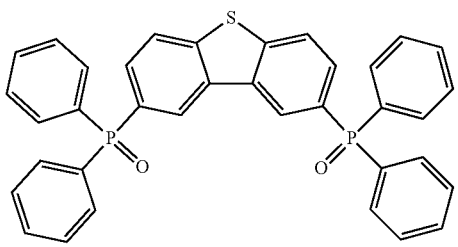

[Chemical formula 122]

(hs9)

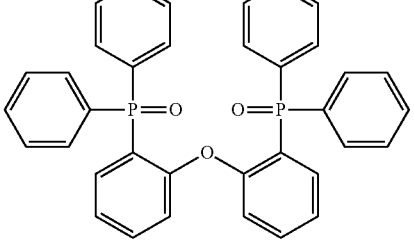

[Chemical formula 123]

(hs10)

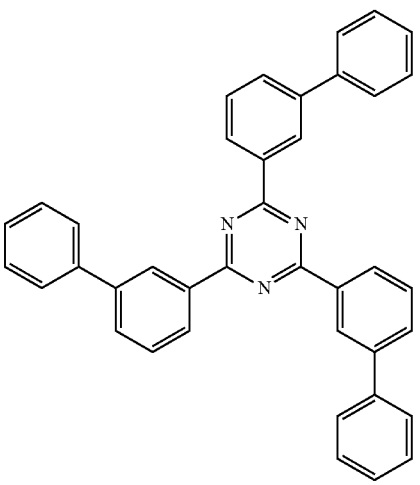

[Chemical formula 124]

(hs11)

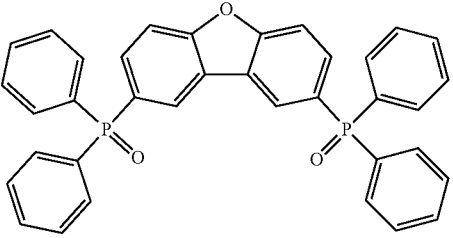

Examples of compounds that can be used as the optionally provided electron transport layer include metal complexes of quinolinol derivatives such as Alq3 and BAlq, as well as various metal complexes, triazole derivatives, triazine derivatives, oxadiazole derivatives, thiadiazole derivatives, carbodiimide derivatives, quinoxaline derivatives, phenanthroline derivatives and silole derivatives. These compounds may be used individually, or a combination of two or more compounds may be used. The electron transport layer may be a film with a single-layer structure, or a film with a multilayered structure. These materials may be used to form a thin film by a vapor deposition method or other known methods such as a spin coating method or inkjet method.

Examples of compounds that can be used as the optionally provided electron injection layer include alkali metal salts such as lithium fluoride and cesium fluoride, alkaline earth metal salts such as magnesium fluoride, and metal oxides (or simply metal oxides) such as aluminum oxide, but in the case of preferred selections for the electron transport layer and the cathode, this layer may be omitted.

In the electron injection layer or the electron transport layer, a material obtained by subjecting a material typically used for the layer to N-doping with a metal such as cesium may also be used.

Examples of compounds that can be used favorably as the electron transport material include compounds (et1) to (et30) shown below.

[Chemical formula 125]

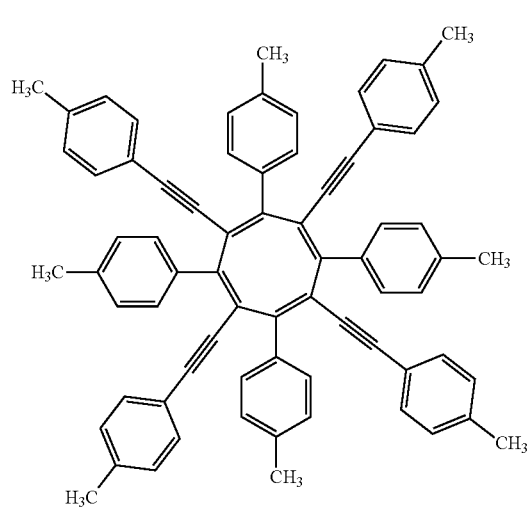

(et1)

[Chemical formula 126]

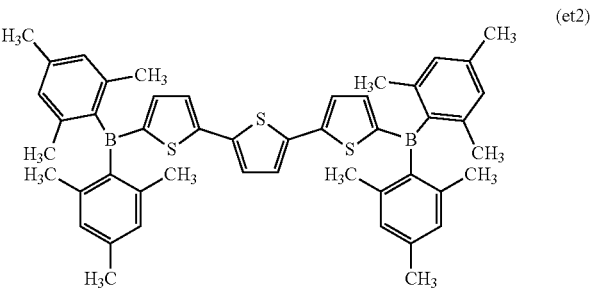

(et2)

[Chemical formula 127]

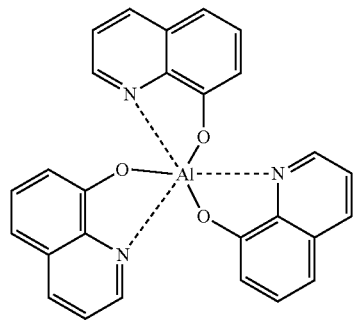

(et3)

[Chemical formula 128]

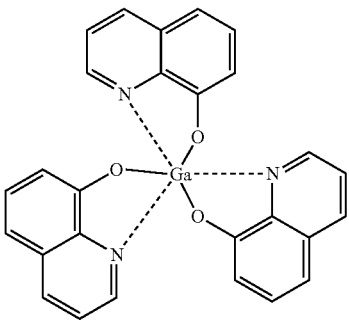

(et4)

[Chemical formula 129]

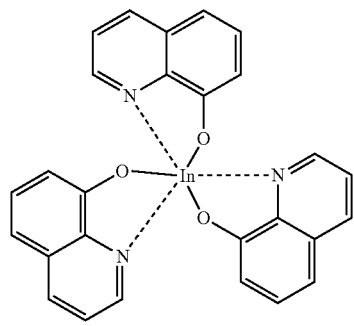

(et5)

[Chemical formula 130]

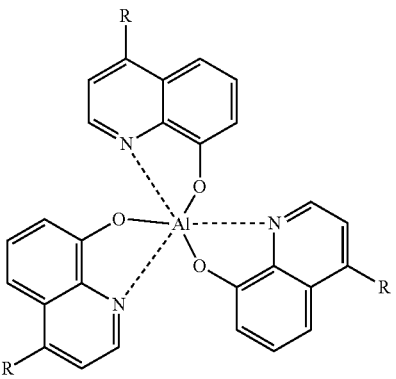

(et6)

-continued
[Chemical formula 131]
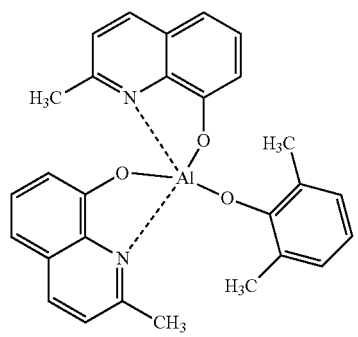
(et7)
[Chemical formula 132]
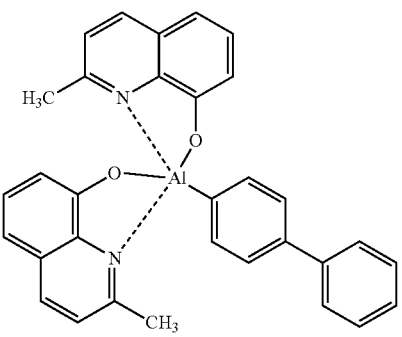
(et8)
[Chemical formula 133]
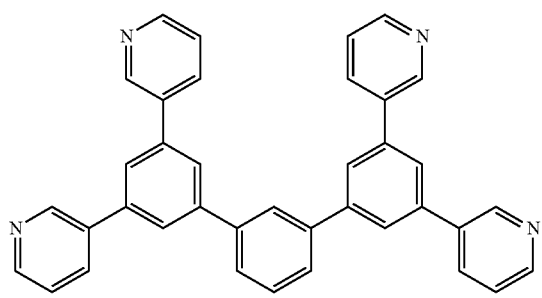
(et9)
[Chemical formula 134]
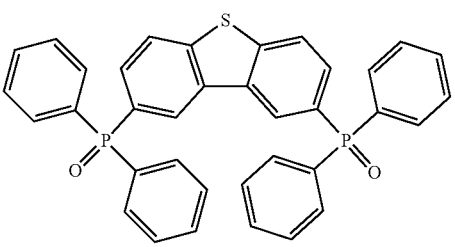
(et10)
[Chemical formula 135]
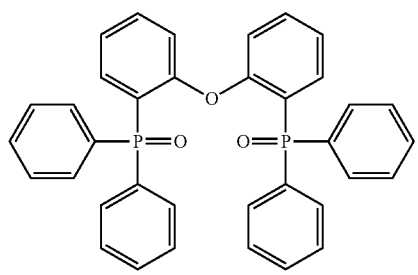
(et11)
[Chemical formula 136]
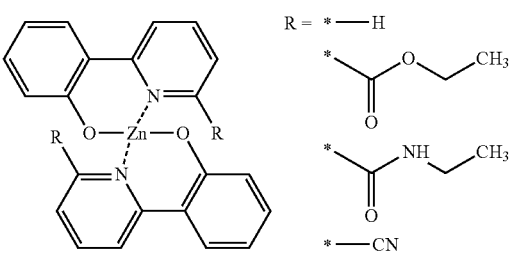
(et12)
[Chemical formula 137]
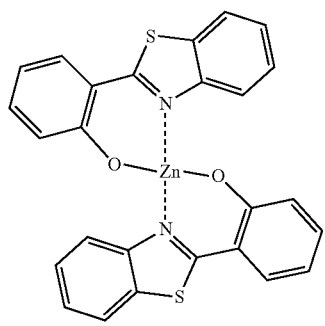
(et13)
[Chemical formula 138]
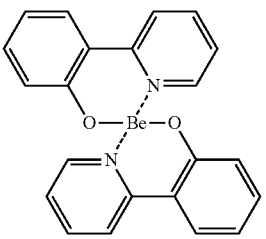
(et14)

[Chemical formula 139]
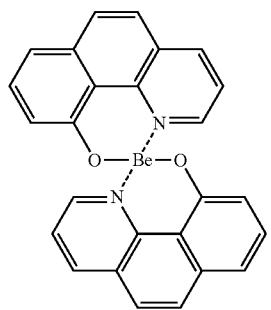
[Chemical formula 140]
(et15)
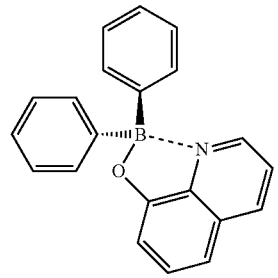
(et16)
[Chemical formula 141]
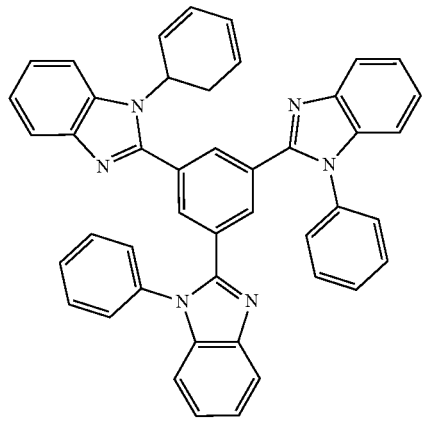
(et17)
[Chemical formula 142]
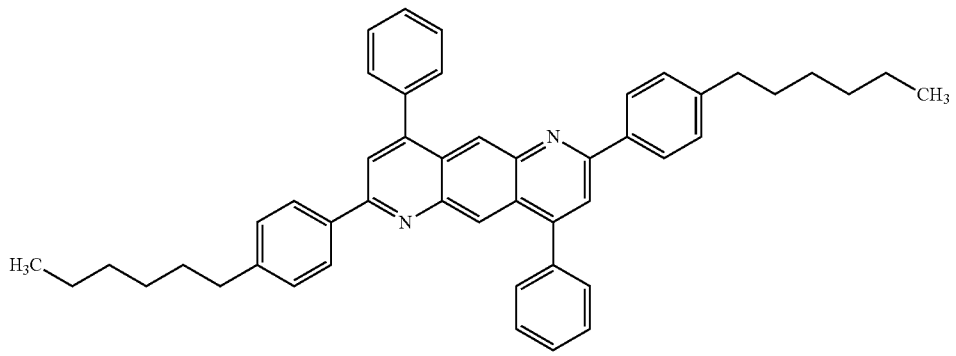
(et18)

[Chemical formula 143]
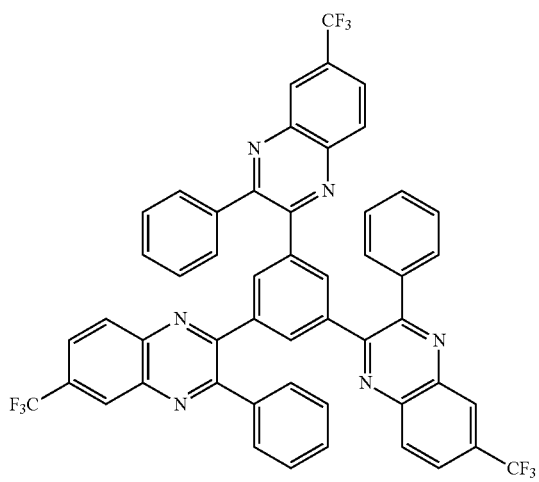
(et19)
[Chemical formula 144]
(et20)
[Chemical formula 145]
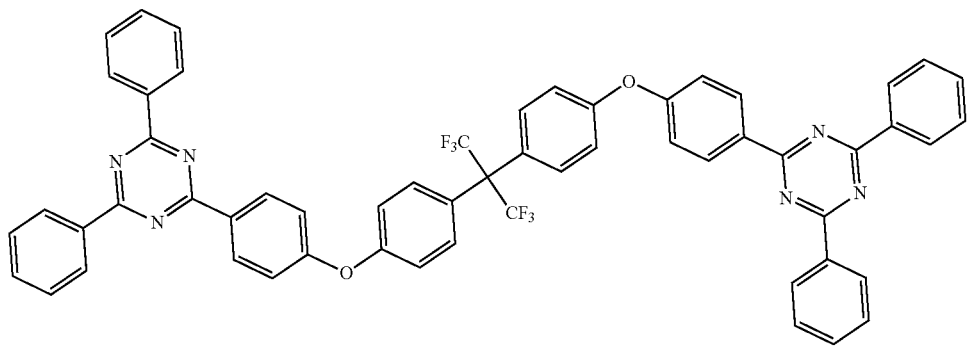
(et21)
[Chemical formula 146]
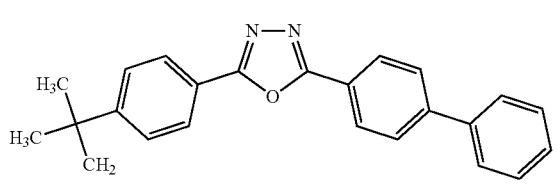
(et22)
[Chemical formula 147]
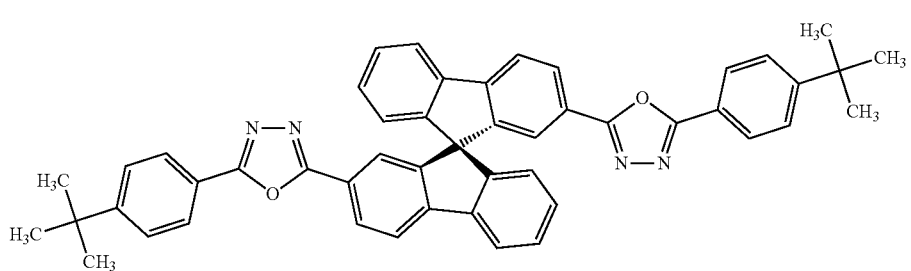
(et23)

[Chemical formula 148]
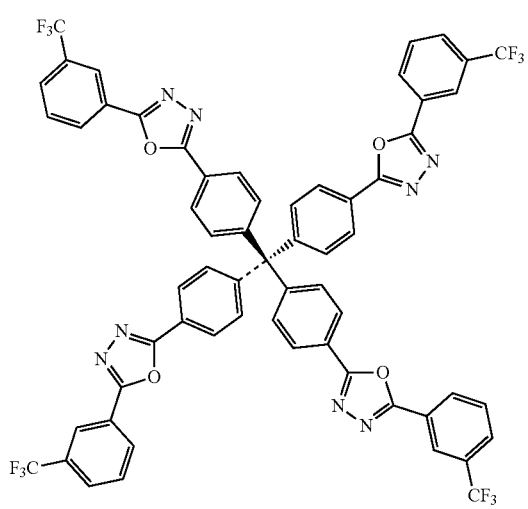
(et24)
[Chemical formula 149]
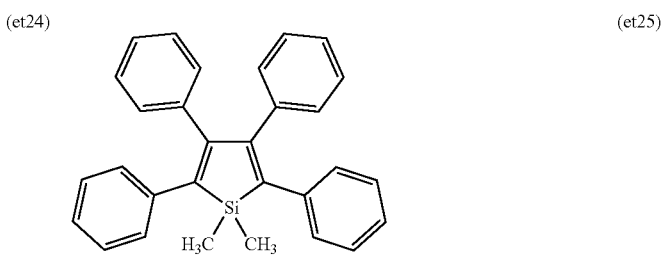
(et25)
[Chemical formula 150]
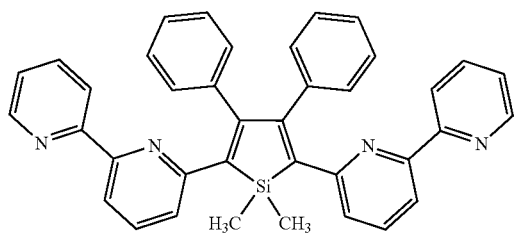
(et26)
[Chemical formula 151]
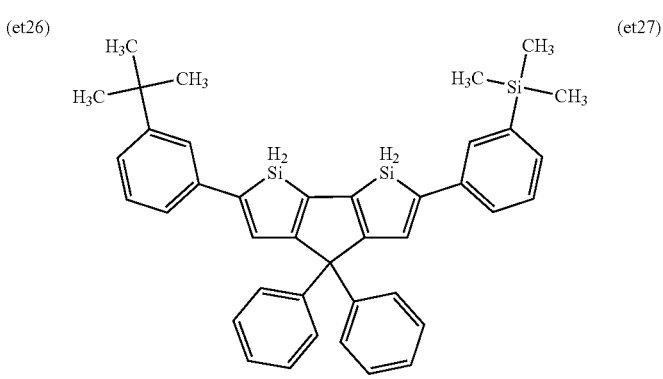
(et27)
[Chemical formula 152]
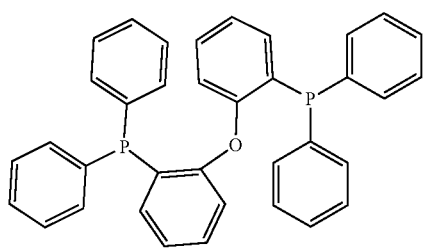
(et28)
[Chemical formula 153]
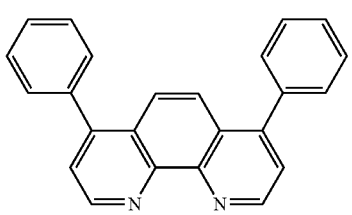
(et29)
[Chemical formula 154]
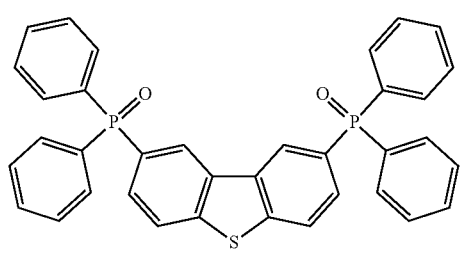
(et30)

Examples of compounds that can be used favorably as the electron injection material include compounds (ei1) to (ei4) shown below.

[Chemical formula 155]

(ei1)

[Chemical formula 156]

(ei2)

[Chemical formula 157]

(ei3)

[Chemical formula 158]

(ei4)

Examples of compounds that can be used favorably as stabilizing materials include compounds (st1) to (st5) shown below.

[Chemical formula 159]

(st1)

[Chemical formula 160]

(st2)

[Chemical formula 161]

(st3)

[Chemical formula 162]

(st4)

[Chemical formula 163]

(st5)

A material having a small work function is generally used for the cathode. Examples of the material for the cathode include sodium, sodium-potassium alloys, lithium, tin, magnesium, magnesium/copper mixtures, magnesium/aluminum mixtures, magnesium/indium mixtures, aluminum/aluminum oxide mixtures, indium, calcium, aluminum, silver, lithium/aluminum mixtures, magnesium-silver alloys, magnesium-indium alloys, and aluminum-magnesium alloys. By using a transparent conductive material, a transparent or semi-transparent cathode can be obtained. The thickness of the cathode is typically within a range from 10 to 5,000 nm, and is preferably from 50 to 200 nm. The sheet resistance of the cathode is preferably at least several hundred Ω/square.

A cathode composed of a low-work function metal is preferably protected by coating with an additional layer of a metal that has a high work function and is stable relative to the external atmosphere such as aluminum, silver, nickel, chromium, gold or platinum, thereby increasing the stability of the element. Further, in order to improve the contact between the cathode and the adjacent organic layer (such as the electron transport layer or electron injection layer), a cathode interface layer may be provided therebetween. Examples of materials that can be used for the cathode interface layer include aromatic diamine compounds, quinacridone compounds, naphthacene compounds, organic silicon compounds, organic phosphorus compounds, compounds having an N-phenylcarbazole skeleton, and N-vinylcarbazole polymers.

The light-emitting element of the present invention may be applied to single elements, structures having elements arranged in an array, and structures having the anode and cathode arranged in an X-Y matrix.

EXAMPLES

Examples of syntheses of compounds of the present invention are presented below, and examples of the effects of those compounds of the present invention are described.

Example 1

Synthesis of 2,4,6-tri(9H-carbazol-9-yl)-3,5-diphenyl-benzonitrile (3Cz-2PBN-A)

[Chemical formula 164]

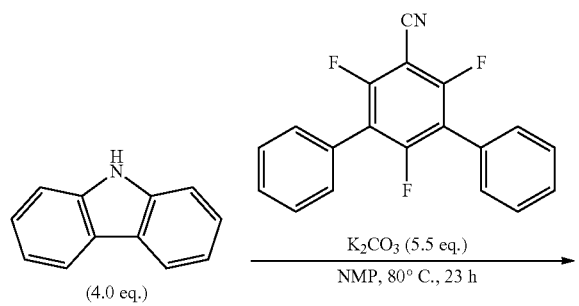

Potassium carbonate (15.36 g, 111.1 mmol) and 9H-carbazole (13.5 g, 80.8 mmol) were added to a 100 mL three-neck flask that had been flushed with nitrogen, 100 mL of anhydrous N-methyl-2-pyrrolidone was then added, and the mixture was stirred for one hour at room temperature. Subsequently, 2,4,6-trifluoro-3,5-diphenylbenzonitrile (6.25 g, 20.2 mmol) was added to the mixture under a stream of nitrogen, and the resulting mixture was stirred at 80° C. for 23 hours. The reaction mixture was then returned to room temperature, methanol was added, and the solid was removed by filtration. Water was then added to the filtrate, and the precipitated crystals were washed with acetone and hexane, and then dried under reduced pressure to obtain a yellow solid of the target product (3Cz-2PBN-A) in a yield of 1.40 g (yield: 9.2%).

$^1$H-NMR (400 MHz, DMSO-$d_6$, δ): 8.07 (d, J=8.0 Hz, 4H), 7.81 to 7.78 (m, 8H), 7.49 (td, J=8.0 Hz, 0.8 Hz, 4H), 7.37 (td, J=7.2 Hz, 0.8 Hz, 2H), 7.23 (t, J=7.6 Hz, 4H), 7.06 (t, J=8.0 Hz, 2H), 6.81 (dd, J=7.2 Hz, 1.2 Hz, 4H), 6.55 (tt, J=7.6 Hz, 1.6 Hz, 2H), 6.44 (t, J=7.6 Hz, 4H)

[Evaluation of Light Emission]

On a glass substrate on which an anode composed of indium-tin oxide (ITO) had been formed with a thickness of 50 nm were sequentially stacked a HAT-CN layer of thickness 10 nm, a TAPC layer of thickness 40 nm, a CCP layer of thickness 10 nm, an mCP layer of thickness 10 nm and a light-emitting layer of thickness 20 nm using vacuum vapor deposition methods (at not more than $5.0 \times 10^{-4}$ Pa).

PPF was used as a host material for the light-emitting layer, and 2,4,6-tri(9H-carbazol-9-yl)-3,5-diphenyl-benzonitrile (3Cz-2PBN-A) was used as a dopant. The dopant concentration was set to 12.0% by weight.

Figure 2:
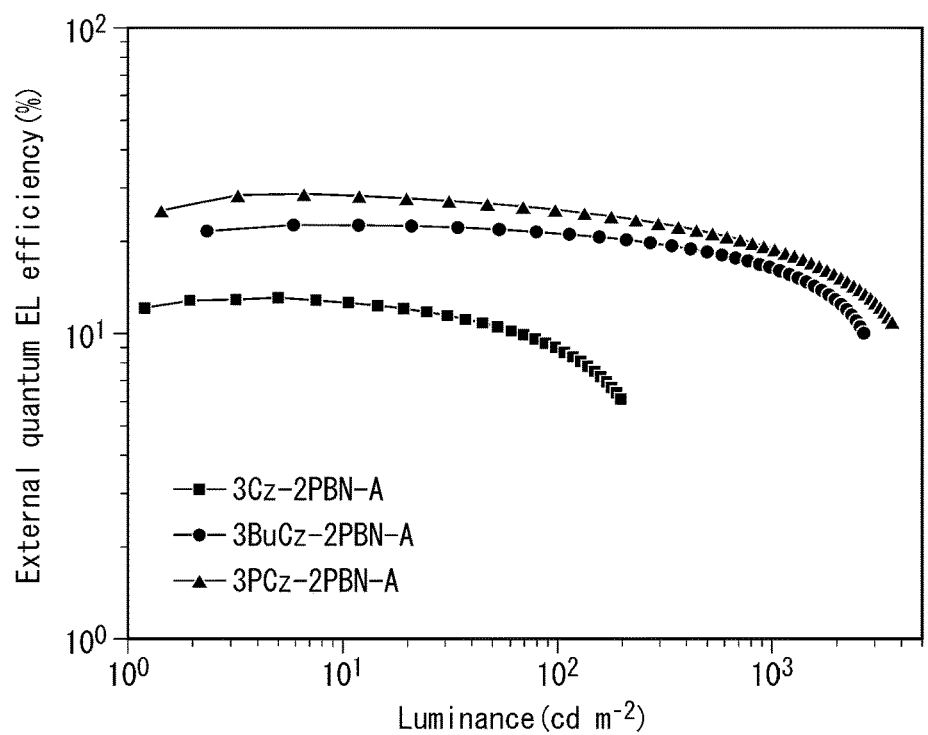
FIG. 2 is a diagram illustrating the luminance-external quantum efficiency characteristics for 3Cz-2PBN-A, 3BuCz-2PBN-A and 3PCz-2PBN-A.

Subsequently, a PPF layer of thickness 10 nm, a B3PyPB layer of thickness 40 nm, an 8-hydroxyquinolinato lithium film of thickness 1 nm and an aluminum film of 100 nm were stacked sequentially by vacuum vapor deposition methods to form a cathode, thus obtaining an organic light-emitting diode (OLED). The results are shown in FIGS. 1 and 2. This organic light-emitting diode had an external quantum efficiency maximum value (EQEmax) of 13.1%.

Example 2

Synthesis of 2,4,6-tri(3,6-diphenyl-9H-carbazol-9-yl)-3,5-diphenyl-benzonitrile (3PCz-2PBN-A)

[Chemical formula 165]

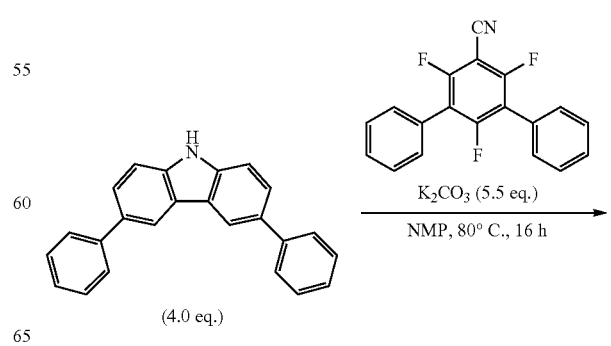

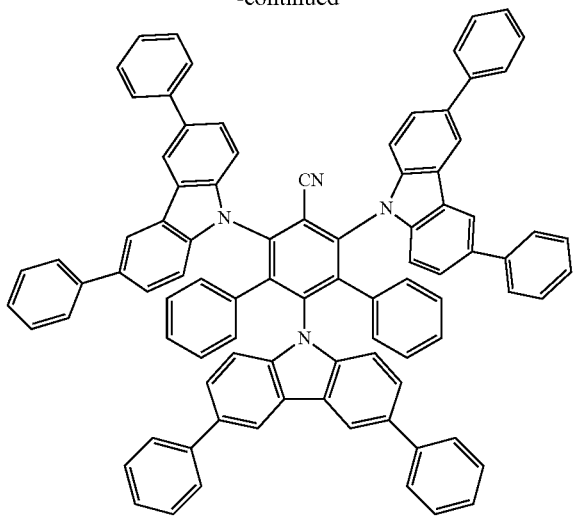

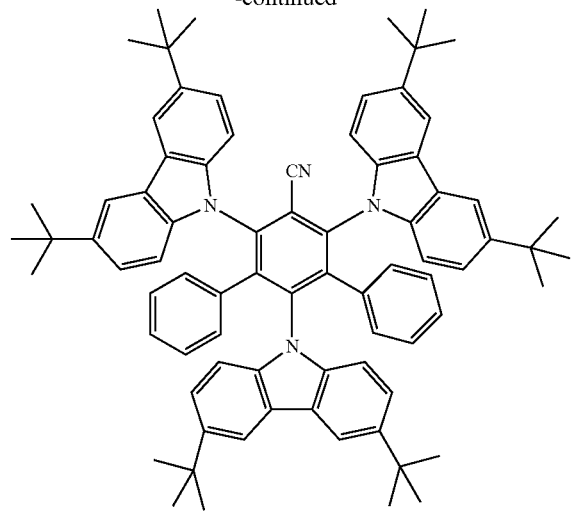

Potassium carbonate (2.50 g, 17.8 mmol) and 3,6-diphenyl-9H-carbazole (4.10 g, 12.9 mmol) were added to a 100 mL three-neck flask that had been flushed with nitrogen, 16.2 mL of anhydrous N-methyl-2-pyrrolidone was then added, and the mixture was stirred for one hour at room temperature. Subsequently, 2,4,6-trifluoro-3,5-diphenylbenzonitrile (1.00 g, 3.23 mmol) was added to the mixture under a stream of nitrogen, and the resulting mixture was stirred at 80° C. for 16 hours. The reaction mixture was then returned to room temperature, methanol was added, and the solid was removed by filtration. Water was then added to the filtrate, and the precipitated crystals were washed with acetone and hexane, and then dried under reduced pressure to obtain a green solid of the target product (3PCz-2PBN-A) in a yield of 1.20 g (yield: 30.8%).

$^1$H-NMR (400 MHz, DMSO-d$_6$, δ): 8.59 (d, J=1.6 Hz, 4H), 8.37 (d, J=2.0 Hz, 2H), 8.02 to 7.99 (m, 6H), 7.87 to 7.75 (m, 18H), 7.52 to 7.45 (m, 12H), 7.37 to 7.30 (m, 6H), 7.03 (dd, J=7.0 Hz, 1.2 Hz, 4H), 6.66 to 6.58 (m, 6H)

[Evaluation of Light Emission]

With the exception of altering the dopant to 2,4,6-tri(3,6-diphenyl-9H-carbazol-9-yl)-3,5-diphenyl-benzonitrile (3PCz-2PBN-A), a light emission evaluation was conducted using the same method as Example 1. The results are shown in FIGS. 1 and 2. EQEmax was 28.1%.

Example 3

Synthesis of 2,4,6-tri(3,6-di-t-butyl-9H-carbazol-9-yl)-3,5-diphenyl-benzonitrile (3BuCz-2PBN-A)

[Chemical formula 166]

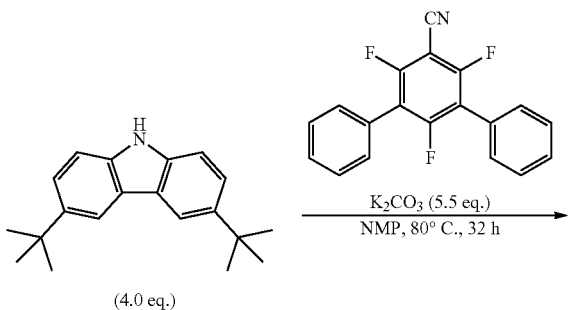

Potassium carbonate (2.83 g, 20.5 mmol) and 3,6-di-t-butyl-carbazole (4.16 g, 14.9 mmol) were added to a 100 mL three-neck flask that had been flushed with nitrogen, 20 mL of anhydrous N-methyl-2-pyrrolidone was then added, and the mixture was stirred for one hour at room temperature. Subsequently, 2,4,6-trifluoro-3,5-diphenylbenzonitrile (1.15 g, 3.72 mmol) was added to the mixture under a stream of nitrogen, and the resulting mixture was stirred at 80° C. for 32 hours. The reaction mixture was then returned to room temperature, methanol was added, and the solid was removed by filtration. Water was then added to the filtrate, the precipitated crystals were dissolved in chloroform, and the solution was washed with water. Subsequently, the solution was dried over magnesium sulfate and then concentrated. The concentrate was then purified by silica gel column chromatography (n-hexane/ethyl acetate=19/1) to obtain a light yellow solid of the target product (3BuCz-2PBN-A) in a yield of 1.20 g (yield: 29.7%).

$^1$H-NMR (400 MHz, CDCl$_3$, δ): 7.94 (d, J=2.0 Hz, 4H), 7.73 (d, J=1.6 Hz, 2H), 7.42 (dd, J=8.8 Hz, 1.6 Hz, 4H), 7.27 (dd, J=8.6 Hz, 2.0 Hz, 4H), 7.13 (d, J=8 Hz, 4H), 6.98 (d, J=8.8 Hz, 2H), 6.63 (d, J=7.8 Hz, 4H), 6.50 (t, J=6.4 Hz, 2H), 6.38 (t, J=7.6 Hz, 4H), 1.39 (s, 36H), 1.31 (s, 18H)

[Evaluation of Light Emission]

With the exception of altering the dopant to 2,4,6-tri(3,6-di-t-butyl-9H-carbazol-9-yl)-3,5-diphenyl-benzonitrile (3BuCz-2PBN-A), a light emission evaluation was conducted using the same method as Example 1. The results are shown in FIGS. 1 and 2. EQEmax was 22.6%.

When Example 1, Example 2 and Example 3 which had the same 2,3-phenyl-substituted skeleton were compared, it was evident that the compounds of the present invention (Example 2 and Example 3) exhibited a relatively higher EQEmax, and were useful as light-emitting materials.

Example 4

Synthesis of 2,3,5-tri(9H-carbazol-9-yl)-4,6-diphenyl-benzonitrile (3Cz-2PBN-B)

[Chemical formula 167]

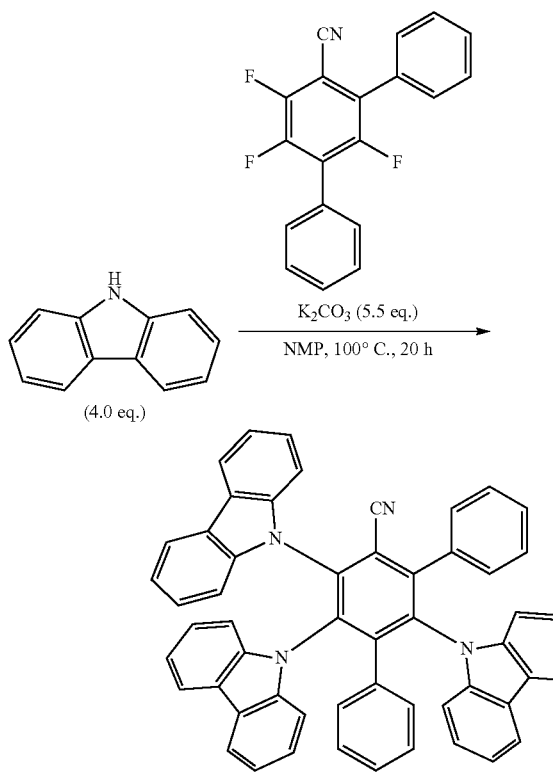

Potassium carbonate (2.76 g, 20.0 mmol) and 9H-carbazole (2.42 g, 14.5 mmol) were added to a 100 mL three-neck flask that had been flushed with nitrogen, 18 mL of anhydrous N-methyl-2-pyrrolidone was then added, and the mixture was stirred for one hour at room temperature. Subsequently, a solution obtained by dissolving 2,3,5-trifluoro-4,6-diphenylbenzonitrile (1.12 g, 3.6 mmol) in 18 mL of anhydrous N-methyl-2-pyrrolidone was added to the mixture under a stream of nitrogen, and the resulting mixture was stirred at 100° C. for 20 hours. The reaction mixture was then returned to room temperature, water and ethyl acetate were added, and the organic layer was separated. The water layer was extracted twice with ethyl acetate, and the combined organic layer was washed three times with water, and then twice with a saturated saline solution. The organic layer was dried over magnesium sulfate and filtered, and the filtrate was then concentrated to obtain a crude product. The crude product was purified by silica gel column chromatography (eluent: n-hexane/ethyl acetate) to obtain a crudely purified product. Acetone/n-hexane were then added to this crudely purified product, and the mixture was subjected to ultrasonic irradiation. Subsequently, the mixture was filtered and washed with n-hexane to obtain a light yellow solid of the target product (3Cz-2PBN-B) in a yield of 2.46 g (yield: 90.5%).

$^1$H-NMR (400 MHz, DMSO-$d_6$, δ): 7.88 (d, J=8.0 Hz, 2H), 7.85 (d, J=8.0 Hz, 2H), 7.82 (d, J=8.0 Hz, 2H), 7.80 (d, J=8.0 Hz, 2H), 7.64 (d, J=8.4 Hz, 2H), 7.60 (d, J=7.6 Hz, 2H), 7.41 to 7.37 (m, 2H), 7.35 to 7.32 (m, 2H), 7.25 to 7.21 (m, 2H), 7.12 to 7.03 (m, 9H), 6.89 (t, J=7.6 Hz, 2H), 6.68 (d, J=7.2 Hz, 2H), 6.42 (t, J=7.6 Hz, 1H), 6.27 (t, J=7.6 Hz, 2H)

[Evaluation of Light Emission]

Figure 3:
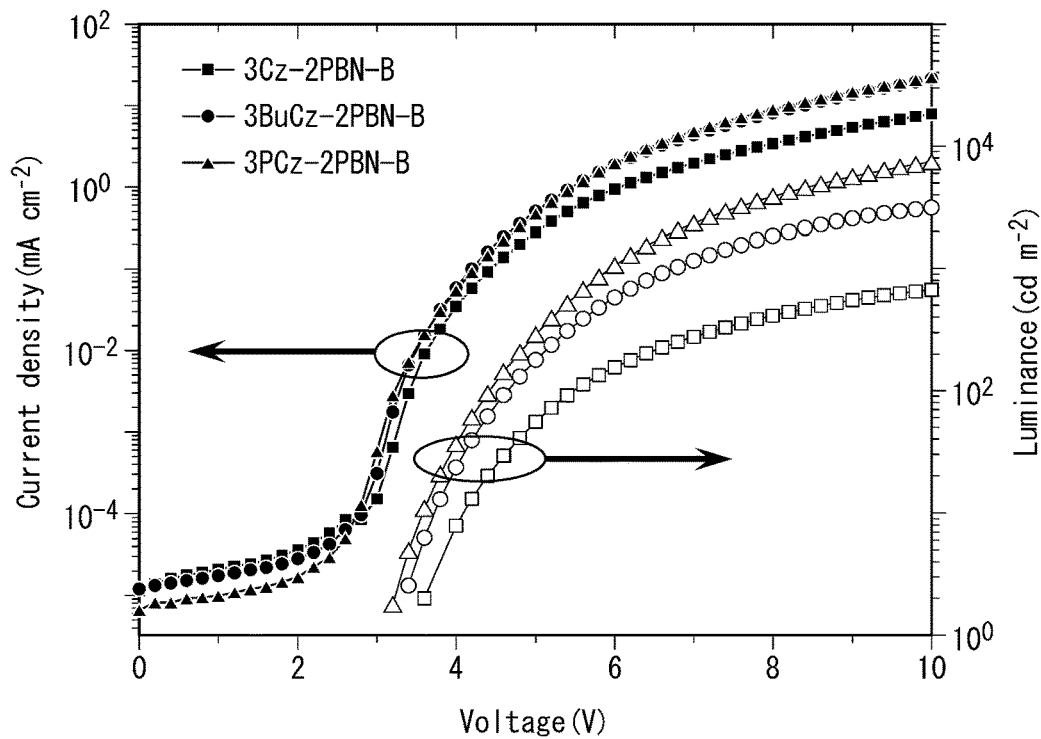
FIG. 3 is a diagram illustrating the voltage-current density-luminance characteristics for 3Cz-2PBN-B, 3BuCz-2PBN-B and 3PCz-2PBN-B.
Figure 4:
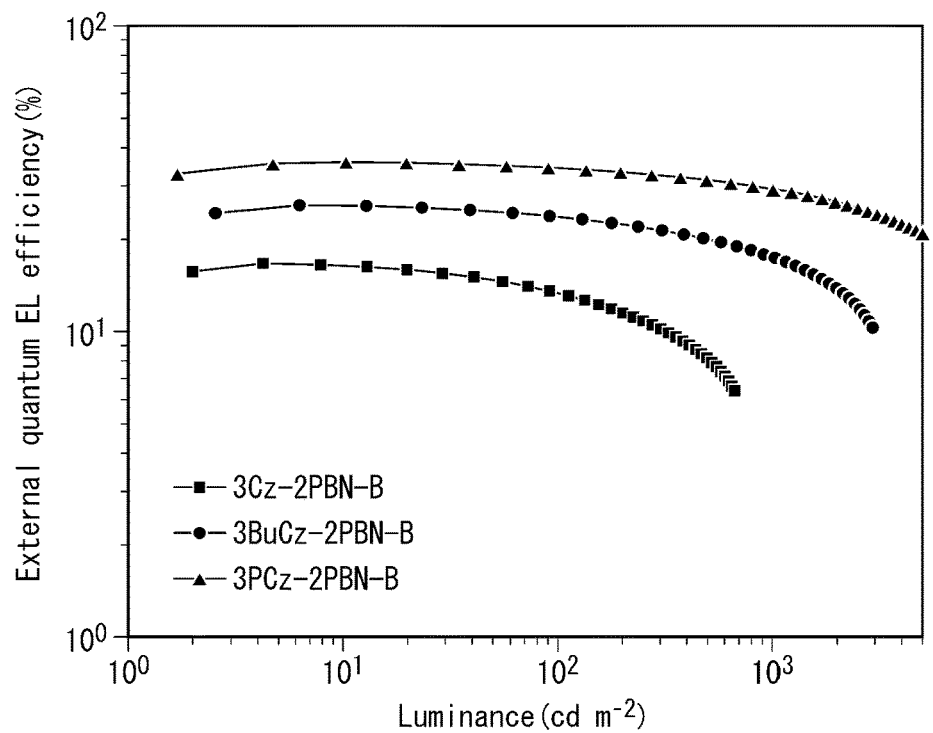
FIG. 4 is a diagram illustrating the luminance-external quantum efficiency characteristics for 3Cz-2PBN-B, 3BuCz-2PBN-B and 3PCz-2PBN-B.

With the exception of altering the dopant to 2,3,5-tri(9H-carbazol-9-yl)-4,6-diphenyl-benzonitrile (3Cz-2PBN-B), a light emission evaluation was conducted using the same method as Example 1. The results are shown in FIGS. 3 and 4. EQEmax was 16.7%.

Example 5

Synthesis of 2,3,5-tri(3,6-diphenyl-9H-carbazol-9-yl)-4,6-diphenyl-benzonitrile (3PCz-2PBN-B)

[Chemical formula 168]

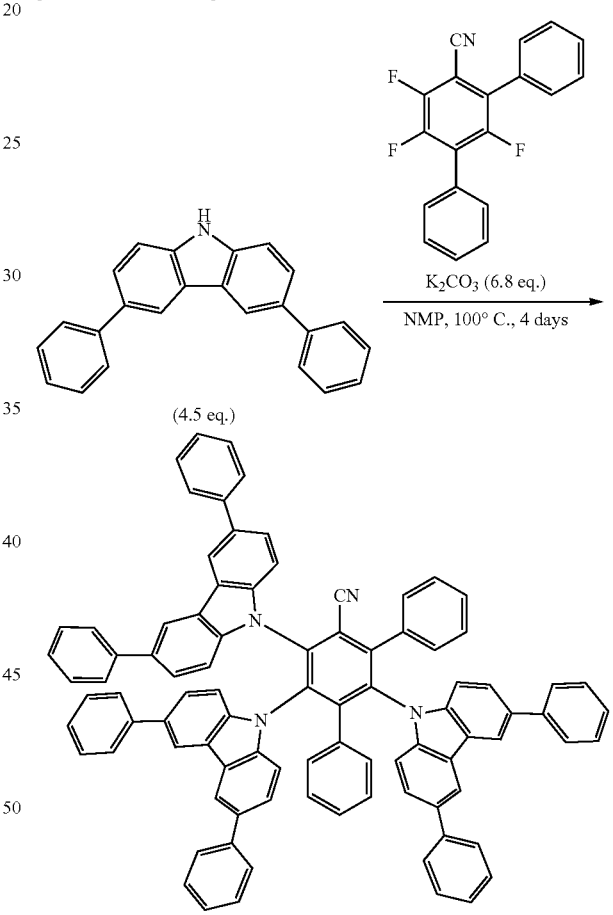

Potassium carbonate (0.74 g, 5.4 mmol) and 3,6-diphenyl-9H-carbazole (1.12 g, 3.5 mmol) were added to a 100 mL three-neck flask that had been flushed with nitrogen, 8.0 mL of anhydrous N-methyl-2-pyrrolidone was then added, and the mixture was stirred for one hour at room temperature. Subsequently, 2,3,5-trifluoro-4,6-diphenylbenzonitrile (0.24 g, 0.8 mmol) was added to the mixture under a stream of nitrogen, and the resulting mixture was stirred at 100° C. for 4 days. The reaction mixture was then returned to room temperature, water and ethyl acetate were added, and the organic layer was separated. The water layer was extracted twice with ethyl acetate, and the combined organic layer was washed three times with water, and then twice with a saturated saline solution. The organic layer was dried over magnesium sulfate and filtered, and the filtrate was then concentrated to obtain a crude product. The crude product was purified by silica gel column chromatography (eluent: n-hexane/dichloromethane) to obtain a crudely purified product. Dichloromethane/diethyl ether/n-hexane were then added to this crudely purified product, and the mixture was subjected to ultrasonic irradiation. Subsequently, the mixture was filtered and washed with n-hexane to obtain a yellow solid of the target product (3PCz-2PBN-B) in a yield of 0.90 g (yield: 96.1%).

$^1$H-NMR (400 MHz, DMSO-d$_6$, δ): 8.44 (d, J=2.0 Hz, 2H), 8.27 (d, J=1.6 Hz, 2H), 8.05 (d, J=1.6 Hz, 2H), 8.00 (d, J=8.8 Hz, 2H), 7.89 (d, J=8.8 Hz, 2H), 7.82 to 7.79 (m, 6H), 7.73 (d, J=8.8 Hz, 2H), 7.63 (d, J=7.6 Hz, 4H), 7.56 (d, J=7.2 Hz, 4H), 7.53 to 7.47 (m, 8H), 7.43 to 7.26 (m, 16H), 7.19 to 7.15 (m, 3H), 6.97 (d, J=7.2 Hz, 2H), 6.58 to 6.48 (m, 3H)

[Evaluation of Light Emission]

With the exception of altering the dopant to 2,3,5-tri(3,6-diphenyl-9H-carbazol-9-yl)-4,6-diphenyl-benzonitrile (3PCz-2PBN-B), a light emission evaluation was conducted using the same method as Example 1. The results are shown in FIGS. 3 and 4. EQEmax was 35.1%.

Example 6

Synthesis of 2,3,5-tri(3,6-di-t-butyl-9H-carbazol-9-yl)-4,6-diphenyl-benzonitrile (3BuCz-2PBN-B)

[Chemical formula 169]

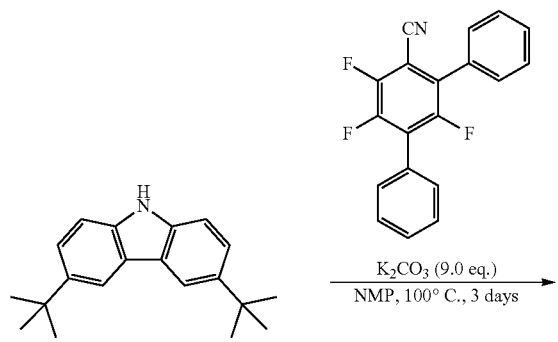

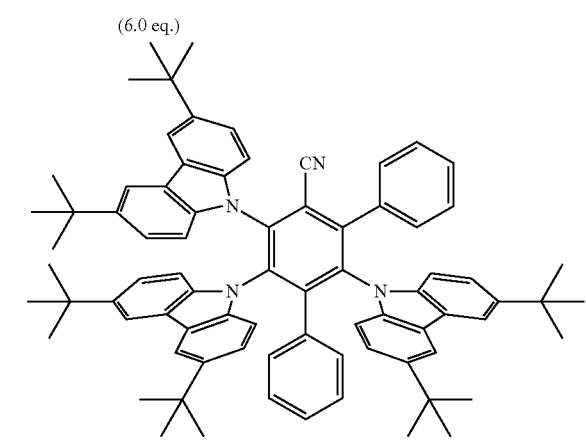

Potassium carbonate (4.04 g, 29.2 mmol) and 3,6-diphenyl-9H-carbazole (5.47 g, 19.6 mmol) were added to a 200 mL three-neck flask that had been flushed with nitrogen, 32.0 mL of anhydrous N-methyl-2-pyrrolidone was then added, and the mixture was stirred for one hour at room temperature. Subsequently, 2,3,5-trifluoro-4,6-diphenylbenzonitrile (1.00 g, 3.2 mmol) was added to the mixture under a stream of nitrogen, and the resulting mixture was stirred at 100° C. for 3 days. The reaction mixture was then returned to room temperature, water and ethyl acetate were added, and the organic layer was separated. The water layer was extracted twice with ethyl acetate, and the combined organic layer was washed three times with water, and then twice with a saturated saline solution. The organic layer was dried over magnesium sulfate and filtered, and the filtrate was then concentrated to obtain a crude product. The crude product was purified by silica gel column chromatography (eluent: n-hexane/dichloromethane) to obtain a crudely purified product. Subsequently, n-hexane was added to this crudely purified product, and the mixture was subjected to ultrasonic irradiation. The mixture was then filtered and washed with n-hexane to obtain a light yellow-white solid of the target product (3BuCz-2PBN-B) in a yield of 2.79 g (yield: 79.3%).

$^1$H-NMR (400 MHz, DMSO-d$_6$, δ): 7.90 (d, J=2.0 Hz, 2H), 7.74 (d, J=2.0 Hz, 2H), 7.58 (d, J=8.8 Hz, 2H), 7.50 (d, J=1.6 Hz, 2H), 7.39 (td, J=8.8 Hz, 2.0 Hz, 4H), 7.27 (d, J=8.4 Hz, 2H), 7.18 (d, J=8.8 Hz, 2H), 7.11 to 7.05 (m, 5H), 6.97 (dd, J=8.8 Hz, 2.0 Hz, 2H), 6.78 (d, J=7.2 Hz, 2H), 6.47 (t, J=8.0 Hz, 1H), 6.36 (t, J=8.0 Hz, 2H), 1.35 (s, 18H), 1.31 (s, 18H), 1.22 (s, 18H)

[Evaluation of Light Emission]

With the exception of altering the dopant to 2,3,5-tri(3,6-di-t-butyl-9H-carbazol-9-yl)-4,6-diphenyl-benzonitrile (3BuCz-2PBN-B), a light emission evaluation was conducted using the same method as Example 1. The results are shown in FIGS. 3 and 4. EQEmax was 24.4%.

When Example 4, Example 5 and Example 6 which had the same 1,4-phenyl-substituted skeleton were compared, it was evident that the compounds of the present invention (Example 5 and Example 6) exhibited a relatively higher EQEmax, and were useful as light-emitting materials.

Example 7

Synthesis of 2,3,5,6-tetra(3,6-di-t-butyl-9H-carbazol-9-yl)-4-phenyl-benzonitrile (4BuCz-1PBN-A)

[Chemical formula 170]

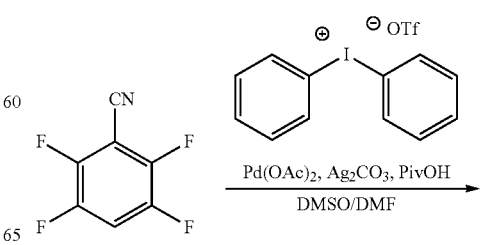

-continued

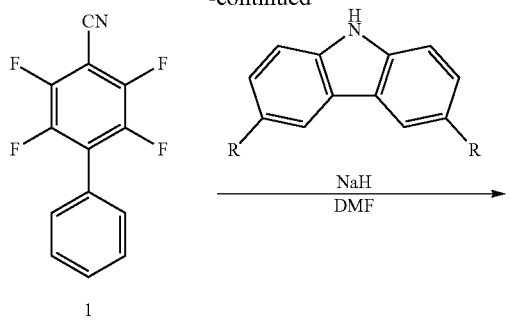

1

2 (R = t-Bu)

A flask that had been flushed with nitrogen was charged with palladium(II) acetate (0.64 g, 2.85 mmol), silver carbonate (15.8 g, 57.3 mmol) and diphenyliodonium trifluoromethanesulfonate (16.0 g, 37.2 mmol), and the mixture was degassed three times. Subsequently, 2,3,5,6-tetrafluorobenzonitrile (5.0 g, 28.6 mmol), pivalic acid (2.92 g, 28.6 mmol), dimethyl sulfoxide (2 mL) and N,N-dimethylformamide (40 mL) were added, and the resulting mixture was stirred at 130° C. for 10 hours. Subsequently, the reaction mixture was returned to room temperature, and impurities were removed using celite. The reaction mixture was then extracted into ethyl acetate. The organic layer was dried by adding sodium sulfate and then purified by column chromatography (ethyl acetate:hexane=1:9) to obtain a white solid of a compound 1 (2.94 g, 41%).

$^1$H-NMR (400 MHz, CDCl$_3$): δ 7.56 to 7.52 (m, 3H), 7.48 to 7.45 (m, 2H)

A flask that had been flushed with nitrogen was charged with 3,6-di-tert-butylcarbazole (1.37 g, 4.90 mmol) and N,N-dimethylformamide (10 mL). Subsequently, N,N-dimethylformamide (5 mL) to which potassium tert-butoxide (0.55 g, 4.90 mmol) had been added was added to the flask at room temperature, and the resulting mixture was stirred at room temperature for 30 minutes. N,N-dimethylformamide (10 mL) to which the compound 1 (0.3 g, 1.19 mmol) had been added was then added dropwise to the flask over a period of 10 minutes. Subsequently, the reaction mixture was stirred at 80° C. for 10 hours. The reaction mixture was then returned to room temperature, water (20 mL) was added, and after 30 minutes had elapsed, the mixture was extracted into chloroform. The organic layer was dried by adding sodium sulfate and then purified by column chromatography (ethyl acetate:hexane=1:9) to obtain a yellow solid of a compound 2 (4BuCz-1PBN-A) (1.32 g, 86%).

$^1$H-NMR (400 MHz, DMSO-d$_6$): δ 7.76 (d, J=1.2 Hz, 4H), 7.56 (d, J=1.2 Hz, 4H), 7.46 (d, J=8.4 Hz, 4H), 7.42 (d, J=8.8 Hz, 4H), 7.09 (dd, J=8.8 Hz, 1.2 Hz, 6H), 7.02 (dd, J=8.4 Hz, 1.6 Hz, 4H), 6.60 to 6.57 (m, 3H), 1.32 (s, 36H), 1.26 (s, 36H)

[Evaluation of Light Emission]

Figure 5:
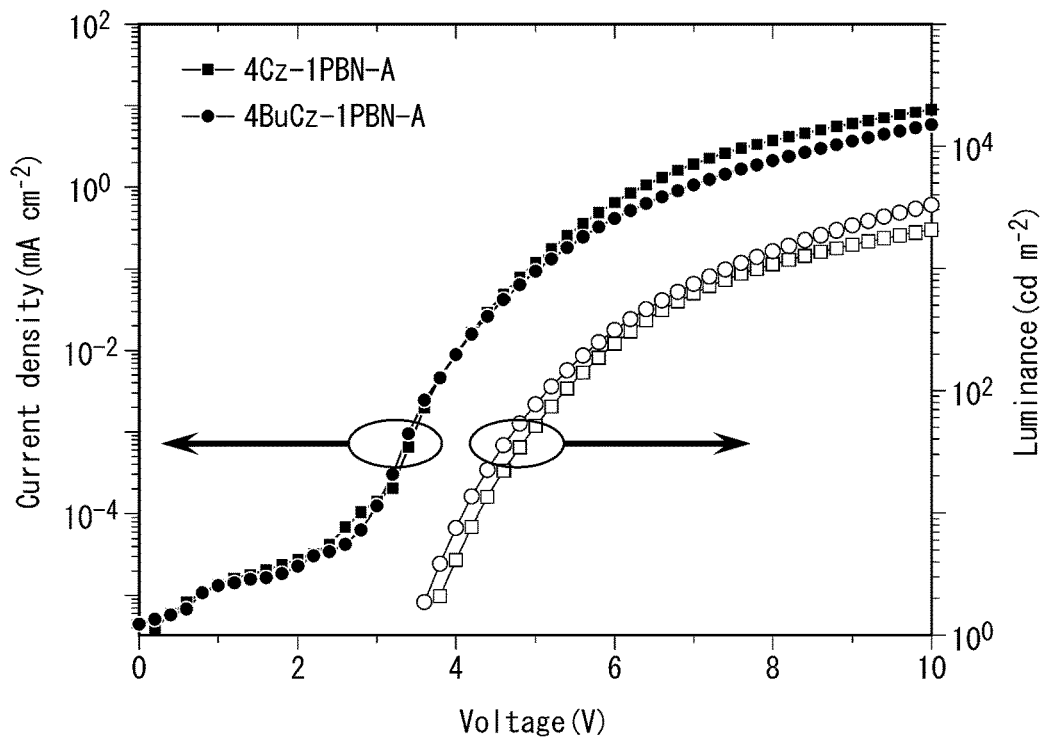
FIG. 5 is a diagram illustrating the voltage-current density-luminance characteristics for 4Cz-1PBN-A and 4BuCz-1PBN-A.
Figure 6:
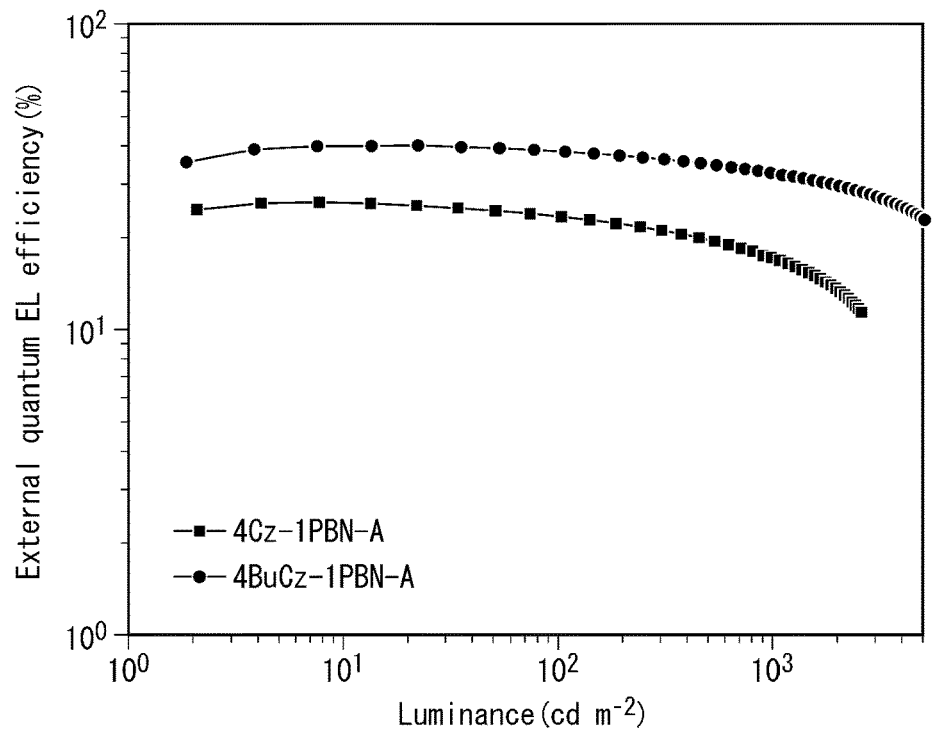
FIG. 6 is a diagram illustrating the luminance-external quantum efficiency characteristics for 4Cz-1PBN-A and 4BuCz-1PBN-A.

With the exception of altering the dopant to 2,3,5,6-tetra (3,6-di-t-butyl-9H-carbazol-9-yl)-4-phenyl-benzonitrile (4BuCz-1PBN-A), a light emission evaluation was conducted using the same method as Example 1. The results are shown in FIGS. 5 and 6. EQEmax was 40.1%.

Example 8

Synthesis of 2,3,5,6-tetra(9H-carbazol-9-yl)-4-phenyl-benzonitrile (4Cz-1PBN-A)

[Chemical formula 171]

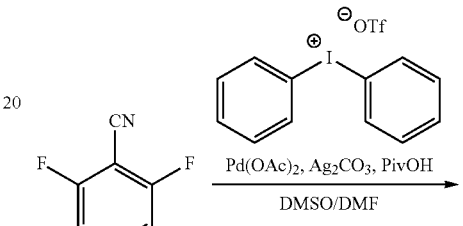

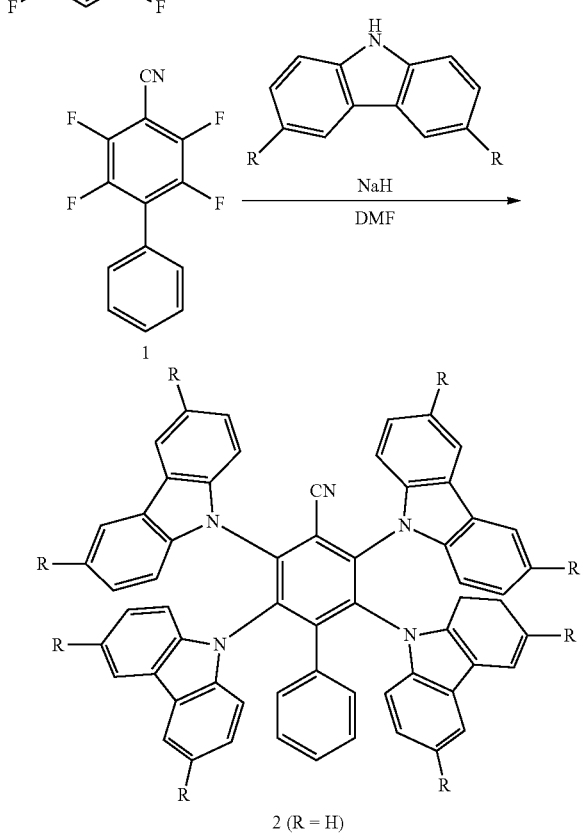

2 (R = H)

A flask that had been flushed with nitrogen was charged with palladium(II) acetate (0.64 g, 2.85 mmol), silver carbonate (15.8 g, 57.3 mmol) and diphenyliodonium trifluoromethanesulfonate (16.0 g, 37.2 mmol), and the mixture was degassed three times. Subsequently, 2,3,5,6-tetrafluorobenzonitrile (5.0 g, 28.6 mmol), pivalic acid (2.92 g, 28.6 mmol), dimethyl sulfoxide (2 mL) and N,N-dimethylformamide (40 mL) were added, and the resulting mixture was stirred at 130° C. for 10 hours. Subsequently, the reaction mixture was returned to room temperature, and impurities were removed using celite. The reaction mixture was then extracted into ethyl acetate. The organic layer was dried by adding sodium sulfate and then purified by column chromatography (ethyl acetate:hexane=1:9) to obtain a white solid of a compound 1 (2.94 g, 41%).

$^1$H-NMR (400 MHz, CDCl$_3$): δ 7.56 to 7.52 (m, 3H), 7.48 to 7.45 (m, 2H)

A flask that had been flushed with nitrogen was charged with carbazole (1.09 g, 6.52 mmol) and N,N-dimethylformamide (10 mL). Subsequently, N,N-dimethylformamide (5 mL) to which potassium tert-butoxide (0.73 g, 6.52 mmol) had been added was added to the flask at room temperature, and the resulting mixture was stirred at room temperature for 30 minutes. N,N-dimethylformamide (10 mL) to which the compound 1 (0.4 g, 1.59 mmol) had been added was then added dropwise to the flask over a period of 10 minutes. Subsequently, the reaction mixture was stirred at 80° C. for 10 hours. The reaction mixture was then returned to room temperature, water (20 mL) was added, and after 30 minutes had elapsed, the mixture was extracted into chloroform. The organic layer was dried by adding sodium sulfate and then purified by column chromatography (ethyl acetate:hexane=1:9) to obtain a yellow solid of a compound 2 (4Cz-1PBN-A) (1.18 g, 88%).

$^1$H-NMR (400 MHz, DMSO-d$_6$): δ 7.92 (d, J=8.4 Hz, 4H), 7.89 to 7.87 (m, 8H), 7.65 (d, J=7.2 Hz, 4H), 7.24 (td, J=7.2 Hz, 1.2 Hz, 4H), 7.15 to 7.08 (m, 8H), 6.94 (td, J=7.4 Hz, 0.8 Hz, 4H), 6.72 (dd, J=8.4 Hz, 1.2 Hz, 2H), 6.44 (tt, J=8.0 Hz, 1.2 Hz, 1H), 6.31 (t, J=7.8 Hz, 2H)

[Evaluation of Light Emission]

With the exception of altering the dopant to 2,3,5,6-tetra (9H-carbazol-9-yl)-4-phenyl-benzonitrile (4Cz-1PBN-A), a light emission evaluation was conducted using the same method as Example 1. The results are shown in FIGS. 5 and 6. EQEmax was 26.1%.

When Example 7 and Example 8 which had the same 4-phenyl-substituted skeleton were compared, it was evident that the compound of the present invention (Example 7) exhibited a relatively higher EQEmax, and was useful as a light-emitting material.

Synthesis Example 9

[Synthesis of 4',5',6'-trifluoro-[1,1':3',1''-terphenyl]-2'-carbonitrile (2PBN-C)]

[Chemical formula 172]

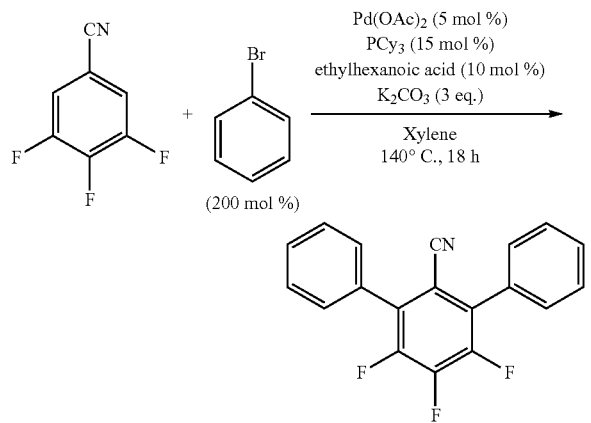

A 200 mL round-bottom flask was charged with 3,4,5-trifluorobenzonitrile (3.00 g, 19.1 mmol), bromobenzene (6.00 g, 38.2 mmol), 2-ethylhexanoic acid (280 mg, 1.91 mmol), potassium carbonate (7.91 g, 57.3 mmol) and 45 ml of xylene. The flask was then degassed and flushed with argon. Subsequently, tricyclohexylphosphine (5.10 ml of a 20% toluene solution, 2.87 mmol) and palladium acetate (214 mg, 0.96 mmol) were added to the flask, and the resulting mixture was stirred at 140° C. for 18 hours. The reaction mixture was then returned to room temperature, ethyl acetate was added, and the insoluble matter was removed by filtration using celite. The filtrate was then washed with water. Subsequently, the filtrate was dried over magnesium sulfate and then concentrated using a rotary evaporator.

The concentrate was washed with n-hexane/ethyl acetate=9/1 to obtain 4.43 g of white crystals of the target product (2PBN-C) (yield: 75.1%).

$^1$H-NMR (400 MHz, CDCl$_3$, δ): 7.55 to 7.47 (m, 10H)

Example 9

Synthesis of 3,4,5-tri(3,6-di-t-butyl-9H-carbazol-9-yl)-2,6-diphenyl-benzonitrile (3BuCz-2PBN-C)

[Chemical formula 173]

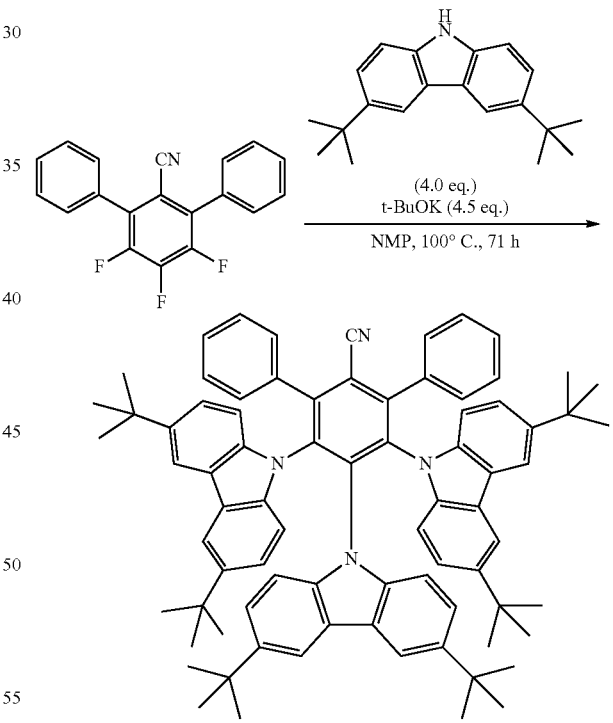

A 100 mL three-neck flask was charged with 4',5',6'-trifluoro-[1,1':3',1''-terphenyl]-2'-carbonitrile (0.75 g, 2.43 mmol), 3,6-di(t-butyl)carbazole (2.71 g, 9.70 mmol), potassium t-butoxide (1.33 g, 10.9 mmol) and 15 mL of N-methyl-2-pyrrolidone, and the resulting mixture was stirred at 100° C. for 71 hours. Subsequently, 100 ml of ice water was added to the flask, and the resulting precipitate was filtered. The filtered solid was dissolved in ether and washed with water. The solution was then dried over magnesium sulfate and concentrated. The concentrate was then purified by separation using silica gel column chromatography (n-hexane/ethyl acetate=19/1) to obtain 1.25 g of the target product (3BuCz-2PBN-C) (yield: 47.3%).

¹H-NMR (400 MHz, CDCl₃, δ): 7.45 (d, 4H), 7.30 (d, 2H), 7.28 (d, 2H), 7.13 (d, 2H), 7.04 (m, 6H), 6.88 (d, 4H), 6.87 (d, 4H), 6.67 (d, 2H), 6.49 (dd, 2H), 1.24 (s, 36H), 1.17 (s, 18H)

[Evaluation of Light Emission]

Figure 7:
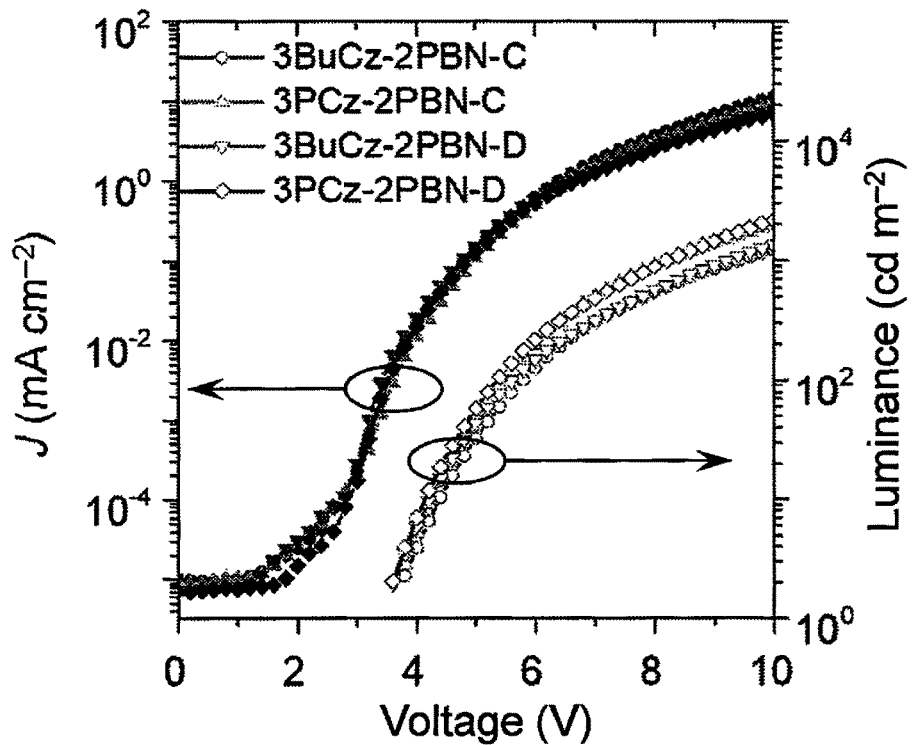
FIG. 7 is a diagram illustrating the voltage-current density-luminance characteristics for 3BuCz-2PBN-C, 3PCz-2PBN-C, 3BuCz-2PBN-D and 3PCz-2PBN-D.
Figure 8:
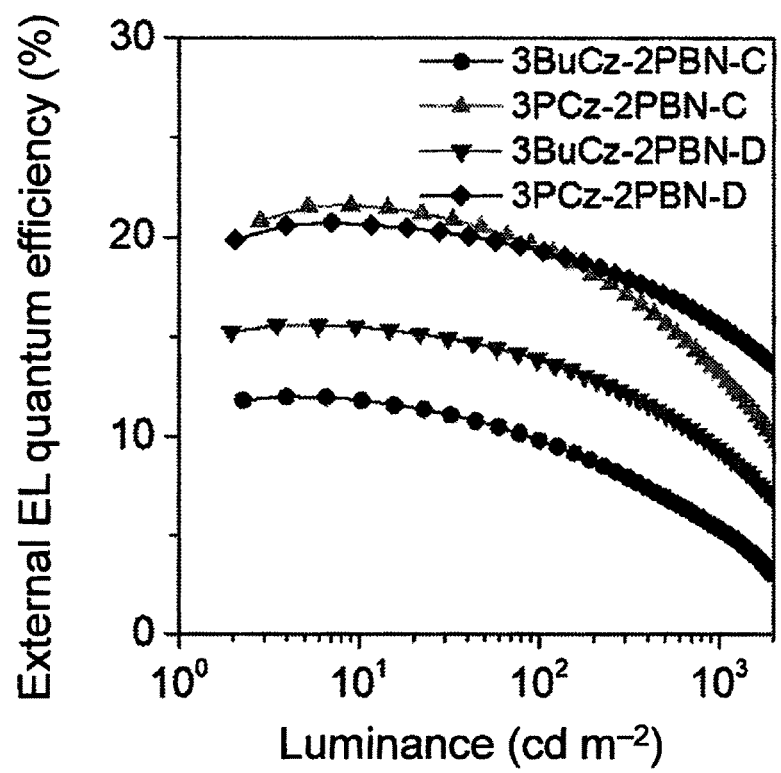
FIG. 8 is a diagram illustrating the luminance-external quantum efficiency characteristics for 3BuCz-2PBN-C, 3PCz-2PBN-C, 3BuCz-2PBN-D and 3PCz-2PBN-D.

With the exception of altering the dopant to 3,4,5-tri(3,6-di-t-butyl-9H-carbazol-9-yl)-2,6-diphenyl-benzonitrile (3BuCz-2PBN-C), a light emission evaluation was conducted using the same method as Example 1. The results are shown in FIGS. 7 and 8. EQEmax was 12.0%.

Example 10

[Synthesis of 3,4,5-tri(3,6-diphenyl-9H-carbazol-9-yl)-2,6-diphenyl-benzonitrile (3PCz-2PBN-C)]

[Chemical formula 174]

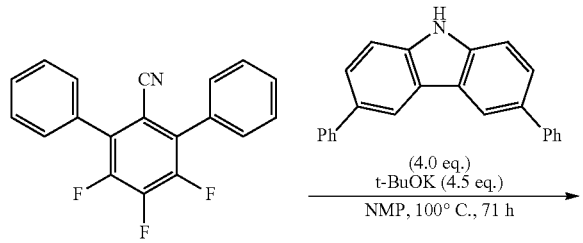

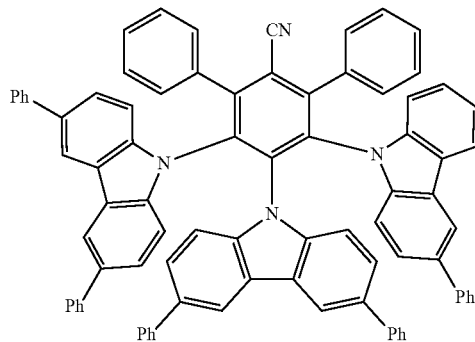

A 50 mL three-neck flask was charged with 4',5',6'-trifluoro-[1,1':3',1"-terphenyl]-2'-carbonitrile (0.36 g, 1.17 mmol), 3,6-diphenylcarbazole (1.50 g, 4.70 mmol), potassium t-butoxide (0.64 g, 5.24 mmol) and 8 mL of N-methyl-2-pyrrolidone, and the resulting mixture was stirred at 140° C. for 18.5 hours. Subsequently, 100 ml of ice water was added to the flask, and the resulting precipitate was filtered. The filtered solid was dissolved in chloroform and washed with water. The solution was then dried over magnesium sulfate and concentrated. The concentrate was then purified by separation using silica gel column chromatography (n-hexane/benzene=2/3) to obtain 0.75 g of the target product (3PCz-2PBN-C) (yield: 53.2%).

¹H-NMR (400 MHz, CDCl₃, δ): 7.80 (s, 4H), 7.47 to 7.41 (m, 14H), 7.36 to 7.32 (m, 8H), 7.28 to 7.21 (m, 22H), 7.16 to 7.14 (m, 6H), 7.09 (d, 2H), 6.86 (dd, 2H)

[Evaluation of Light Emission]

With the exception of altering the dopant to 3,4,5-tri(3,6-diphenyl-9H-carbazol-9-yl)-2,6-diphenyl-benzonitrile (3PCz-2PBN-C), a light emission evaluation was conducted using the same method as Example 1. The results are shown in FIGS. 7 and 8. EQEmax was 21.6%.

Synthesis Example 11

[Synthesis of 3',5',6'-trifluoro-[1,1':4',1"-terphenyl]-2'-carbonitrile (2PBN-D)]

[Chemical formula 175]

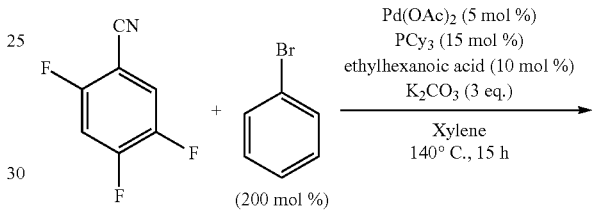

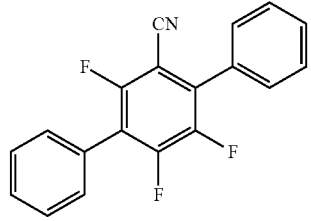

A 200 mL round-bottom flask was charged with 2,4,5-trifluorobenzonitrile (3.00 g, 19.1 mmol), bromobenzene (6.00 g, 38.2 mmol), 2-ethylhexanoic acid (280 mg, 1.91 mmol), potassium carbonate (7.91 g, 57.3 mmol) and 45 ml of xylene. The flask was then degassed and flushed with argon. Subsequently, tricyclohexylphosphine (5.10 ml of a 20% toluene solution, 2.87 mmol) and palladium acetate (214 mg, 0.96 mmol) were added to the flask, and the resulting mixture was stirred at 140° C. for 15 hours. The reaction mixture was then returned to room temperature, ethyl acetate was added, and the insoluble matter was removed by filtration using celite. The filtrate was then washed with water. Subsequently, the filtrate was dried over magnesium sulfate and then concentrated using a rotary evaporator.

Next, 150 ml of chloroform was added to the concentrate, and the mixture was heated to dissolve the concentrate. Subsequently, 300 ml of n-hexane was added and the mixture was cooled. The precipitated white solid was collected by filtration to obtain 4.40 g of the target product (2PBN-D) (yield: 74.6%).

¹H-NMR (400 MHz, CDCl₃, δ): 7.54 to 7.47 (m, 10H)

Example 11

Synthesis of 3,4,6-tri(3,6-diphenyl-9H-carbazol-9-yl)-2,5-diphenyl-benzonitrile (3PCz-2PBN-D)

[Chemical formula 176]

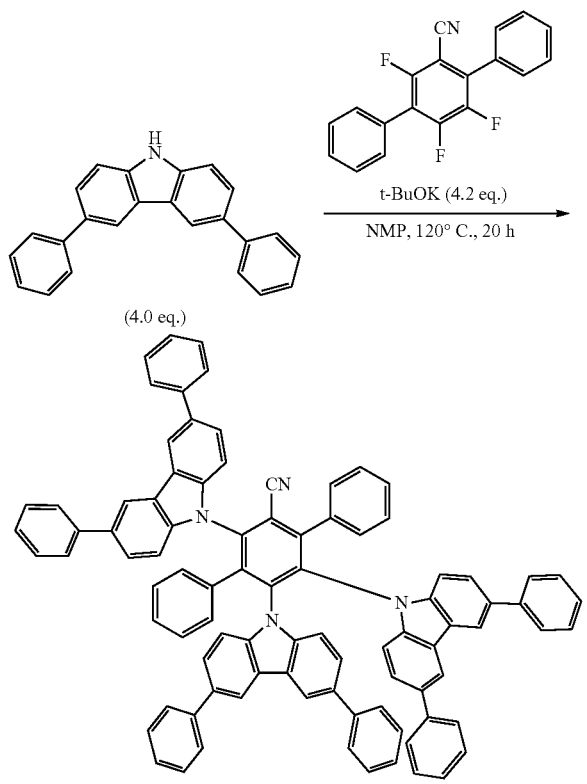

In a 100 mL two-neck flask that had been flushed with nitrogen, 3,6-diphenylcarbazole (1.75 g, 5.5 mmol) was dissolved in 10 mL of N-methyl-2-pyrrolidone. Potassium t-butoxide (0.65 g, 5.8 mmol) was then added to the solution, and the resulting mixture was stirred at room temperature for one hour. Subsequently, 3',5',6'-trifluoro-[1,1':4',1''-terphenyl]-2'-carbonitrile (0.42 g, 1.4 mmol) was suspended in 10 mL of N-methyl-2-pyrrolidone and added to the flask under a stream of nitrogen, and the resulting mixture was then stirred at 120° C. for 20 hours. The reaction mixture was then returned to room temperature, water and ethyl acetate were added, and the organic layer was separated. The water layer was extracted twice with ethyl acetate, and the combined organic layer was washed three times with water, and then twice with a saturated saline solution. The organic layer was dried over magnesium sulfate and filtered, and the filtrate was then concentrated to obtain a crude product. The crude product was purified by silica gel column chromatography (eluent: n-hexane/dichloromethane) to obtain a crudely purified product. This crudely purified product was then once again purified by silica gel column chromatography (eluent: n-hexane/toluene) to obtain 0.93 g of the target product (3PCz-2PBN-D) (yield: 56.7%).

$^1$H-NMR (400 MHz, CDCl$_3$, δ): 8.32 (d, J=2.0 Hz, 2H), 7.33 to 7.70 (m, 8H), 7.66 (d, J=2.0 Hz, 2H), 7.53 to 7.26 (m, 30H), 7.26 to 7.21 (m, 5H), 7.13 (dd, J=8.4 Hz, 2.0 Hz, 2H), 7.05 (d, J=8.4 Hz, 2H), 6.99 (d, J=8.8 Hz, 2H), 6.91 to 6.89 (iii, 2H), 6.67 to 6.57 (m, 3H)

[Evaluation of Light Emission]

With the exception of altering the dopant to 3,4,6-tri(3,6-diphenyl-9H-carbazol-9-yl)-2,5-diphenyl-benzonitrile (3PCz-2PBN-D), a light emission evaluation was conducted using the same method as Example 1. The results are shown in FIGS. 7 and 8. EQEmax was 20.7%.

Example 12

Synthesis of 3,4,6-tri(3,6-di-t-butyl-9H-carbazol-9-yl)-2,5-diphenyl-benzonitrile (3BuCz-2PBN-D)

[Chemical formula 177]

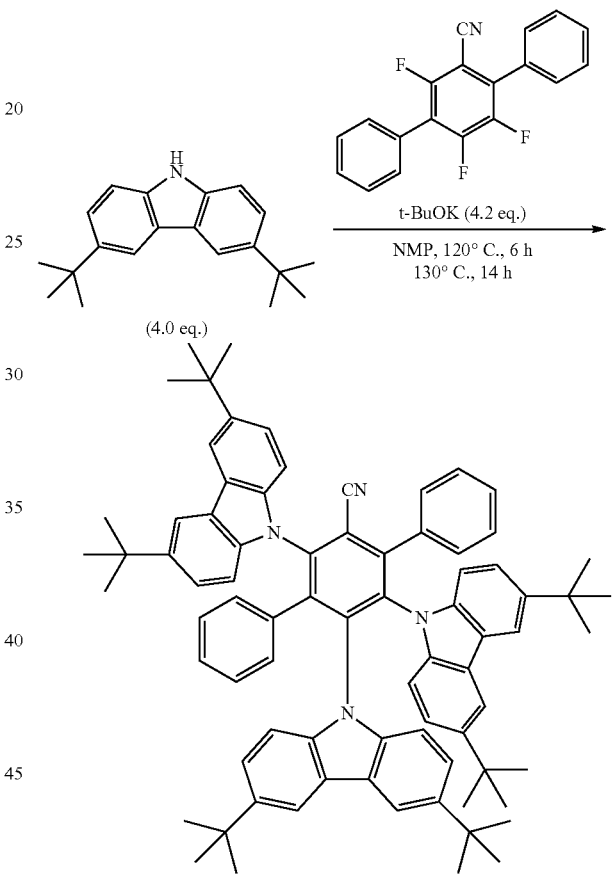

In a 300 mL four-neck flask that had been flushed with nitrogen, 3,6-di-t-butylcarbazole (3.62 g, 13.0 mmol) was dissolved in 65 mL of N-methyl-2-pyrrolidone. Potassium t-butoxide (1.58 g, 14.1 mmol) was then added to the solution, and the resulting mixture was stirred at room temperature for one hour. Subsequently, 3',5',6'-trifluoro-[1,1':4',1''-terphenyl]-2'-carbonitrile (1.00 g, 3.2 mmol) was added to the flask under a stream of nitrogen, and the resulting mixture was then stirred at 120° C. for 6 hours. The mixture was then stirred at 130° C. for 14 hours. The reaction mixture was then returned to room temperature, water and ethyl acetate were added, and the organic layer was separated. The water layer was extracted twice with ethyl acetate, and the combined organic layer was washed three times with water, and then twice with a saturated saline solution. The organic layer was dried over magnesium sulfate and filtered, and the filtrate was then concentrated to obtain a crude product. The crude product was purified by silica gel column chromatography (eluent: n-hexane/dichloromethane, n-hexane/toluene) to obtain 1.73 g of the target product (3BuCz-2PBN-D) (yield: 49.2%).

$^1$H-NMR (400 MHz, CDCl$_3$, δ): 8.03 (d, J=1.2 Hz, 2H), 7.44 to 7.40 (m, 6H), 7.35 (d, J=1.6 Hz, 2H), 7.17 (d, J=8.4 Hz, 2H), 7.10 to 7.06 (m, 3H), 6.83 to 6.76 (m, 6H), 6.66 (d, J=8.4 Hz, 2H), 6.62 (d, J=8.8 Hz, 2H), 6.56 to 6.46 (m, 3H), 1.43 (s, 18H), 1.29 (s, 18H), 1.25 (s, 18H)

[Evaluation of Light Emission]

With the exception of altering the dopant to 3,4,6-tri(3,6-di-t-butyl-9H-carbazol-9-yl)-2,5-diphenyl-benzonitrile (3BuCz-2PBN-D), a light emission evaluation was conducted using the same method as Example 1. The results are shown in FIGS. 7 and 8. EQEmax was 15.6%.

Synthesis Example 13

[Synthesis of 2,4,5,6-tetrafluoro-[1,1'-biphenyl]-3-carbonitrile (1PBN-C)]

[Chemical formula 178]

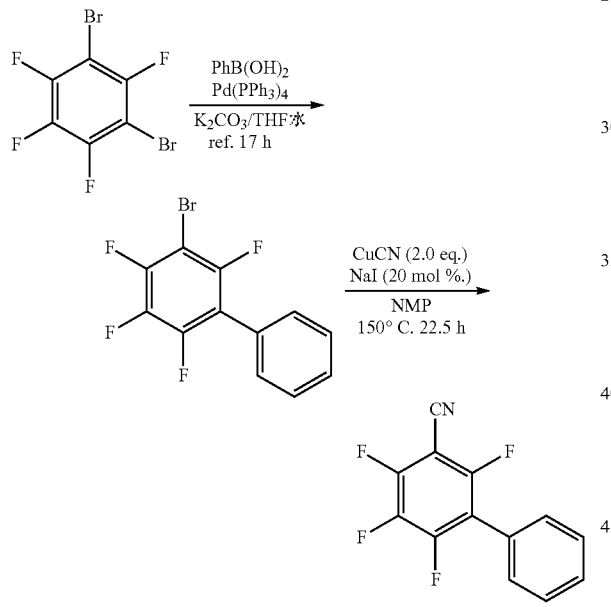

A 300 mL round-bottom flask was charged with 1,3-dibromotetrafluorobenzene (6.50 g, 21.1 mmol), phenylboronic acid (2.73 g, 22.4 mmol), potassium carbonate (8.74 g, 63.3 mmol), 26 ml of water and 65 ml of tetrahydrofuran. The flask was degassed and then flushed with argon. Subsequently, Pd(PPh$_3$)$_4$ (0.56 g, 0.63 mmol) was added, and the reaction mixture was stirred while heating under reflux for 17 hours. The thus obtained liquid was cooled to room temperature and extracted into 100 ml of diethyl ether. Subsequently, the solution was washed twice with 50 ml samples of water, dried over magnesium sulfate, and then concentrated using a rotary evaporator. The concentrate was separated and purified by silica gel column chromatography (n-hexane) to obtain 2.93 g of 3-bromo-2,4,5,6-tetrafluoro-1,1'-biphenyl (yield: 45.5%).

$^1$H-NMR (400 MHz, CDCl$_3$, δ): 7.50 to 7.38 (m, 5H)

A 200 ml round-bottom flask was charged with 3-bromo-2,4,5,6-tetrafluoro-1,1'-biphenyl (2.97 g, 9.74 mmol), copper cyanide (1.74 g, 19.4 mmol), sodium iodide (0.29 g, 1.93 mmol) and 30 ml of N-methyl-2-pyrrolidone, and the resulting mixture was stirred at 150° C. for 22.5 hours. The reaction mixture was then cooled to room temperature. Subsequently, 50 ml of diethyl ether was added, and the resulting mixture was washed with 10% ammonia water and then with water. The mixture was then dried by adding magnesium sulfate, and then concentrated using a rotary evaporator. The concentrate was separated and purified by silica gel column chromatography (n-hexane/benzene=2/1) to obtain 2.05 g of the target product 2,4,5,6-tetrafluoro-[1,1'-biphenyl]-3-carbonitrile (yield: 83.3%).

$^1$H-NMR (400 MHz, CDCl$_3$, δ): 7.51 to 7.48 (m, 3H), 7.40 to 7.37 (m, 2H)

Example 13

[Synthesis of 2,4,5,6-tetrakis(3,6-di-tert-butyl-9H-carbazol-9-yl)-[1,1'-biphenyl]-3-carbonitrile (4BuCz-1PBN-C)]

[Chemical formula 179]

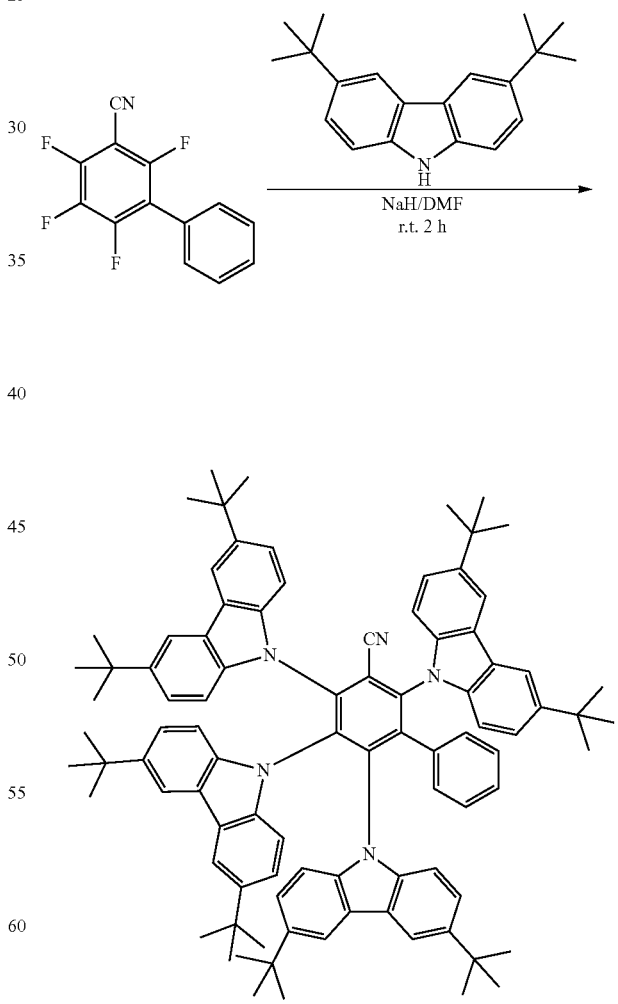

A 50 mL round-bottom flask was charged with 2,4,5,6-tetrafluoro-[1,1'-biphenyl]-3-carbonitrile (0.25 g, 1.0 mmol), 3,6-di-t-butyl-carbazole (1.25 g, 4.47 mmol) and 10 ml of anhydrous DMF, and the resulting mixture was cooled in an ice bath. Subsequently, 60% sodium hydride (0.20 g, 5.00 mmol) was added gradually to the flask. The resulting mixture was then stirred at room temperature for 2 hours. The thus obtained mixture was poured into ice water, and the resulting precipitate was collected by filtration. The filtered product was then dissolved in ether and washed with water. The solution was dried over magnesium sulfate and then concentrated. The concentrate was separated and purified by silica gel chromatography (n-hexane/benzene=2/1). The thus obtained purified product was washed with 2-propanol to obtain 1.14 g of the target product (4BuCz-1PBN-C) (yield: 88.9%).

$^1$H-NMR (400 MHz, CDCl$_3$, δ): 8.01 (d, 2H), 7.59 (s, 2H), 7.46 to 7.44 (m, 4H), 7.18 (dd, 4H), 6.98 (d, 4H), 6.91 (dd, 4H), 6.67 to 6.64 (m, 4H), 6.55 to 6.52 (m, 3H), 6.43 (dd, 2H), 1.43 (s, 18H), 1.30 (s, 18H), 1.22 (s, 18H), 1.21 (s, 18H)

[Evaluation of Light Emission]

Figure 9:
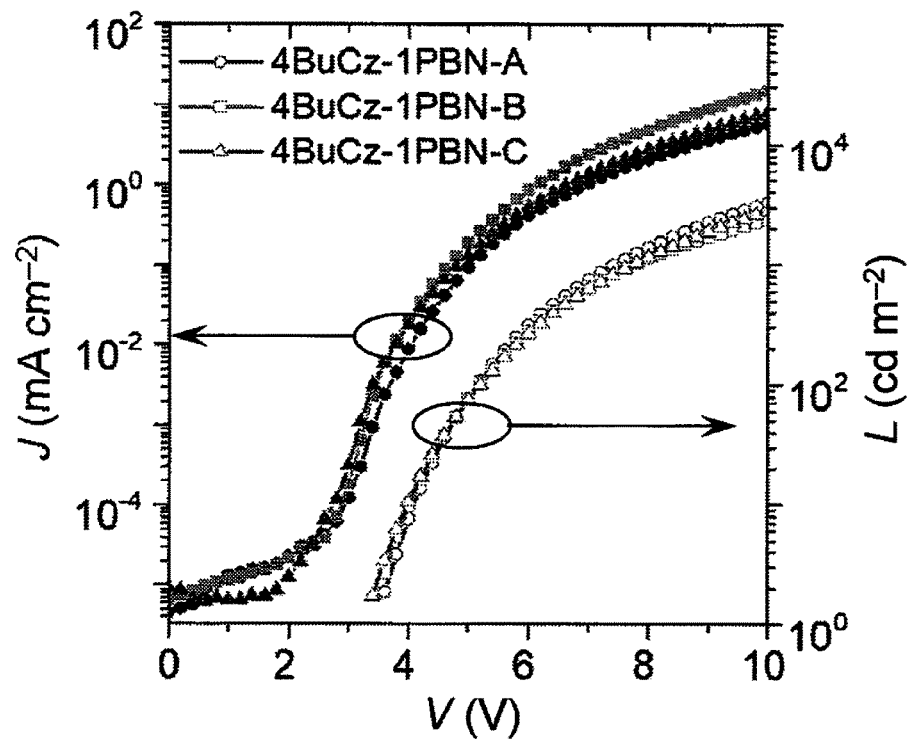
FIG. 9 is a diagram illustrating the voltage-current density-luminance characteristics for 4BuCz-1PBN-A, 4BuCz-1PBN-B and 4BuCz-1PBN-C.
Figure 10:
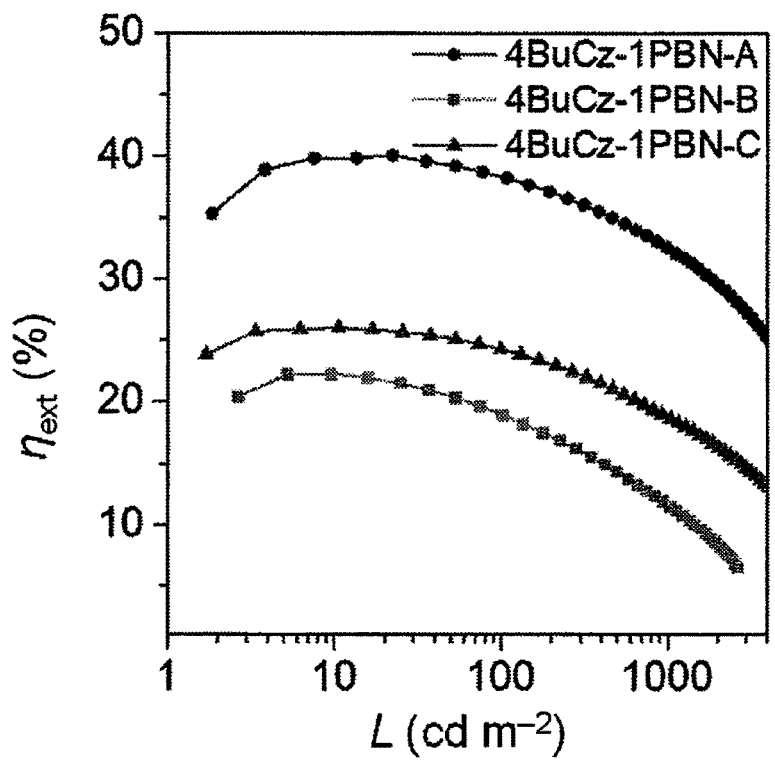
FIG. 10 is a diagram illustrating the luminance-external quantum efficiency characteristics for 4BuCz-1PBN-A, 4BuCz-1PBN-B and 4BuCz-1PBN-C.

With the exception of altering the dopant to 2,4,5,6-tetrakis(3,6-di-tert-butyl-9H-carbazol-9-yl)-[1,1'-biphenyl]-3-carbonitrile (4BuCz-1PBN-C), a light emission evaluation was conducted using the same method as Example 1. The results are shown in FIGS. 9 and 10. EQEmax was 26.0%.

Example 14

[Synthesis of 3,4,5,6-tetrakis(3,6-di-tert-butyl-9H-carbazol-9-yl)-[1,1'-biphenyl]-2-carbonitrile (4BuCz-1PBN-B)]

[Chemical formula 180]

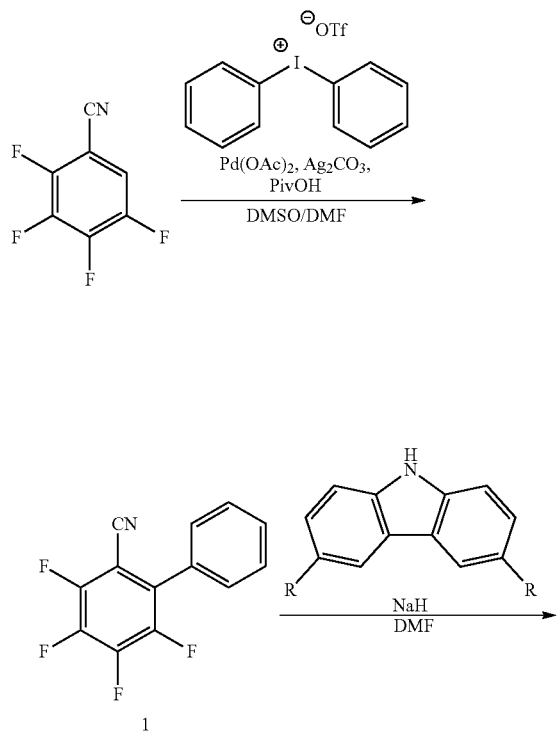

-continued

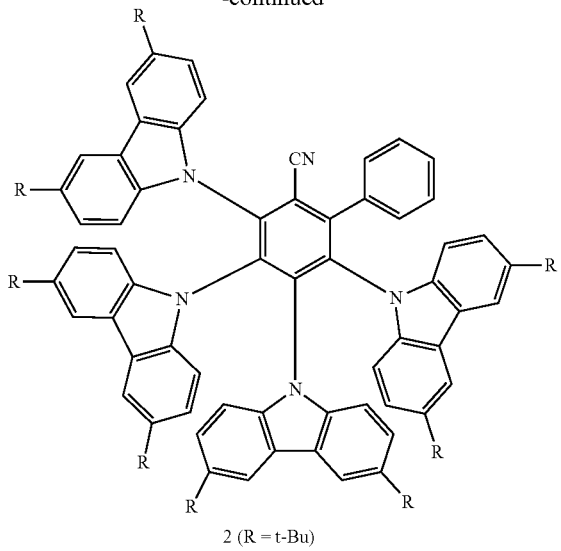

2 (R = t-Bu)

A flask that had been flushed with nitrogen was charged palladium(II) acetate (0.13 g, 0.58 mmol), silver carbonate (3.15 g, 11.4 mmol) and diphenyliodonium trifluoromethanesulfonate (3.19 g, 7.42 mmol), and the mixture was degassed three times. Subsequently, 2,3,4,5-tetrafluorobenzonitrile (1.0 g, 5.71 mmol), pivalic acid (0.58 g, 5.68 mmol), dimethyl sulfoxide (0.5 mL) and N,N-dimethylformamide (8 mL) were added, and the resulting mixture was stirred at 130° C. for 10 hours. Subsequently, the reaction mixture was returned to room temperature, and impurities were removed using celite. The reaction mixture was then extracted into ethyl acetate. The organic layer was dried by adding sodium sulfate and then purified by column chromatography (ethyl acetate:hexane=1:9) to obtain a white solid of a compound 1 (0.49 g, 34%).

$^1$H-NMR (400 MHz, CDCl$_3$): δ 7.58 to 7.53 (m, 3H), 7.51 to 7.45 (m, 3H)

A flask that had been flushed with nitrogen was charged with 3,6-di-tert-butylcarbazole (1.37 g, 4.90 mmol) and N,N-dimethylformamide (10 mL). Subsequently, a mixture of potassium tert-butoxide (0.55 g, 4.90 mmol) and N,N-dimethylformamide (5 mL) was added to the flask at room temperature, and the resulting mixture was stirred at room temperature for 30 minutes. A mixture of the compound 1 (0.30 g, 1.19 mmol) and N,N-dimethylformamide (10 mL) was then added dropwise to the flask over a period of 10 minutes. Subsequently, the reaction mixture was stirred at 80° C. for 10 hours. The reaction mixture was then returned to room temperature, water (20 mL) was added, and after 30 minutes had elapsed, the mixture was extracted into chloroform. The organic layer was dried by adding sodium sulfate and then purified by column chromatography (ethyl acetate:hexane=1:9) to obtain a yellow solid of a compound 2 (4BuCz-1PBN-B) (1.24 g, 81%).

$^1$H-NMR (400 MHz, DMSO-d$_6$): δ 7.73 (d, J=1.0 Hz, 2H), 7.52 (d, J=6.8 Hz, 4H), 7.32 to 7.27 (m, 4H), 7.21 to 7.11 (m, 11H), 6.99 (d, J=8.4 Hz, 2H), 6.87 (d, J=8.8 Hz, 2H), 6.63 to 6.59 (m, 4H), 1.33 (s, 18H), 1.27 (s, 18H), 1.16 (d, J=8.0 Hz, 36H)

[Evaluation of Light Emission]

With the exception of altering the dopant to 3,4,5,6-tetrakis(3,6-di-tert-butyl-9H-carbazol-9-yl)-[1,1'-biphenyl]-2-carbonitrile (4BuCz-1PBN-B), a light emission evaluation was conducted using the same method as Example 1. The results are shown in FIGS. 9 and 10. EQEmax was 22.3%.

Example 15

[Synthesis of 2,3,5,6-tetrakis(3,6-di-tert-butyl-9H-carbazol-9-yl)-[1,1'-biphenyl]-4-carbonitrile (4BuCz-1PBN-A)]

The target product (4BuCz-1PBN-A) was obtained using the same method as Example 7.

[Chemical formula 181]

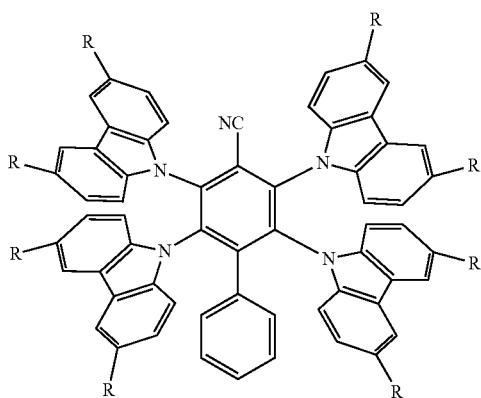

(R = t-Bu)

[Evaluation of Light Emission]

With the exception of altering the dopant to 2,3,5,6-tetrakis(3,6-di-tert-butyl-9H-carbazol-9-yl)-[1,1'-biphenyl]-4-carbonitrile (4BuCz-1PBN-B), a light emission evaluation was conducted using the same method as Example 1. The results are shown in FIGS. 9 and 10.

Synthesis Example 16

[Synthesis of 4'-(tert-butyl)-2,3,5,6-tetrafluoro-[1,1'-biphenyl]-4-carbonitrile

[Chemical formula 182]

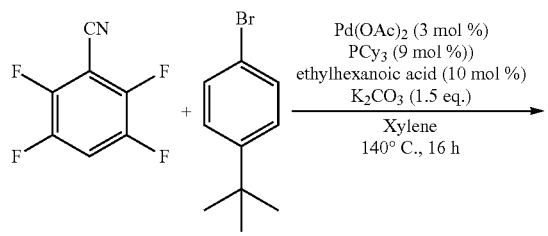

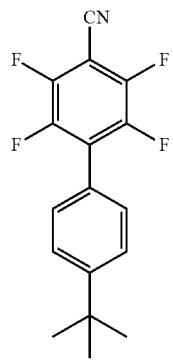

A 50 ml round-bottom flask was charged with 2,3,5,6-tetrafluorobenzonitrile (0.50 g, 2.86 mmol), 4-tert-butylbromobenzene (0.64 g, 3.00 mmol), 2-ethylhexanoic acid (41.0 mg, 0.29 mmol), potassium carbonate (0.59 g, 4.29 mmol) and 10 ml of xylene. The flask was degassed and flushed with argon, tricyclohexylphosphine (0.45 ml of a 20% toluene solution, 0.25 mmol) and palladium acetate (19.2 mg, 0.09 mmol) were then added, and the resulting mixture was stirred at 140° C. for 16 hours. The reaction liquid was then returned to room temperature, ethyl acetate was added, and the insoluble matter was removed by filtration. The filtrate was washed with water, dried over magnesium sulfate, and then concentrated using a rotary evaporator. The residue was separated and purified by silica gel column chromatography (n-hexane/benzene=2/1) to obtain 0.50 g of crystals of the target product (yield: 56.8%).

$^1$H-NMR (400 MHz, CDCl$_3$, δ): 7.53 (d, 2H), 7.40 (d, 2H), 1.36 (s, 9H)

Example 16

[Synthesis of 4'-(tert-butyl)-2,3,5,6-tetrakis(3,6-di-tert-butyl-9H-carbazol-9-yl)-[1,1'-biphenyl]-4-carbonitrile (4X-BCz-PBN-Bu)]

[Chemical formula 183]

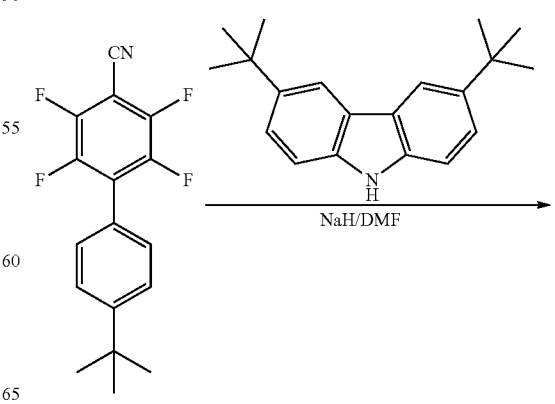

-continued

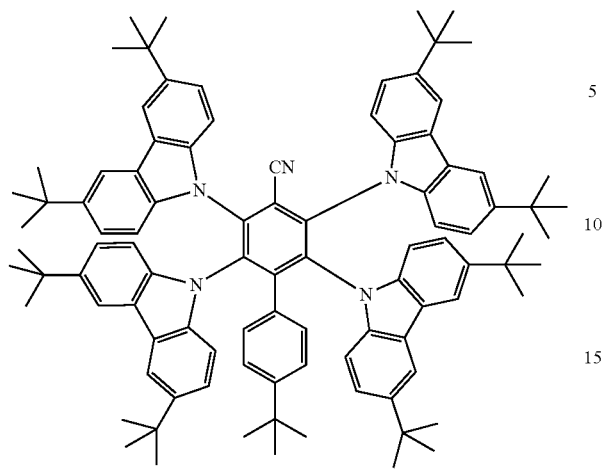

A 100 mL round-bottom flask was charged with 4'-(tert-butyl)-2,3,5,6-tetrafluoro-[1,1'-biphenyl]-4-carbonitrile (0.50 g, 1.63 mmol), 3,6-di-t-butyl-carbazole (2.05 g, 7.34 mmol) and 20 ml of anhydrous DMF, and the resulting mixture was cooled in an ice bath. Subsequently, 60% sodium hydride (0.33 g, 8.15 mmol) was added gradually to the flask, and the resulting mixture was then stirred at room temperature for 5 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=2/1). The thus obtained crystals were washed with 2-propanol to obtain 1.66 g of the target product (yield: 75.8%).

$^1$H-NMR (400 MHz, CDCl$_3$, δ): 7.55 (d, 4H), 7.42 (d, 4H), 6.94 (dd, 4H), 6.88 (d, 4H), 6.78 (dd, 6H), 6.62 (d, 4H), 6.48 (d, 2H), 1.35 (s, 36H), 1.39 (s, 36H), 0.71 (s, 9H)

[Evaluation of Light Emission]

Figure 11:
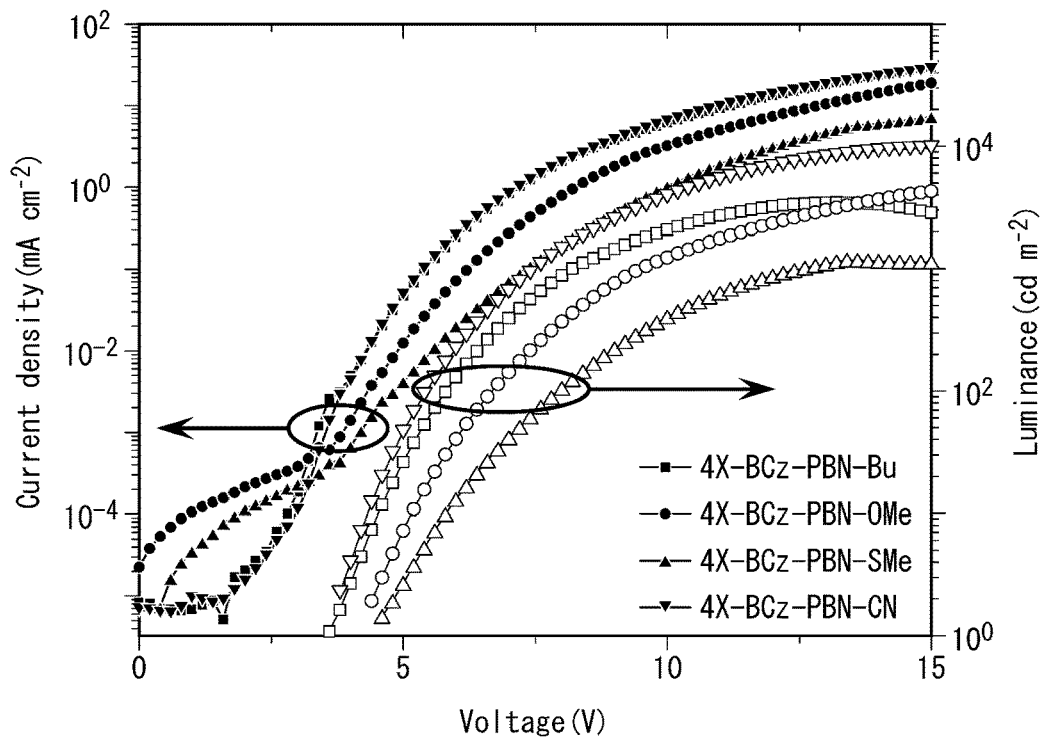
FIG. 11 is a diagram illustrating the voltage-current density-luminance characteristics for 4X-BCz-PBN-Bu, 4X-BCz-PBN-OMe, 4X-BCz-PBN-SMe and 4X-BCz-PBN-CN.
Figure 12:
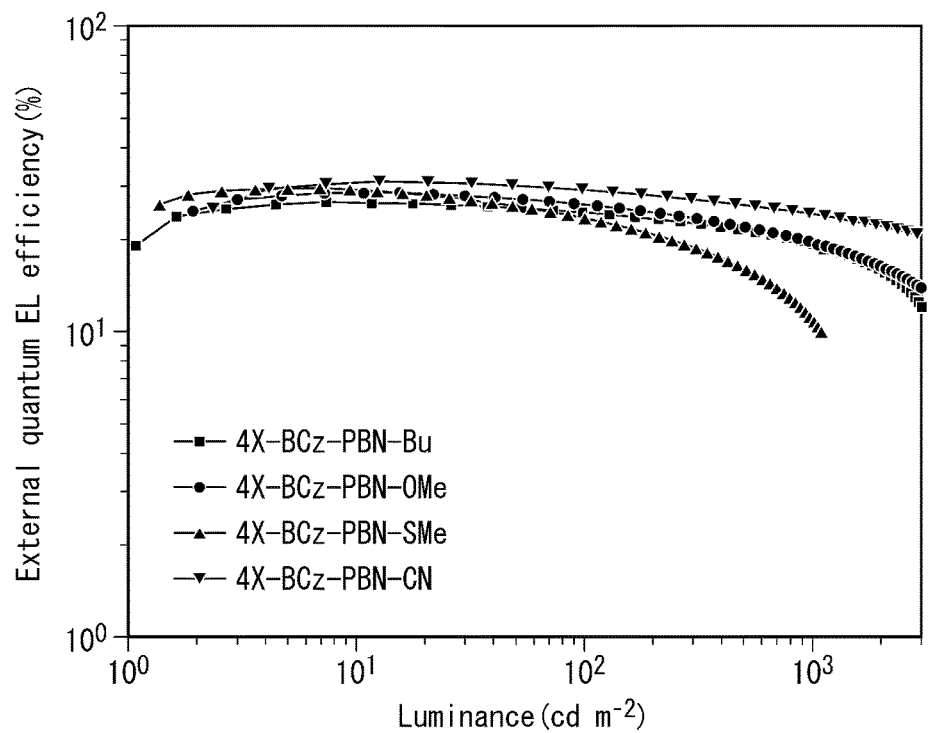
FIG. 12 is a diagram illustrating the luminance-external quantum efficiency characteristics for 4X-BCz-PBN-Bu, 4X-BCz-PBN-OMe, 4X-BCz-PBN-SMe and 4X-BCz-PBN-CN.

With the exception of altering the dopant to 4'-(tert-butyl)-2,3,5,6-tetrakis(3,6-di-tert-butyl-9H-carbazol-9-yl)-[1,1'-biphenyl]-4-carbonitrile (4X-BCz-PBN-Bu), a light emission evaluation was conducted using the same method as Example 1. The results are shown in FIGS. 11 and 12. EQEmax was 26.5%.

Synthesis Example 17

[Synthesis of 4'-methoxy-2,3,5,6-tetrafluoro-[1,1'-biphenyl]-4-carbonitrile

[Chemical formula 184]

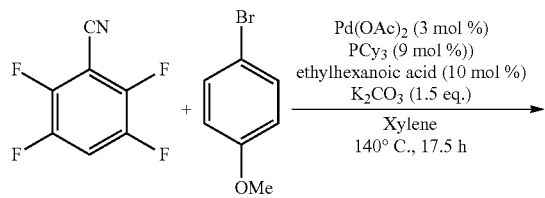

-continued

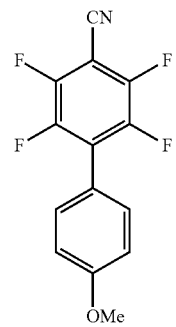

A 50 ml round-bottom flask was charged with 2,3,5,6-tetrafluorobenzonitrile (0.80 g, 4.57 mmol), 4-methoxybromobenzene (0.90 g, 4.80 mmol), 2-ethylhexanoic acid (66.0 mg, 0.46 mmol), potassium carbonate (0.95 g, 6.86 mmol) and 10 ml of xylene. The flask was degassed and flushed with argon, tricyclohexylphosphine (0.72 ml of a 20% toluene solution, 0.41 mmol) and palladium acetate (31.0 mg, 0.14 mmol) were then added, and the resulting mixture was stirred at 140° C. for 17.5 hours. The reaction liquid was then returned to room temperature, ethyl acetate was added, and the insoluble matter was removed by filtration. The filtrate was washed with water, dried over magnesium sulfate, and then concentrated using a rotary evaporator. The residue was separated and purified by silica gel column chromatography (n-hexane/benzene=2/1) to obtain 0.63 g of crystals of the target product (yield: 49.2%).

$^1$H-NMR (400 MHz, CDCl$_3$, δ): 7.41 (d, 2H), 7.03 (d, 2H), 3.87 (s, 3H)

Example 17

[Synthesis of 2,3,5,6-tetrakis(3,6-di-tert-butyl-9H-carbazol-9-yl)-4'-methoxy-[1,1'-biphenyl]-4-carbonitrile (4X-BCz-PBN-OMe)]

[Chemical formula 185]

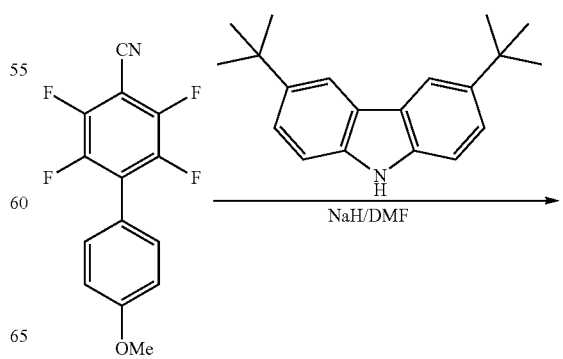

-continued

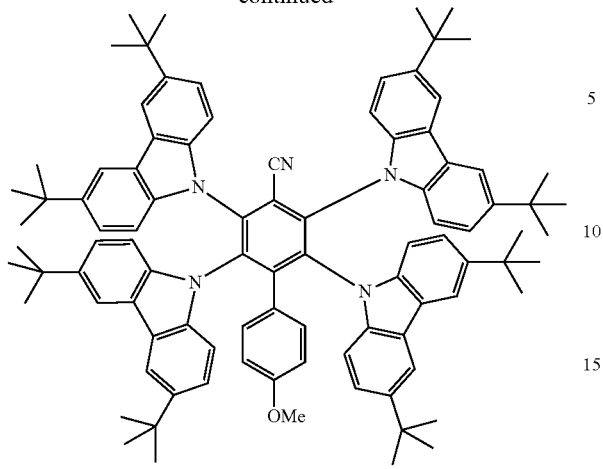

A 100 mL round-bottom flask was charged with 4'-methoxy-2,3,5,6-tetrafluoro-[1,1'-biphenyl]-4-carbonitrile (0.50 g, 1.78 mmol), 3,6-di-t-butyl-carbazole (2.24 g, 8.01 mmol) and 20 ml of anhydrous DMF, and the resulting mixture was cooled in an ice bath. Subsequently, 60% sodium hydride (0.36 g, 8.90 mmol) was added gradually to the flask, and the resulting mixture was then stirred at room temperature for 3 hours and then at 80° C. for 2 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=2/1). The thus obtained crystals were washed with 2-propanol to obtain 1.93 g of the target product (yield: 82.5%).

$^1$H-NMR (400 MHz, CDCl$_3$, δ): 7.54 (d, 4H), 7.43 (d, 4H), 6.93 (dd, 4H), 6.86 (d, 4H), 6.81 (dd, 6H), 6.63 (d, 4H), 6.06 (d, 2H), 3.23 (s, 3H), 1.34 (s, 36H), 1.30 (s, 36H)

[Evaluation of Light Emission]

With the exception of altering the dopant to 2,3,5,6-tetrakis(3,6-di-tert-butyl-9H-carbazol-9-yl)-4'-methoxy-[1,1'-biphenyl]-4-carbonitrile (4X-BCz-PBN-OMe), a light emission evaluation was conducted using the same method as Example 1. The results are shown in FIGS. 11 and 12. EQEmax was 28.5%.

Synthesis Example 18

[Synthesis of 4'-methylthio-2,3,5,6-tetrafluoro-[1,1'-biphenyl]-4-carbonitrile]

[Chemical formula 186]

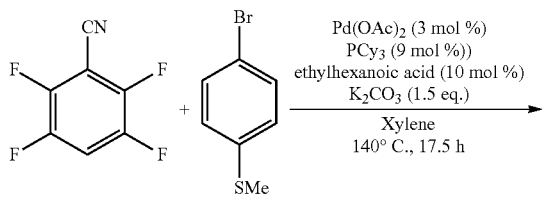

-continued

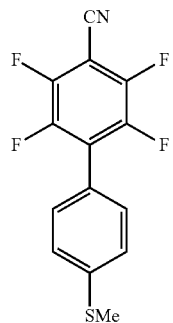

A 50 ml round-bottom flask was charged with 2,3,5,6-tetrafluorobenzonitrile (0.80 g, 4.57 mmol), 4-methylthio-bromobenzene (0.97 g, 4.80 mmol), 2-ethylhexanoic acid (66.0 mg, 0.46 mmol), potassium carbonate (0.95 g, 6.86 mmol) and 10 ml of xylene. The flask was degassed and flushed with argon, tricyclohexylphosphine (0.72 ml of a 20% toluene solution, 0.41 mmol) and palladium acetate (31.0 mg, 0.14 mmol) were then added, and the resulting mixture was stirred at 140° C. for 17.5 hours. The reaction liquid was then returned to room temperature, ethyl acetate was added, and the insoluble matter was removed by filtration. The filtrate was washed with water, dried over magnesium sulfate, and then concentrated using a rotary evaporator. The residue was separated and purified by silica gel column chromatography (n-hexane/benzene=2/1) to obtain 0.68 g of crystals of the target product (yield: 50.0%).

$^1$H-NMR (400 MHz, CDCl$_3$, δ): 7.37 (d, 2H), 7.34 (d, 2H), 2.53 (s, 3H)

Example 18

[Synthesis of 2,3,5,6-tetrakis(3,6-di-tert-butyl-9H-carbazol-9-yl)-4'-methylthio-[1,1'-biphenyl]-4-carbonitrile (4X-BCz-PBN-SMe)]

[Chemical formula 187]

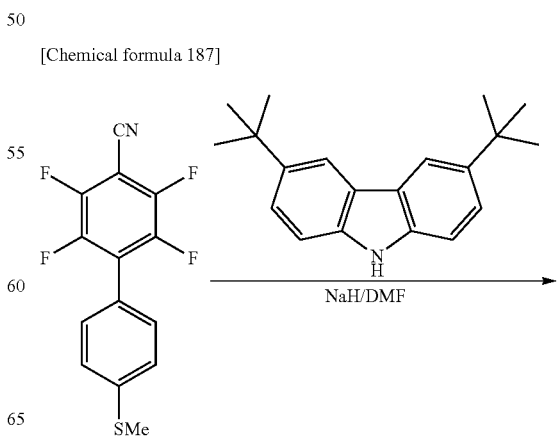

-continued

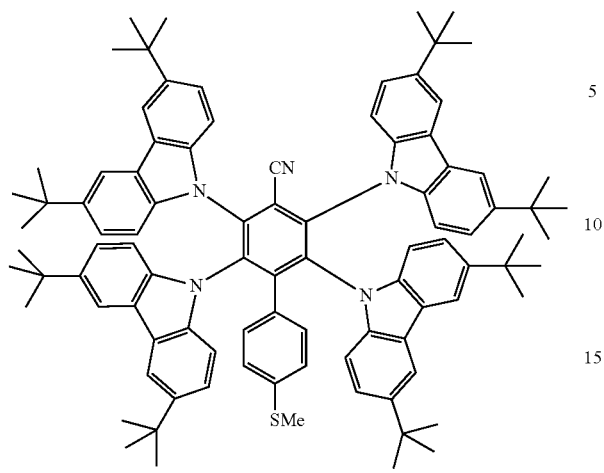

A 100 mL round-bottom flask was charged with 4'-methylthio-2,3,5,6-tetrafluoro-[1,1'-biphenyl]-4-carbonitrile (0.50 g, 1.68 mmol), 3,6-di-t-butyl-carbazole (2.12 g, 7.56 mmol) and 20 ml of anhydrous DMF, and the resulting mixture was cooled in an ice bath. Subsequently, 60% sodium hydride (0.34 g, 8.40 mmol) was added gradually to the flask, and the resulting mixture was then stirred at room temperature for 4 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/ethyl acetate=19/1). The thus obtained crystals were washed with 2-propanol to obtain 2.08 g of the target product (yield: 92.9%).

$^1$H-NMR (400 MHz, CDCl$_3$, δ): 7.56 (d, 4H), 7.44 (d, 4H), 6.95 (dd, 4H), 6.85 (d, 4H), 6.83 (dd, 6H), 6.64 (d, 4H), 6.42 (d, 2H), 1.96 (s, 3H), 1.36 (s, 36H), 1.32 (s, 36H)

[Evaluation of Light Emission]

With the exception of altering the dopant to 2,3,5,6-tetrakis(3,6-di-tert-butyl-9H-carbazol-9-yl)-4'-methylthio-[1,1'-biphenyl]-4-carbonitrile (4X-BCz-PBN-SMe), a light emission evaluation was conducted using the same method as Example 1. The results are shown in FIGS. 11 and 12. EQEmax was 29.0%.

Synthesis Example 19

[Synthesis of 2,3,5,6-tetrafluoro-[1,1'-biphenyl]-4,4'-dicarbonitrile]

[Chemical formula 188]

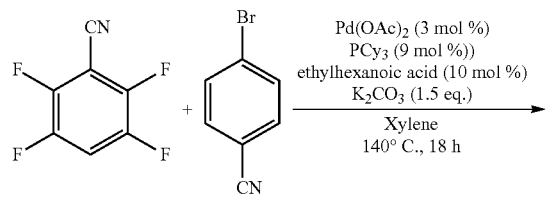

-continued

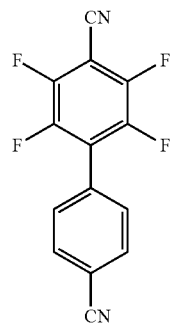

A 50 ml round-bottom flask was charged with 2,3,5,6-tetrafluorobenzonitrile (0.80 g, 4.57 mmol), 4-cyanobromobenzene (0.87 g, 4.80 mmol), 2-ethylhexanoic acid (66.0 mg, 0.46 mmol), potassium carbonate (0.95 g, 6.86 mmol) and 15 ml of xylene. The flask was degassed and flushed with argon, tricyclohexylphosphine (0.72 ml of a 20% toluene solution, 0.41 mmol) and palladium acetate (31.0 mg, 0.14 mmol) were then added, and the resulting mixture was stirred at 140° C. for 18 hours. The reaction liquid was then returned to room temperature, ethyl acetate was added, and the insoluble matter was removed by filtration. The filtrate was washed with water, dried over magnesium sulfate, and then concentrated using a rotary evaporator. The residue was separated and purified by silica gel column chromatography (n-hexane/benzene=1/1) to obtain 0.79 g of crystals of the target product (yield: 62.7%).

$^1$H-NMR (400 MHz, CDCl$_3$, δ): 7.83 (d, 2H), 7.58 (d, 2H)

Example 19

[Synthesis of 2,3,5,6-tetrakis(3,6-di-tert-butyl-9H-carbazol-9-yl)-[1,1'-biphenyl]-4,4'-dicarbonitrile (4X-BCz-PBN-CN)]

[Chemical formula 189]

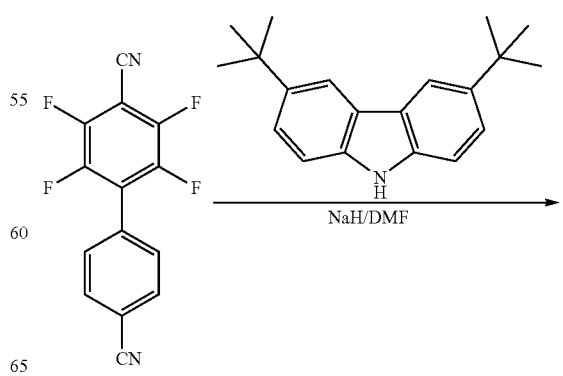

-continued

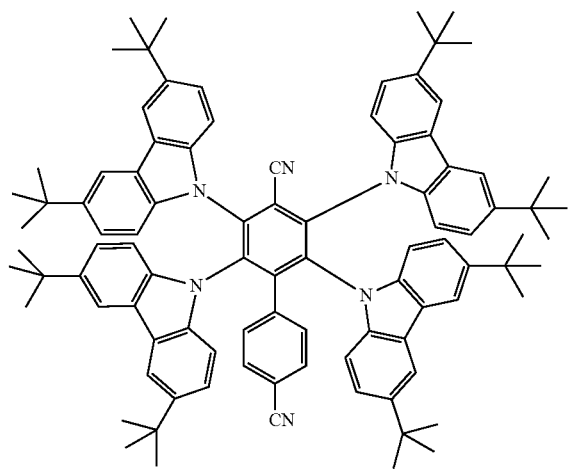

A 50 mL round-bottom flask was charged with 2,3,5,6-tetrafluoro-[1,1'-biphenyl]-4,4'-dicarbonitrile (0.25 g, 0.91 mmol), 3,6-di-t-butyl-carbazole (1.27 g, 4.55 mmol) and 10 ml of anhydrous DMF, and the resulting mixture was cooled in an ice bath. Subsequently, 60% sodium hydride (0.18 g, 4.53 mmol) was added gradually to the flask, and the resulting mixture was then stirred at room temperature for 2 hours and then at 80° C. for 5 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=1/1). The thus obtained crystals were washed with 2-propanol to obtain 1.12 g of the target product (yield: 94.1%).

$^1$H-NMR (400 MHz, CDCl$_3$, δ): 7.57 (d, 4H), 7.46 (d, 4H), 7.03 (d, 2H), 6.96 (dd, 4H), 6.87 (d, 4H), 6.84 (dd, 6H), 6.59 (d, 4H), 1.35 (s, 36H), 1.31 (s, 36H)

[Evaluation of Light Emission]

With the exception of altering the dopant to 2,3,5,6-tetrakis(3,6-di-tert-butyl-9H-carbazol-9-yl)-[1,1'-biphenyl]-4,4'-dicarbonitrile (4X-BCz-PBN-CN), a light emission evaluation was conducted using the same method as Example 1. The results are shown in FIGS. 11 and 12. EQEmax was 31.6%.

Synthesis Example 20

[Synthesis of 4'-cyano-2',3',5',6'-tetrafluoro-[1,1'-biphenyl]-4-carboxylic acid methyl ester

[Chemical formula 190]

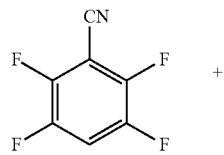

-continued

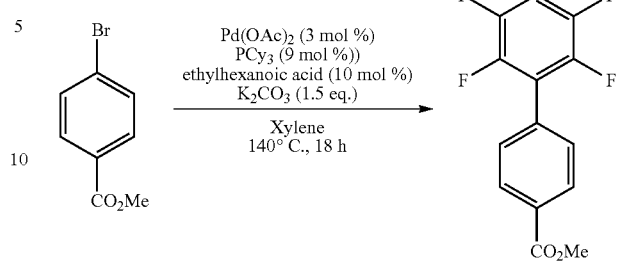

A 100 ml round-bottom flask was charged with 2,3,5,6-tetrafluorobenzonitrile (1.00 g, 5.71 mmol), 4-methoxycarbonylbromobenzene (1.29 g, 6.00 mmol), 2-ethylhexanoic acid (82.0 mg, 0.57 mmol), potassium carbonate (1.18 g, 8.56 mmol) and 20 ml of xylene. The flask was degassed and flushed with argon, tricyclohexylphosphine (0.90 ml of a 20% toluene solution, 0.51 mmol) and palladium acetate (38.5 mg, 0.17 mmol) were then added, and the resulting mixture was stirred at 140° C. for 18 hours. The reaction liquid was then returned to room temperature, ethyl acetate was added, and the insoluble matter was removed by filtration. The filtrate was washed with water, dried over magnesium sulfate, and then concentrated using a rotary evaporator. The residue was separated and purified by silica gel column chromatography (n-hexane/benzene=1/1) to obtain 1.29 g of crystals of the target product (yield: 72.9%).

$^1$H-NMR (400 MHz, CDCl$_3$, δ): 8.18 (d, 2H), 7.54 (d, 2H), 3.96 (s, 3H)

Example 20

[Synthesis of 4'-cyano-2',3',5',6'-tetrakis(3,6-di-tert-butyl-9H-carbazol-9-yl)-[1,1'-biphenyl]-4-carboxylic acid methyl ester (4X-BCz-PBN-CO$_2$Me)]

[Chemical formula 191]

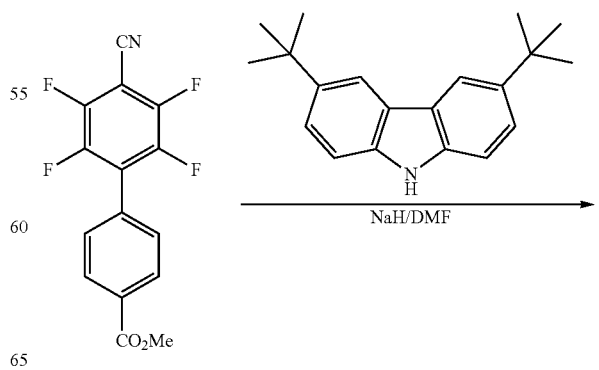

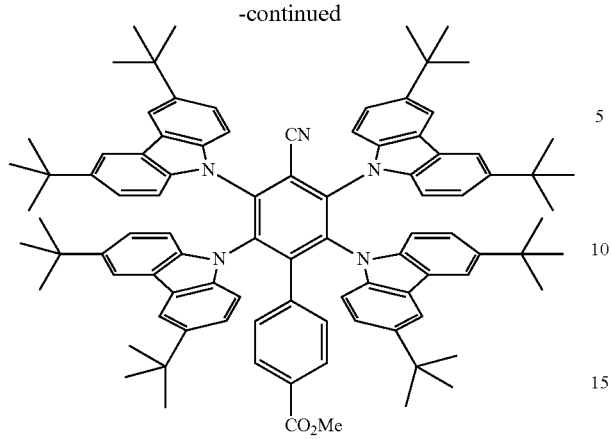

A 100 mL round-bottom flask was charged with 4-(4-methoxycarbonylphenyl)-2,3,5,6-tetrafluorobenzonitrile (0.50 g, 1.78 mmol), 3,6-di-t-butyl-carbazole (2.24 g, 8.01 mmol) and 20 ml of anhydrous DMF, and the resulting mixture was cooled in an ice bath. Subsequently, 60% sodium hydride (0.36 g, 8.90 mmol) was added gradually to the flask, and the resulting mixture was then stirred at room temperature for 3 hours and then at 80° C. for 2 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=2/1). The thus obtained crystals were washed with 2-propanol to obtain 1.93 g of the target product (yield: 82.5%).

$^1$H-NMR (400 MHz, CDCl$_3$, δ): 7.54 (d, 4H), 7.43 (d, 4H), 6.93 (dd, 4H), 6.86 (d, 4H), 6.81 (dd, 6H), 6.63 (d, 4H), 6.06 (d, 2H), 3.23 (s, 3H), 1.34 (s, 36H), 1.30 (s, 36H)

[Evaluation of Light Emission]

Figure 13:
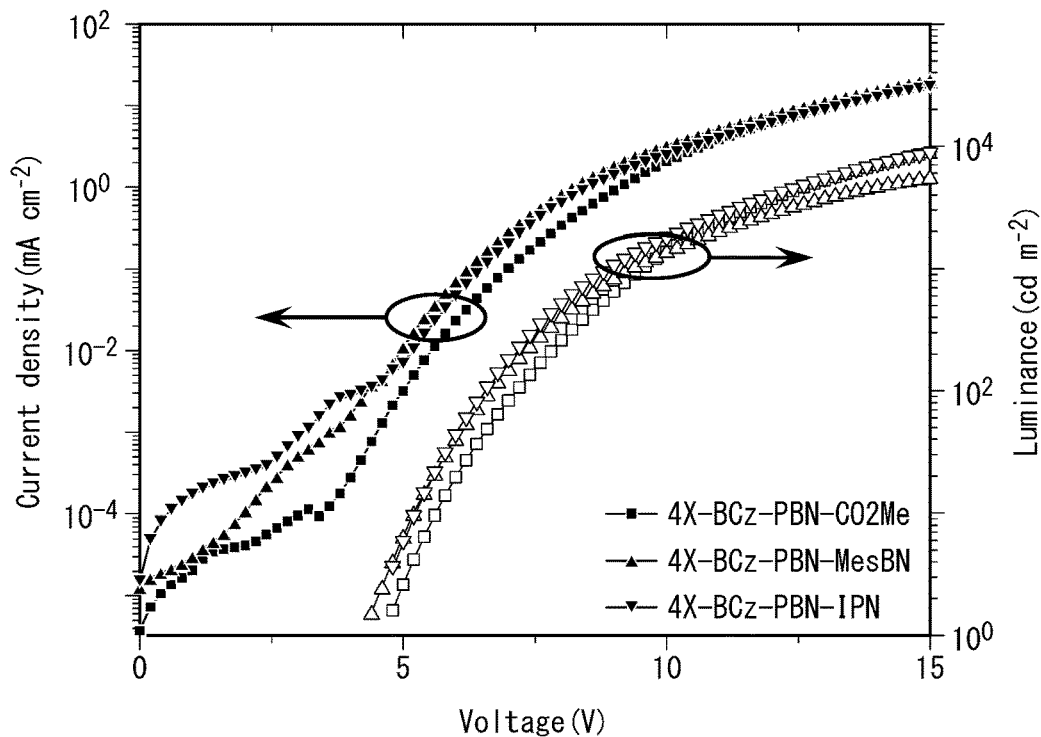
FIG. 13 is a diagram illustrating the voltage-current density-luminance characteristics for 4X-BCz-PBN-CO2Me, 4X-BCz-PBN-MesBN and 4X-BCz-PBN-IPN.
Figure 14:
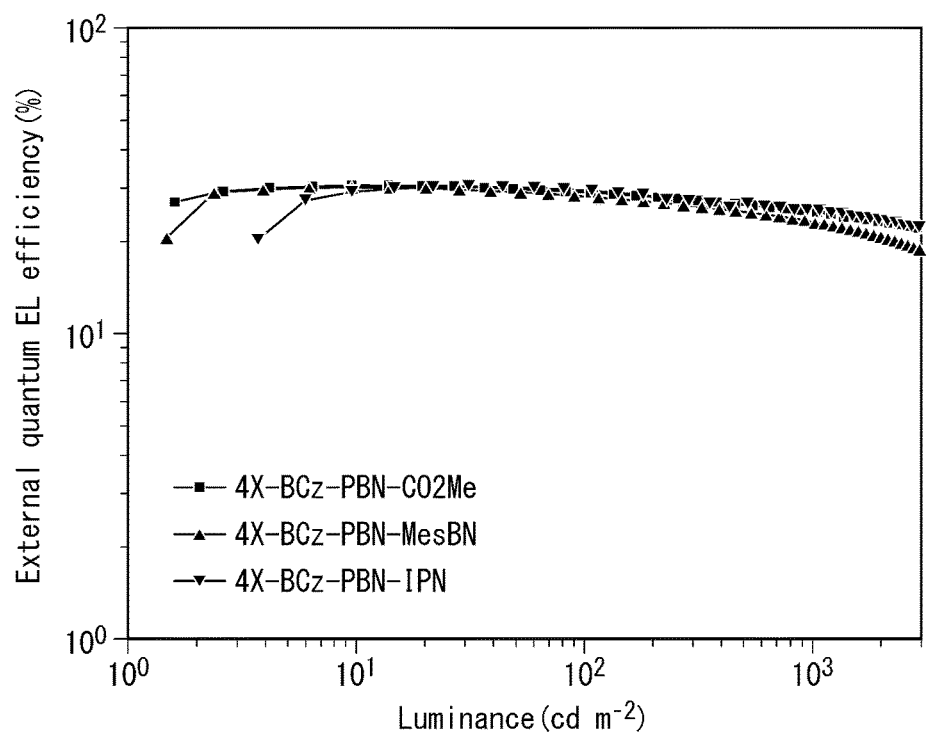
FIG. 14 is a diagram illustrating the luminance-external quantum efficiency characteristics for 4X-BCz-PBN-CO2Me, 4X-BCz-PBN-MesBN and 4X-BCz-PBN-IPN.

With the exception of altering the dopant to 4'-cyano-2', 3',5',6'-tetrakis(3,6-di-tert-butyl-9H-carbazol-9-yl)-[1,1'-biphenyl]-4-carboxylic acid methyl ester (4X-BCz-PBN-CO$_2$Me), a light emission evaluation was conducted using the same method as Example 1. The results are shown in FIGS. 13 and 14. EQEmax was 30.4%.

Example 21

Synthesis of 4X-BCz-PBN-MesBN

[Chemical formula 192]

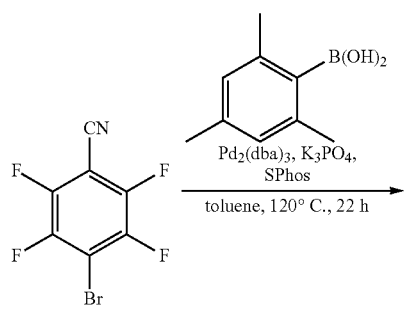

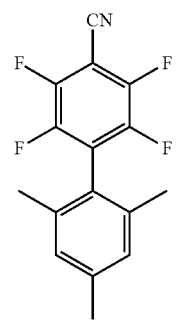

A 200 mL three-neck flask was charged with 2,4,6-trimethylphenylboronic acid (2.62 g, 16.0 mmol), 4-bromo-2,3,5,6-tetrafluorobenzonitrile (2.03 g, 8.0 mmol), potassium phosphate (6.80 g, 32.0 mmol), tris(dibenzylideneacetone)dipalladium(0) (0.37 g, 0.40 mmol), SPhos (0.66 g, 1.61 mmol) and 100 mL of anhydrous toluene, and following degassing and flushing of the flask with nitrogen, the mixture was stirred at 120° C. for 22 hours. The reaction liquid was then returned to room temperature, toluene was added, and the insoluble matter was removed by filtration using celite. The filtrate was concentrated, and the resulting residue was purified by silica gel column chromatography (n-hexane/dichloromethane) to obtain 1.09 g of a colorless oily precursor (yield: 46.5%)

$^1$H-NMR (400 MHz, CDCl$_3$, δ): 7.01 (s, 2H), 2.35 (s, 3H), 2.05 (s, 6H)

[Chemical formula 193]

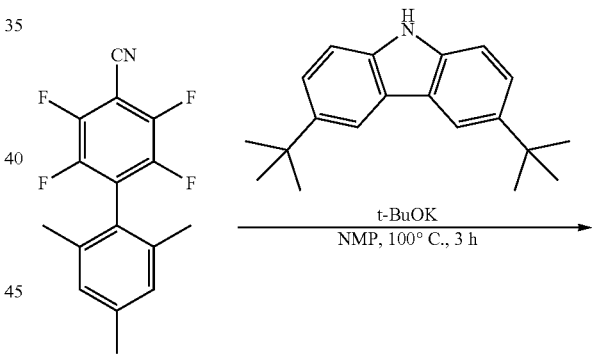

In a 200 mL three-neck flask that had been flushed with nitrogen, 3,6-di-t-butylcarbazole (2.12 g, 7.6 mmol) was dissolved in 30 mL of anhydrous N-methyl-2-pyrrolidone, potassium t-butoxide (0.82 g, 7.3 mmol) was added, and the resulting mixture was stirred at room temperature for one hour. The mixture was cooled in an ice bath, a solution containing the precursor (0.50 g, 1.70 mmol) dissolved in 5 mL of anhydrous N-methyl-2 pyrrolidone was added to the flask under a stream of nitrogen, and the resulting mixture was then stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. Ethyl acetate was added to the residue, the mixture was subjected to ultrasonic irradiation, the precipitated solid was collected by filtration, and the solvent was removed by distillation to obtain 2.05 g of a light yellow-green solid of the target product (yield: 90.3%).

$^1$H-NMR (400 MHz, CDCl$_3$, δ): 7.52 (d, J=1.6 Hz, 4H), 7.38 (s, 4H), 6.89 (dd, J=8.4 Hz, 2.0 Hz, 4H), 6.81 (d, J=8.8 Hz, 4H), 6.73 to 6.68 (m, 8H), 6.26 (s, 2H), 2.17 (s, 6H), 1.70 (s, 3H), 1.35 (s, 36H), 1.30 (s, 36H)

[Evaluation of Light Emission]

With the exception of altering the dopant to 4X-BCz-PBN-MesBN a light emission evaluation was conducted using the same method as Example 1. The results are shown in FIGS. 13 and 14. EQEmax was 29.5%.

Example 22

Synthesis of 4X-BCz-PBN-IPN

[Chemical formula 194]

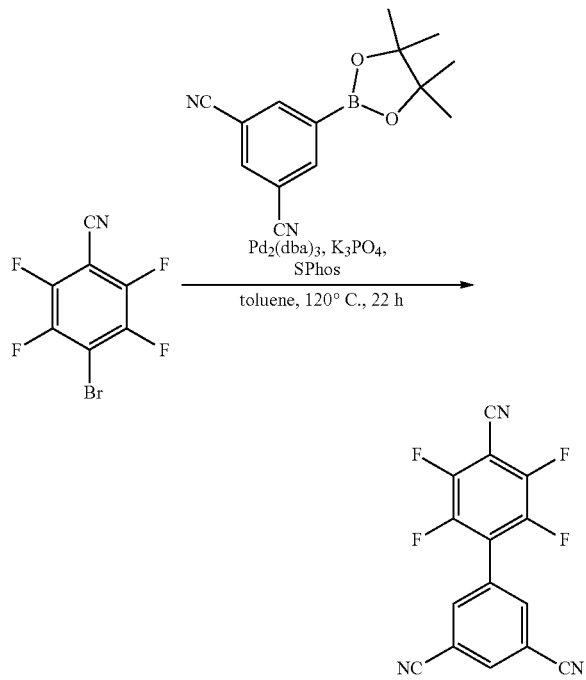

A 200 mL three-neck flask was charged with 3,5-dicyanophenylboronic acid pinacol ester (0.51 g, 2.0 mmol), 4-bromo-2,3,5,6-tetrafluorobenzonitrile (0.62 g, 2.4 mmol), potassium phosphate (1.69 g, 8.0 mmol), tris(dibenzylideneacetone)dipalladium(0) (90.2 mg, 0.10 mmol), SPhos (162.8 mg, 0.40 mmol) and 25 mL of anhydrous toluene, and following degassing and flushing of the flask with nitrogen, the mixture was stirred at 120° C. for 22 hours. The reaction liquid was then returned to room temperature, toluene was added, and the insoluble matter was removed by filtration using celite. The filtrate was concentrated, and the resulting residue was purified by silica gel column chromatography (n-hexane/ethyl acetate) to obtain 0.18 g of a precursor in the form of a light yellow-white solid (yield: 30.4%)

$^1$H-NMR (400 MHz, CDCl$_3$, δ): 8.12 (t, J=1.2 Hz, 1H), 8.00 (d, J=1.2 Hz, 2H)

[Chemical formula 195]

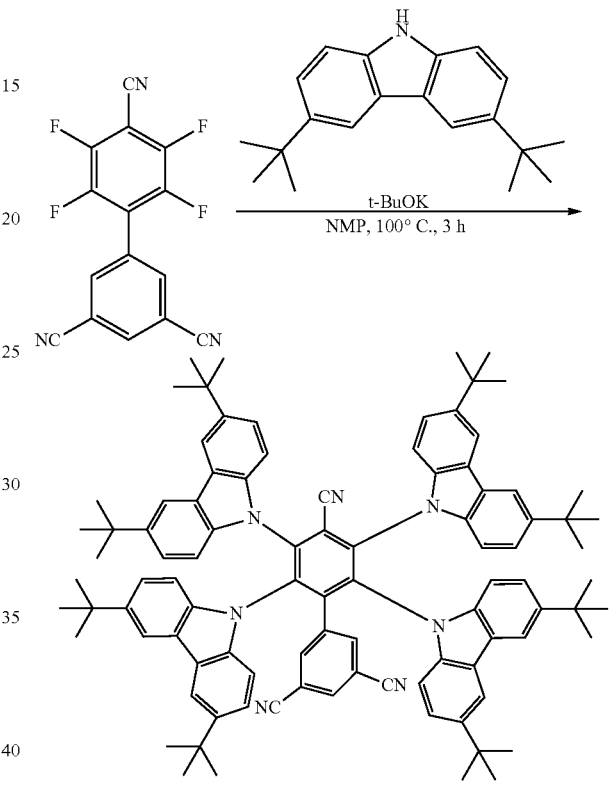

In a 200 mL three-neck flask that had been flushed with nitrogen, 3,6-di-t-butylcarbazole (1.84 g, 6.6 mmol) was dissolved in 27 mL of anhydrous N-methyl-2-pyrrolidone, potassium t-butoxide (0.71 g, 6.3 mmol) was added, and the resulting mixture was stirred at room temperature for one hour. The mixture was cooled in an ice bath, a solution containing the precursor (0.45 g, 1.49 mmol) dissolved in 5 mL of anhydrous N-methyl-2 pyrrolidone was added to the flask under a stream of nitrogen, and the resulting mixture was then stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. The residue was purified by silica gel column chromatography (n-hexane/benzene) to obtain a crudely purified product. Subsequently, n-hexane was added to this crudely purified product, the mixture was subjected to ultrasonic irradiation, the precipitated solid was collected by filtration, and the solvent was removed by distillation to obtain 1.24 g of a yellow solid of the target product (yield: 62.0%).

$^1$H-NMR (400 MHz, CDCl$_3$, δ): 7.64 (d, J=1.6 Hz, 4H), 7.50 (d, J=1.6 Hz, 4H), 7.12 (d, J=1.2 Hz, 2H), 7.07 (dd, J=8.8 Hz, 2.0 Hz, 4H), 7.02 to 6.96 (m, 9H), 6.67 (d, J=8.4 Hz, 4H), 1.36 (s, 36H), 1.32 (s, 36H)

[Evaluation of Light Emission]

With the exception of altering the dopant to 4X-BCz-PBN-IPN a light emission evaluation was conducted using the same method as Example 1. The results are shown in FIGS. 13 and 14. EQEmax was 31.0%.

Synthesis Example 23

Synthesis of 2,3,5,6-tetrafluoro-4-(pyridin-2-yl)benzonitrile

[Chemical formula 196]

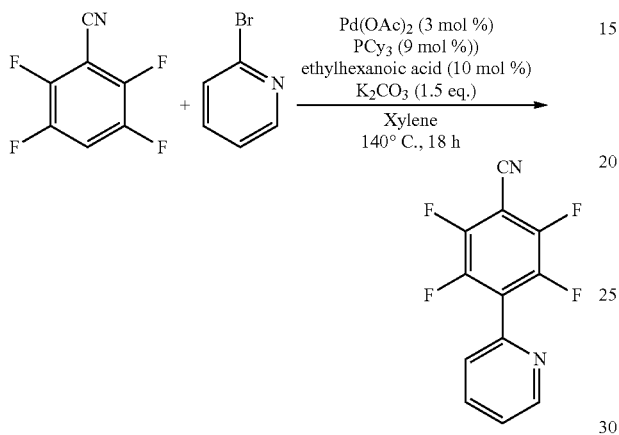

A 50 mL round-bottom flask was charged with 2,3,5,6-tetrafluorobenzonitrile (0.50 g, 2.86 mmol), 2-bromopyridine (0.47 g, 3.0 mmol), 2-ethylhexanoic acid (41.0 mg, 0.29 mmol), potassium carbonate (0.59 g, 4.29 mmol) and 10 ml of xylene. The flask was then degassed and flushed with argon, tricyclohexylphosphine (0.45 ml of a 20% toluene solution, 0.25 mmol) and palladium acetate (19.2 mg, 0.09 mmol) were then added, and the resulting mixture was stirred at 140° C. for 18 hours. The reaction liquid was then returned to room temperature, ethyl acetate was added, and the insoluble matter was removed by filtration. The filtrate was then washed with water, dried over magnesium sulfate and then concentrated using a rotary evaporator. The residue was separated and purified by silica gel column chromatography (n-hexane/ethyl acetate=7/3) to obtain 0.56 g of crystals of the target product (yield: 77.8%).

$^1$H-NMR (400 MHz, CDCl$_3$, δ): 8.80 (d, 1H), 7.88 (m, 1H), 7.51 (d, 1H), 7.45 (m, 1H)

Example 23

Synthesis of 2,3,5,6-tetrakis(3,6-di-tert-butyl-9H-carbazol-9-yl)-4-(pyridin-2-yl)benzonitrile (4X-BCz-PBN-2-Py)

[Chemical formula 197]

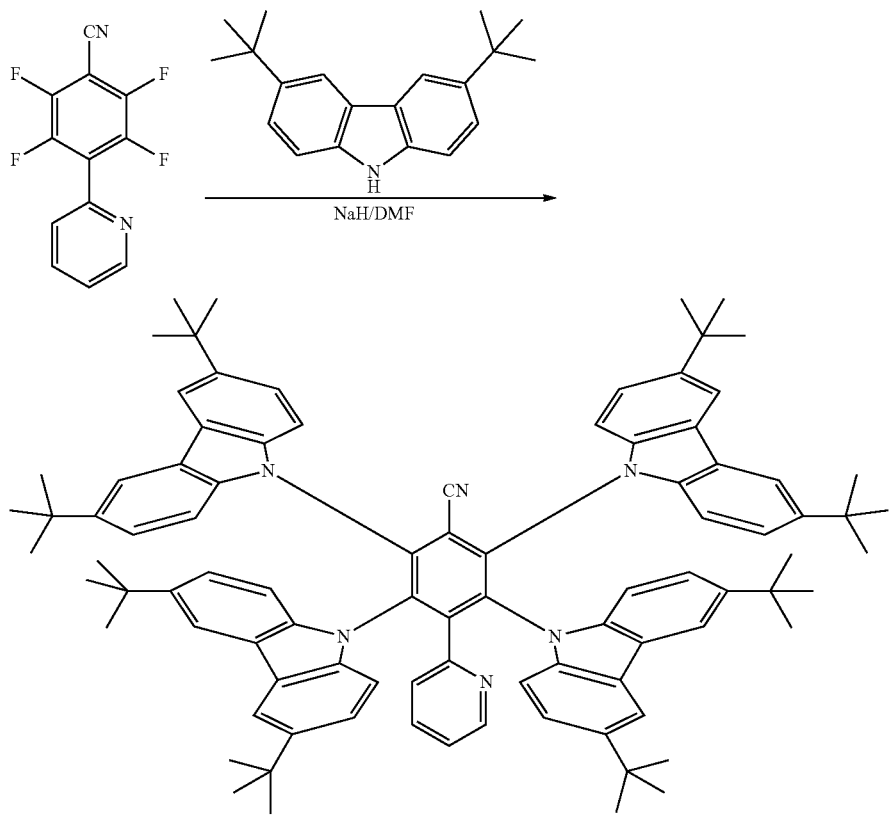

A 100 mL round-bottom flask was charged with 2,3,5,6-tetrafluoro-4-(pyridin-2-yl)benzonitrile (0.50 g, 1.98 mmol), 3,6-di-t-butyl-carbazole (2.49 g, 8.91 mmol) and 20 ml of anhydrous DMF, and the resulting mixture was cooled in an ice bath. Subsequently, 60% sodium hydride (0.40 g, 9.90 mmol) was added gradually to the flask, and the resulting mixture was then stirred at room temperature for 5 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=2/1). The thus obtained crystals were washed with 2-propanol to obtain 2.26 g of the target product (yield: 89.0%).

$^1$H-NMR (400 MHz, CDCl$_3$, δ): 7.84 (d, 1H), 7.56 (d, 4H), 7.42 (d, 4H), 6.98 to 6.95 (m, 5H), 6.92 (d, 4H), 6.86 to 6.83 (m, 5H), 6.77 (d, 4H), 6.43 (dd, 1H), 1.36 (s, 36H), 1.30 (s, 36H)

[Evaluation of Light Emission]

Figure 15:
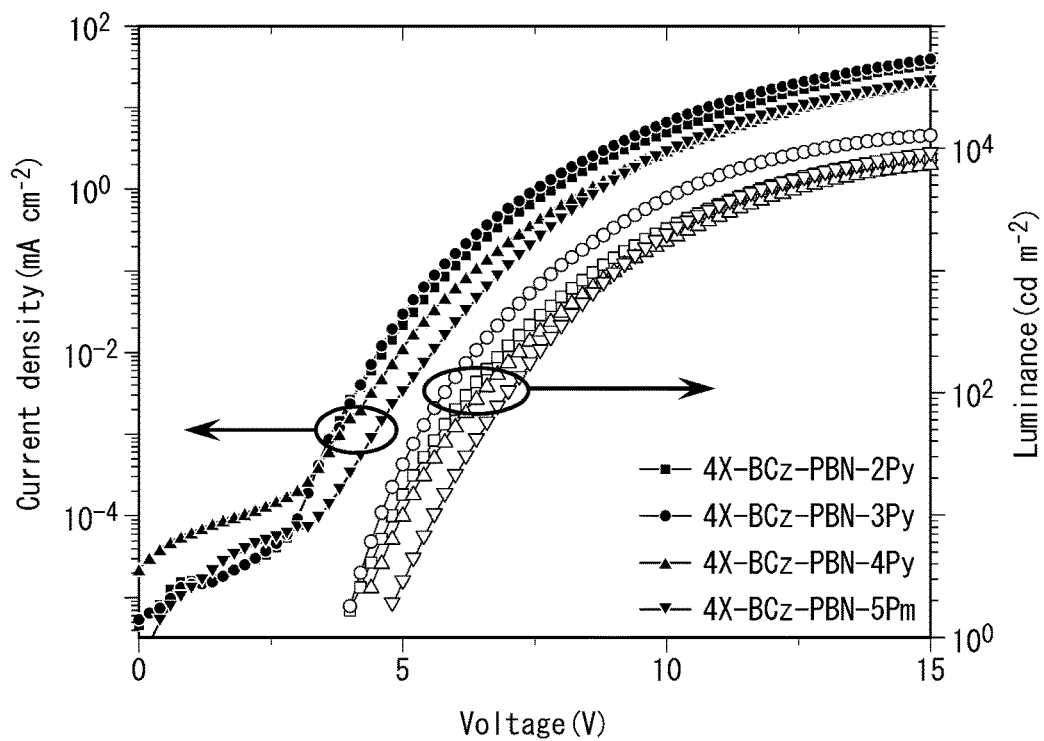
FIG. 15 is a diagram illustrating the voltage-current density-luminance characteristics for 4X-BCz-PBN-2Py, 4X-BCz-PBN-3Py, 4X-BCz-PBN-4Py and 4X-BCz-PBN-5Pm.
Figure 16:
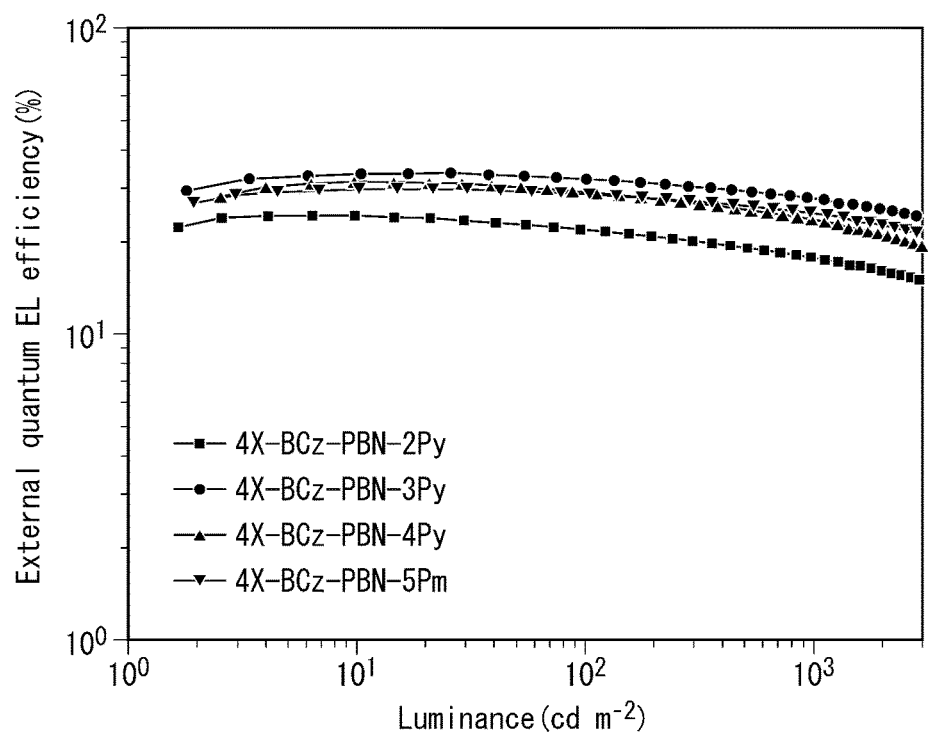
FIG. 16 is a diagram illustrating the luminance-external quantum efficiency characteristics for 4X-BCz-PBN-2Py, 4X-BCz-PBN-3Py, 4X-BCz-PBN-4Py and 4X-BCz-PBN-5Pm.

With the exception of altering the dopant to 2,3,5,6-tetrakis(3,6-di-tert-butyl-9H-carbazol-9-yl)-4-(pyridin-2-yl)benzonitrile (4X-BCz-PBN-2-Py), a light emission evaluation was conducted using the same method as Example 1. The results are shown in FIGS. 15 and 16. EQEmax was 24.4%.

Synthesis Example 24

Synthesis of 2,3,5,6-tetrafluoro-4-(pyridin-3-yl)benzonitrile

[Chemical formula 198]

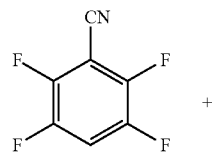

+

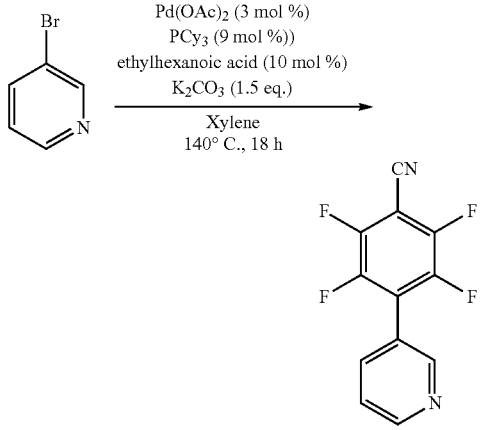

A 100 mL round-bottom flask was charged with 2,3,5,6-tetrafluorobenzonitrile (1.15 g, 6.57 mmol), 3-bromopyridine (1.09 g, 6.90 mmol), 2-ethylhexanoic acid (95 mg, 0.66 mmol), potassium carbonate (1.36 g, 9.86 mmol) and 20 ml of xylene. The flask was then degassed and flushed with argon, tricyclohexylphosphine (1.04 ml of a 20% toluene solution, 0.59 mmol) and palladium acetate (44.0 mg, 0.18 mmol) were then added, and the resulting mixture was stirred at 140° C. for 18 hours. The reaction liquid was then returned to room temperature, ethyl acetate was added, and the insoluble matter was removed by filtration. The filtrate was then washed with water, dried over magnesium sulfate and then concentrated using a rotary evaporator. The residue was separated and purified by silica gel column chromatography (n-hexane/ethyl acetate=7/3) to obtain 1.16 g of crystals of the target product (yield: 69.9%).

$^1$H-NMR (400 MHz, CDCl$_3$, δ): 8.76 to 8.73 (m, 2H), 7.80 (d, 1H), 7.50 to 7.47 (t, 1H)

Example 24

Synthesis of 2,3,5,6-tetrakis(3,6-di-tert-butyl-9H-carbazol-9-yl)-4-(pyridin-3-yl)benzonitrile (4X-BCz-PBN-3-Py)

[Chemical formula 199]

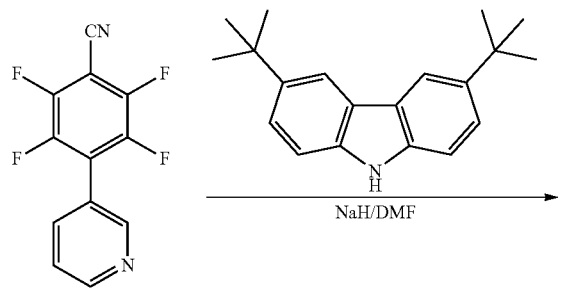

-continued

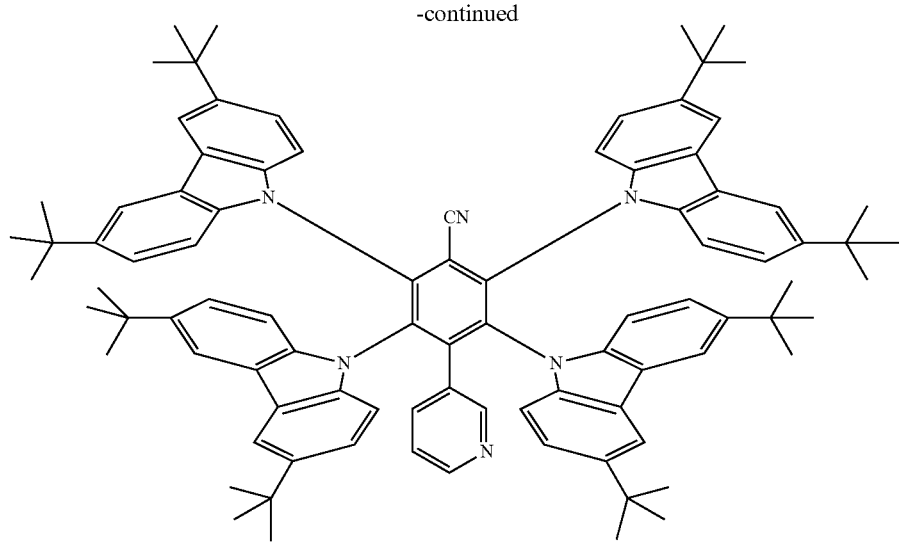

A 100 mL round-bottom flask was charged with 2,3,5,6-tetrafluoro-4-(pyridin-3-yl)benzonitrile (0.50 g, 1.98 mmol), 3,6-di-t-butyl-carbazole (2.49 g, 8.91 mmol) and 20 ml of anhydrous DMF, and the resulting mixture was cooled in an ice bath. Subsequently, 60% sodium hydride (0.40 g, 9.90 mmol) was added gradually to the flask, and the resulting mixture was then stirred at room temperature for 4.5 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=2/3). The thus obtained crystals were washed with 2-propanol to obtain 2.18 g of the target product (yield: 85.8%).

$^1$H-NMR (400 MHz, CDCl$_3$, δ): 8.22 (d, 1H), 7.81 (d, 1H), 7.57 (d, 4H), 7.45 (d, 4H), 7.23 (d, 1H), 6.96 (dd, 4H), 6.89 (d, 4H), 6.84 (dd, 4H), 6.62 (d, 4H), 6.49 (dd, 1H), 1.36 (s, 36H), 1.31 (s, 36H)

[Evaluation of Light Emission]

With the exception of altering the dopant to 2,3,5,6-tetrakis(3,6-di-tert-butyl-9H-carbazol-9-yl)-4-(pyridin-3-yl)benzonitrile (4X-BCz-PBN-3-Py), a light emission evaluation was conducted using the same method as Example 1. The results are shown in FIGS. 15 and 16. EQEmax was 33.6%.

Synthesis Example 25

Synthesis of 2,3,5,6-tetrafluoro-4-(pyridin-4-yl)benzonitrile

[Chemical formula 200]

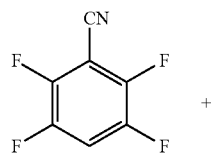

+

-continued

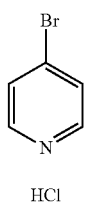
HCl

Pd(OAc)$_2$ (3 mol %)
PCy$_3$ (9 mol %))
ethylhexanoic acid (10 mol %)
K$_2$CO$_3$ (2.5 eq.)

Xylene
140° C., 17 h

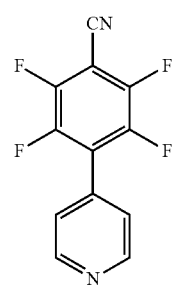

A 50 mL round-bottom flask was charged with 2,3,5,6-tetrafluorobenzonitrile (0.80 g, 4.57 mmol), 4-bromopyridine hydrochloride (0.93 g, 4.80 mmol), 2-ethylhexanoic acid (66.0 mg, 0.46 mmol), potassium carbonate (1.58 g, 11.4 mmol) and 15 ml of xylene. The flask was then degassed and flushed with argon, tricyclohexylphosphine (0.72 ml of a 20% toluene solution, 0.41 mmol) and palladium acetate (31.0 mg, 0.14 mmol) were then added, and the resulting mixture was stirred at 140° C. for 17 hours. The reaction liquid was then returned to room temperature, ethyl acetate was added, and the insoluble matter was removed by filtration. The filtrate was then washed with water, dried over magnesium sulfate and then concentrated using a rotary evaporator. The residue was separated and purified by silica gel column chromatography (n-hexane/benzene=1/4) to obtain 0.70 g of crystals of the target product (yield: 60.9%).

$^1$H-NMR (400 MHz, CDCl$_3$, δ): 8.81 (d, 2H), 7.38 (d, 2H)

Example 25

Synthesis of 2,3,5,6-tetrakis(3,6-di-tert-butyl-9H-carbazol-9-yl)-4-(pyridin-4-yl)benzonitrile (4X-BCz-PBN-4-Py)

[Chemical formula 201]

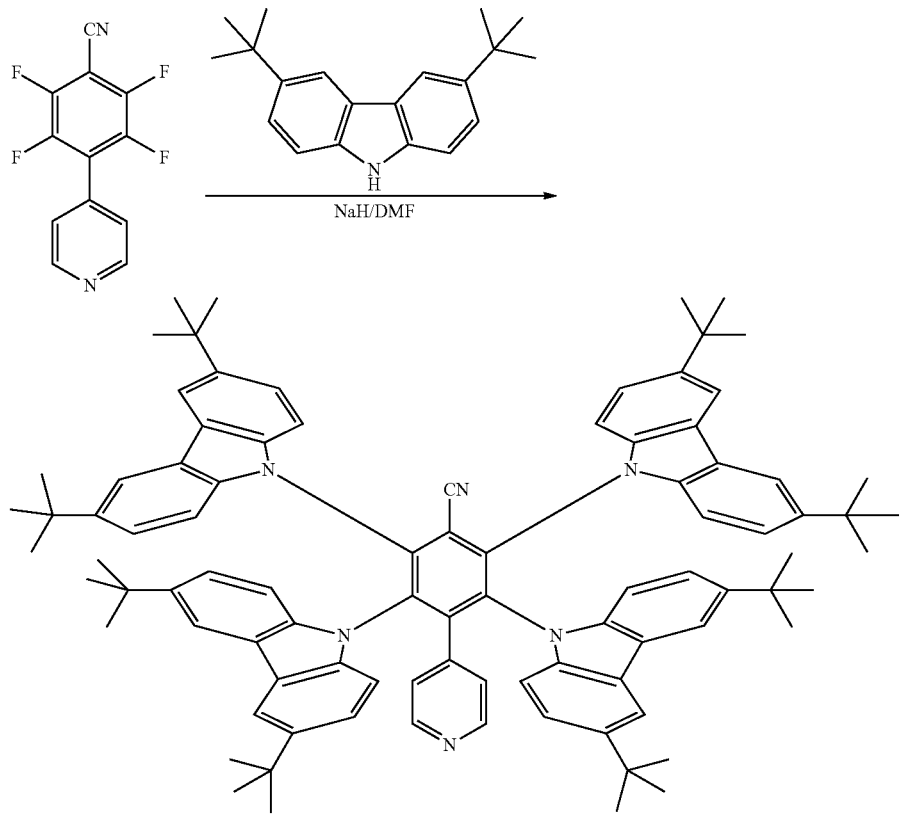

A 100 mL round-bottom flask was charged with 2,3,5,6-tetrafluoro-4-(pyridin-4-yl)benzonitrile (0.50 g, 1.98 mmol), 3,6-di-t-butyl-carbazole (2.49 g, 8.91 mmol) and 20 ml of anhydrous DMF, and the resulting mixture was cooled in an ice bath. Subsequently, 60% sodium hydride (0.40 g, 9.90 mmol) was added gradually to the flask, and the resulting mixture was then stirred at room temperature for 5 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (benzene). The thus obtained crystals were washed with 2-propanol to obtain 2.24 g of the target product (yield: 88.2%).

$^1$H-NMR (400 MHz, CDCl$_3$, δ): 7.82 (d, 2H), 7.56 (d, 4H), 7.45 (d, 4H), 6.95 (dd, 4H), 6.87 to 6.82 (m, 10H), 6.62 (d, 4H), 1.35 (s, 36H), 1.31 (s, 36H)

[Evaluation of Light Emission]

With the exception of altering the dopant to 2,3,5,6-tetrakis(3,6-di-tert-butyl-9H-carbazol-9-yl)-4-(pyridin-4-yl)benzonitrile (4X-BCz-PBN-4-Py), a light emission evaluation was conducted using the same method as Example 1. The results are shown in FIGS. 15 and 16. EQEmax was 30.9%.

Synthesis Example 26

Synthesis of 2,3,5,6-tetrafluoro-4-(pyrimidin-5-yl)benzonitrile

[Chemical formula 202]

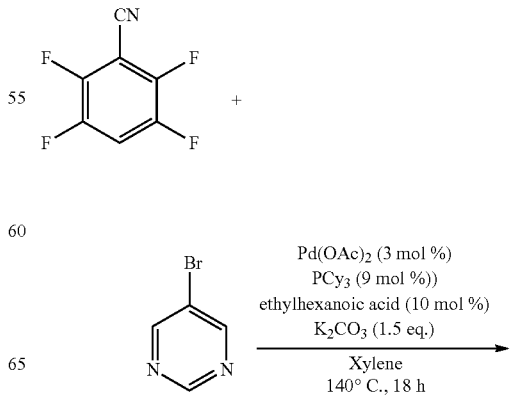

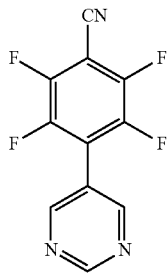

A 100 mL round-bottom flask was charged with 2,3,5,6-tetrafluorobenzonitrile (1.00 g, 5.71 mmol), 5-bromopyrimidine (0.95 g, 6.00 mmol), 2-ethylhexanoic acid (82.0 mg, 0.57 mmol), potassium carbonate (1.18 g, 8.57 mmol) and 20 ml of xylene. The flask was then degassed and flushed with argon, tricyclohexylphosphine (0.90 ml of a 20% toluene solution, 0.50 mmol) and palladium acetate (38.52 mg, 0.18 mmol) were then added, and the resulting mixture was stirred at 140° C. for 18 hours. The reaction liquid was then returned to room temperature, ethyl acetate was added, and the insoluble matter was removed by filtration. The filtrate was then washed with water, dried over magnesium sulfate and then concentrated using a rotary evaporator. The residue was separated and purified by silica gel column chromatography (n-hexane/ethyl acetate=7/3) to obtain 0.96 g of crystals of the target product (yield: 66.5%).

$^1$H-NMR (400 MHz, CDCl$_3$, δ): 9.35 (s, 1H), 8.91 (s, 2H)

Example 26

Synthesis of 2,3,5,6-tetrakis(3,6-di-tert-butyl-9H-carbazol-9-yl)-4-(pyrimidin-5-yl)benzonitrile (4X-BCz-PBN-5-Pm)

[Chemical formula 203]

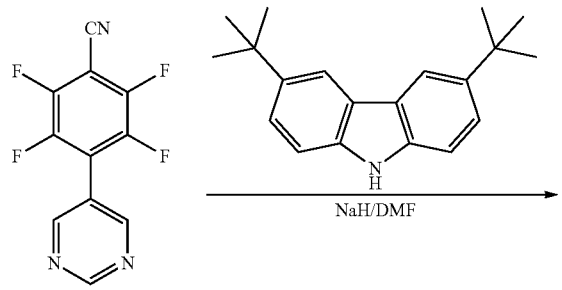

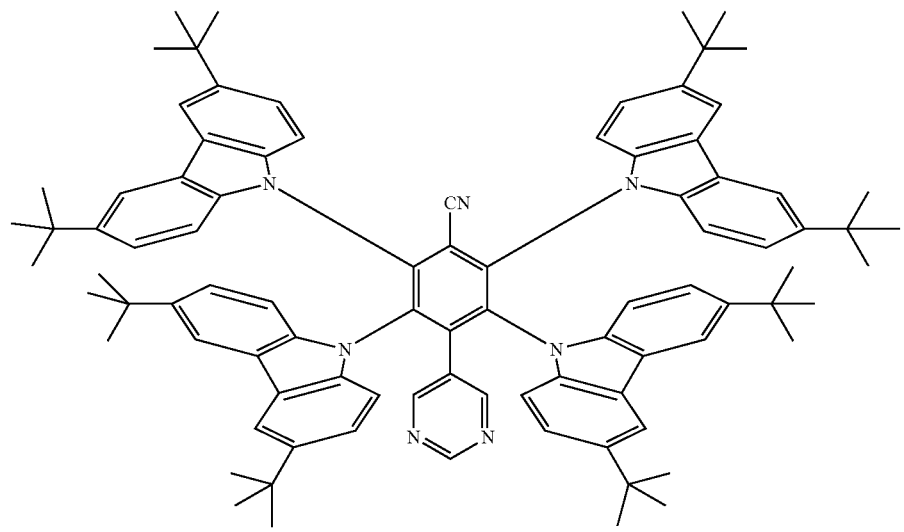

A 100 mL round-bottom flask was charged with 2,3,5,6-tetrafluoro-4-(pyrimidin-5-yl)benzonitrile (0.50 g, 1.98 mmol), 3,6-di-t-butyl-carbazole (2.48 g, 8.91 mmol) and 20 ml of anhydrous DMF, and the resulting mixture was cooled in an ice bath. Subsequently, 60% sodium hydride (0.40 g, 9.90 mmol) was added gradually to the flask, and the resulting mixture was then stirred at room temperature for 4 hours. The reaction liquid was then poured into ice water, and the precipitated crystals were collected by filtration. The crystals were then dissolved in ether, washed with water, dried over magnesium sulfate, and concentrated. The residue was separated and purified by silica gel chromatography (n-hexane/benzene=2/3). The thus obtained crystals were washed with 2-propanol to obtain 2.23 g of the target product (yield: 87.8%).

$^1$H-NMR (400 MHz, CDCl$_3$, δ): 8.39 (s, 1H), 8.27 (s, 2H), 7.57 (d, 4H), 7.47 (d, 4H), 6.97 (dd, 4H), 6.90 (d, 4H), 6.86 (dd, 4H), 6.59 (d, 4H), 1.36 (s, 36H), 1.31 (s, 36H)

[Evaluation of Light Emission]

With the exception of altering the dopant to 2,3,5,6-tetrakis(3,6-di-tert-butyl-9H-carbazol-9-yl)-4-(pyrimidin-5-yl)benzonitrile (4X-BCz-PBN-5-Pm), a light emission evaluation was conducted using the same method as Example 1. The results are shown in FIGS. 15 and 16. EQEmax was 30.3%.

Example 27

Synthesis of 3Y-BCz-PBN-tBu

[Chemical formula 204]

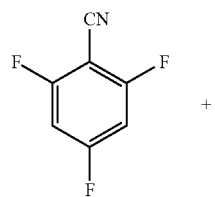

+

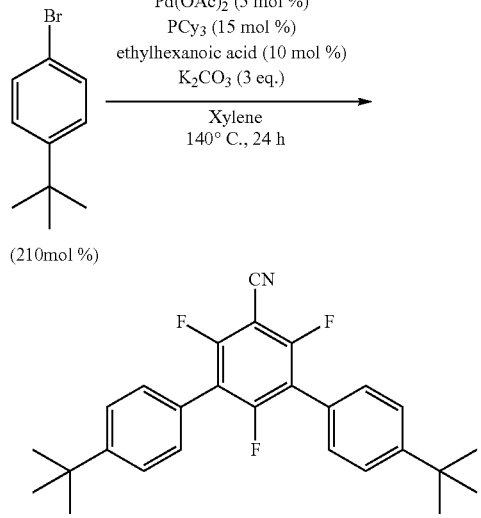

A 100 ml round-bottom flask was charged with 2,4,6-trifluorobenzonitrile (1.00 g, 6.4 mmol), 1-bromo-4-t-butyl-benzene (2.86 g, 13.4 mmol), 2-ethylhexanoic acid (93.8 mg, 0.65 mmol), potassium carbonate (2.64 g, 19.1 mmol) and 20 ml of anhydrous xylene. The flask was degassed and flushed with nitrogen, tricyclohexylphosphine (1.6 ml of a 20% toluene solution, 0.95 mmol) and palladium acetate (72.6 mg, 0.32 mmol) were then added, and the resulting mixture was stirred at 140° C. for 24 hours. The reaction liquid was then returned to room temperature, ethyl acetate was added, and the insoluble matter was removed by filtration using celite. The filtrate was washed with water, dried over magnesium sulfate, and then concentrated. The residue was purified by silica gel column chromatography (n-hexane/benzene) to obtain 1.44 g of a light brown, white solid of a precursor (yield: 53.7%).

$^1$H-NMR (400 MHz, CDCl$_3$, δ): 7.51 (d, J=8.0 Hz, 4H), 7.37 (d, J=8.4 Hz, 4H), 1.37 (s, 18H)

[Chemical formula 205]

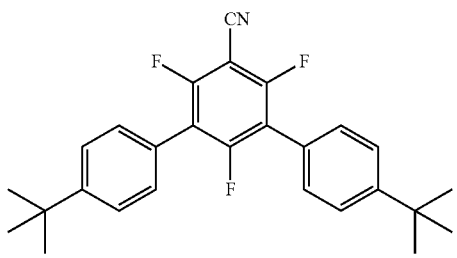

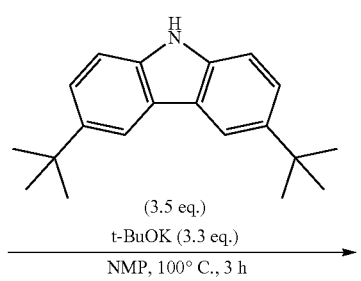

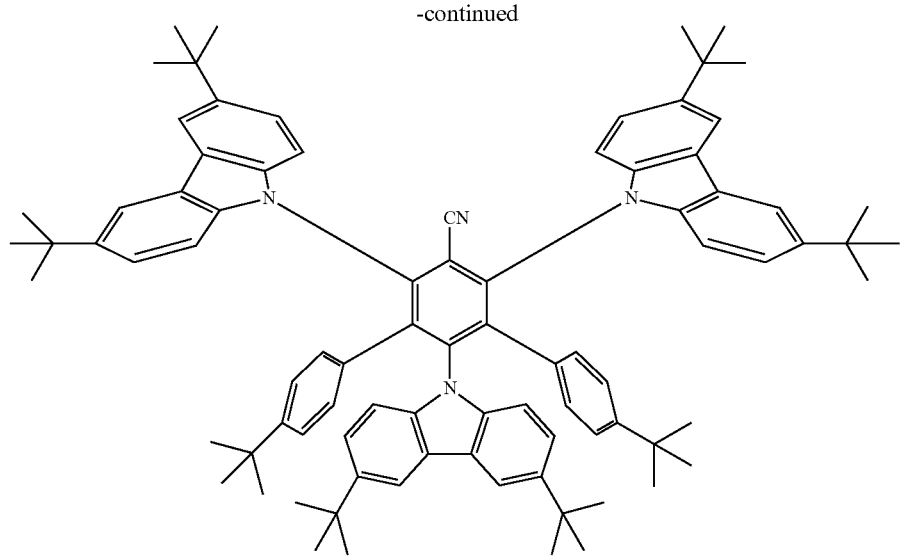

In a 200 mL three-neck flask that had been flushed with nitrogen, 3,6-di-t-butylcarbazole (1.16 g, 4.2 mmol) was dissolved in 24 mL of anhydrous N-methyl-2-pyrrolidone, potassium t-butoxide (0.44 g, 3.9 mmol) was then added, and the resulting mixture was stirred at room temperature for one hour. This mixture was then cooled in an ice bath, the precursor (0.50 g, 1.19 mmol) was added under a stream of nitrogen, and the resulting mixture was stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. The residue was purified by silica gel column chromatography (n-hexane/ethyl acetate) to obtain 0.81 g of crude crystals of the target product. Ethyl acetate was added to 3.28 g of the crude crystals prepared using the same method, the mixture was subjected to ultrasonic irradiation, the precipitated crystals were collected by filtration, and the solvent was removed by distillation to obtain 2.25 g of a light yellow-green solid of the target product (yield: 57.7%).

$^1$H-NMR (400 MHz, CDCl$_3$, δ): 7.94 (d, J=1.2 Hz, 4H), 7.71 (d, J=2.0 Hz, 2H), 7.38 (dd, J=8.8 Hz, 2.0 Hz, 4H), 7.21 (dd, J=8.8 Hz, 2.0 Hz, 2H), 7.10 (d, J=8.8 Hz, 4H), 6.93 (d, J=8.4 Hz, 2H), 6.43 (d, J=8.0 Hz, 4H), 6.33 (d, J=8.8 Hz, 4H), 1.39 (s, 36H), 1.31 (s, 18H), 0.77 (s, 18H)

[Evaluation of Light Emission]

Figure 17:
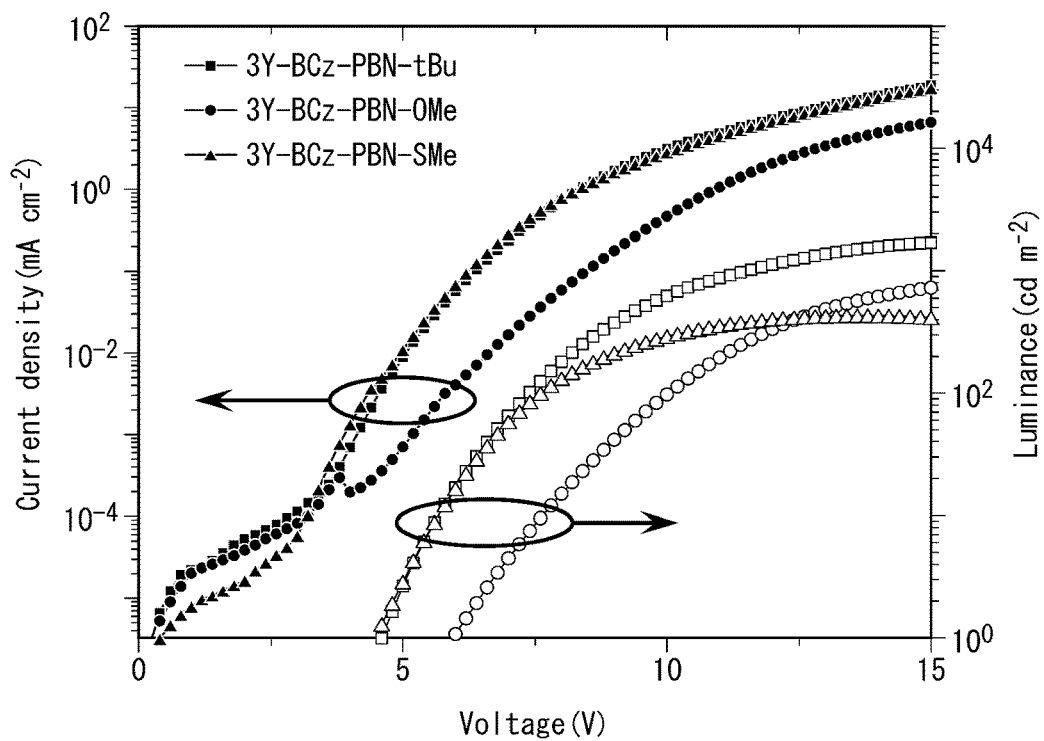
FIG. 17 is a diagram illustrating the voltage-current density-luminance characteristics for 3Y-BCz-PBN-tBu, 3Y-BCz-PBN-OMe and 3Y-BCz-PBN-SMe.
Figure 18:
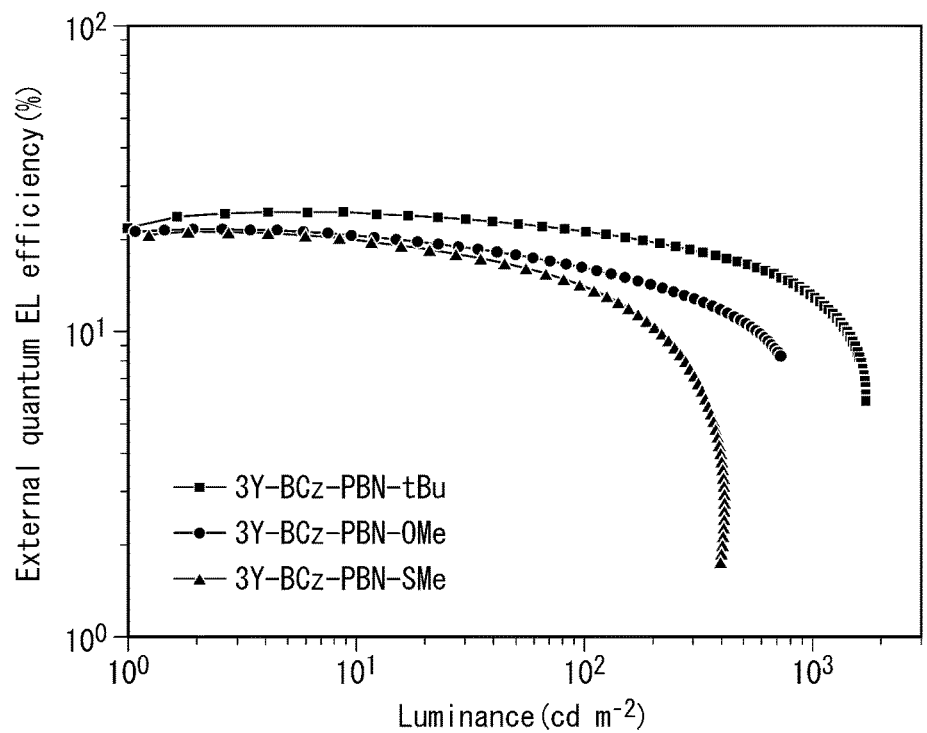
FIG. 18 is a diagram illustrating the luminance-external quantum efficiency characteristics for 3Y-BCz-PBN-tBu, 3Y-BCz-PBN-OMe and 3Y-BCz-PBN-SMe.

With the exception of altering the dopant to 3Y-BCz-PBN-tBu, a light emission evaluation was conducted using the same method as Example 1. The results are shown in FIGS. 17 and 18. EQEmax was 24.6%.

Example 28

Synthesis of 3Y-BCz-PBN-OMe

[Chemical formula 206]

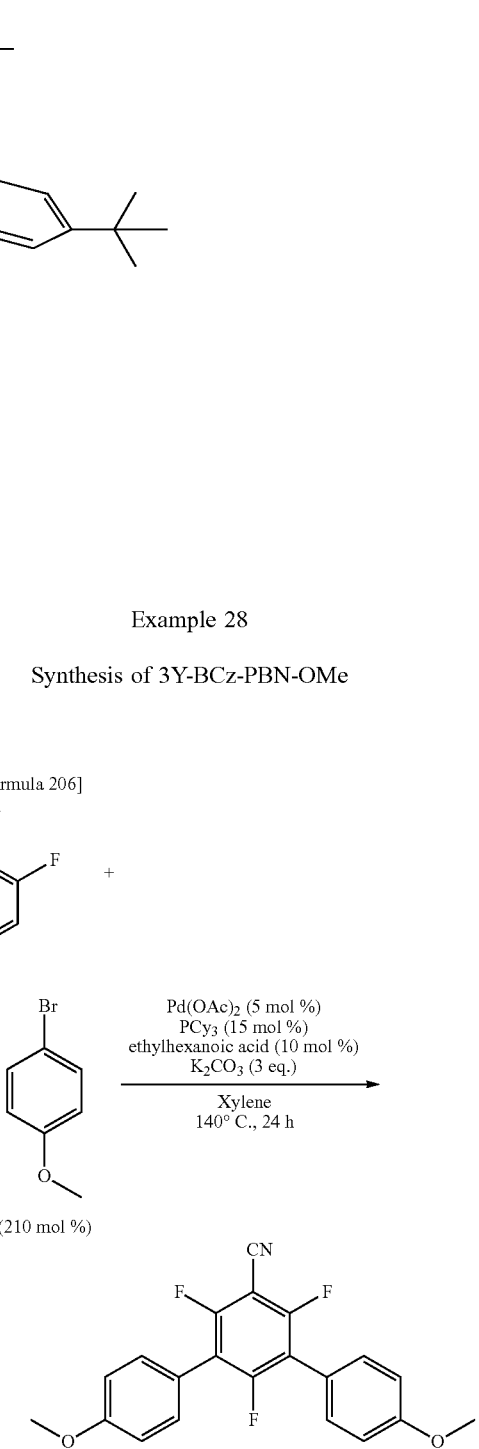

A 100 ml round-bottom flask was charged with 2,4,6-trifluorobenzonitrile (1.00 g, 6.4 mmol), 4-bromoanisole (2.51 g, 13.4 mmol), 2-ethylhexanoic acid (92.9 mg, 0.64 mmol), potassium carbonate (2.64 g, 19.1 mmol) and 20 ml of anhydrous xylene. The flask was degassed and flushed with nitrogen, tricyclohexylphosphine (1.6 ml of a 20% toluene solution, 0.95 mmol) and palladium acetate (72.4 mg, 0.32 mmol) were then added, and the resulting mixture was stirred at 140° C. for 24 hours. The reaction liquid was then returned to room temperature, ethyl acetate was added, and the insoluble matter was removed by filtration using celite. The filtrate was washed with water, dried over magnesium sulfate, and then concentrated. The residue was purified by silica gel column chromatography (n-hexane/benzene) to obtain 0.52 g of a white solid precursor (yield: 22.1%).

$^1$H-NMR (400 MHz, CDCl$_3$, δ): 7.37 (d, J=8.8 Hz, 4H), 7.03 to 7.00 (m, 4H), 3.87 (s, 6H)

$^1$H-NMR (400 MHz, CDCl$_3$, δ): 7.96 (d, J=2.0 Hz, 4H), 7.76 (d, J=2.0 Hz, 2H), 7.41 (dd, J=8.8 Hz, 2.0 Hz, 4H), 7.27 (dd, 2H), 7.11 (d, J=8.0 Hz, 4H), 6.96 (d, J=8.8 Hz, 2H), 6.52 (d, J=8.8 Hz, 4H), 5.92 (d, J=9.2 Hz, 4H), 3.29 (s, 6H), 1.40 (s, 36H), 1.33 (s, 18H)

[Evaluation of Light Emission]

With the exception of altering the dopant to 3Y-BCz-PBN-OMe, a light emission evaluation was conducted using the same method as Example 1. The results are shown in FIGS. 17 and 18. EQEmax was 21.5%.

[Chemical formula 207]

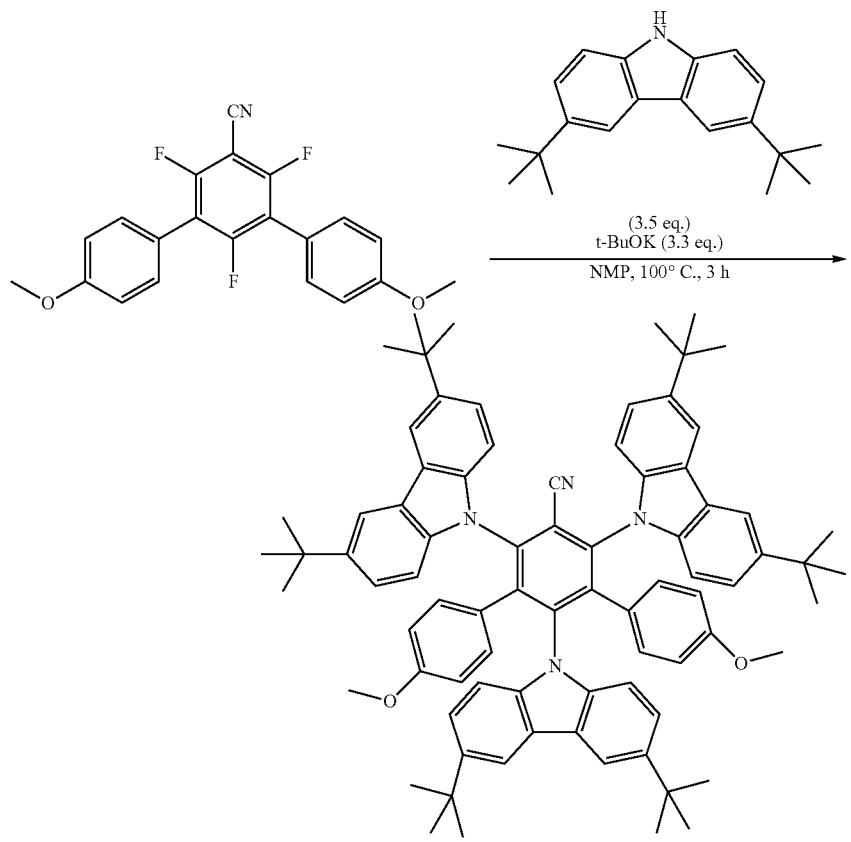

In a 200 mL three-neck flask that had been flushed with nitrogen, 3,6-di-t-butylcarbazole (1.33 g, 4.8 mmol) was dissolved in 20 mL of anhydrous N-methyl-2-pyrrolidone, potassium t-butoxide (0.44 g, 3.9 mmol) was then added, and the resulting mixture was stirred at room temperature for one hour. This mixture was then cooled in an ice bath, a solution containing the precursor (0.51 g, 1.35 mmol) dissolved in 7 mL of anhydrous N-methyl-2-pyrrolidone was added under a stream of nitrogen, and the resulting mixture was stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. The residue was purified by silica gel column chromatography (n-hexane/benzene) to obtain 1.63 g of a crudely purified product of the target product. Next, n-hexane/ethyl acetate was added to 3.33 g of the crudely purified product prepared using the same method, the mixture was subjected to ultrasonic irradiation, the precipitated crystals were collected by filtration, and the solvent was removed by distillation to obtain 2.37 g of the target product as a very light yellow white solid (yield: 74.1%).

Example 29

Synthesis of 3Y-BCz-PBN-SMe

[Chemical formula 208]

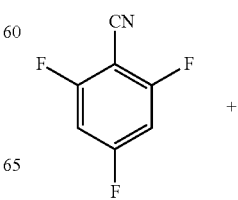

-continued

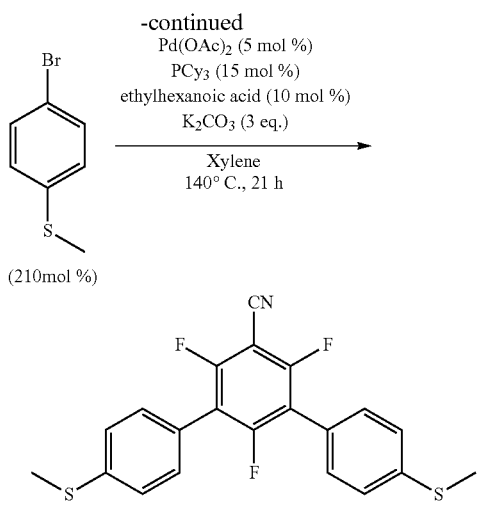

[Chemical formula 209]

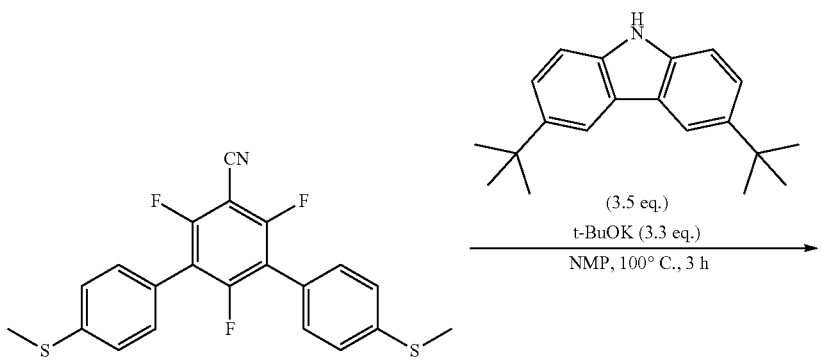

A 100 ml round-bottom flask was charged with 2,4,6-trifluorobenzonitrile (1.00 g, 6.4 mmol), 4-bromothioanisole (2.71 g, 13.3 mmol), 2-ethylhexanoic acid (94.3 mg, 0.65 mmol), potassium carbonate (2.66 g, 19.2 mmol) and 20 ml of anhydrous xylene. The flask was degassed and flushed with nitrogen, tricyclohexylphosphine (1.6 ml of a 20% toluene solution, 0.95 mmol) and palladium acetate (75.6 mg, 0.34 mmol) were then added, and the resulting mixture was stirred at 140° C. for 21 hours. The reaction liquid was then returned to room temperature, ethyl acetate was added, and the insoluble matter was removed by filtration using celite. The filtrate was washed with water, dried over magnesium sulfate, and then concentrated. The residue was purified by silica gel column chromatography (n-hexane/ethyl acetate) and then washed with n-hexane/ethyl acetate to obtain 1.43 g of a white solid precursor (yield: 56.0%).

$^1$H-NMR (400 MHz, CDCl$_3$, δ): 7.35 (s, 8H), 2.53 (s, 6H)

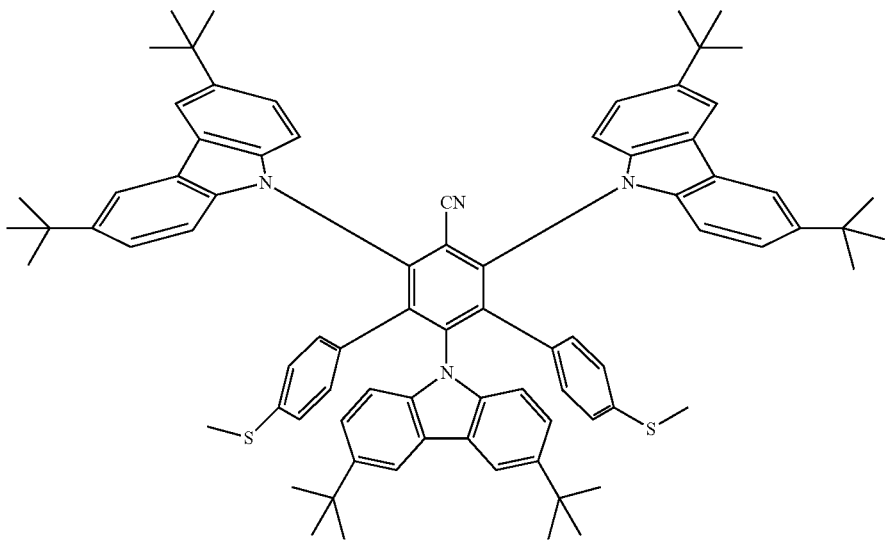

In a 200 mL three-neck flask that had been flushed with nitrogen, 3,6-di-t-butylcarbazole (1.95 g, 7.0 mmol) was dissolved in 32 mL of anhydrous N-methyl-2-pyrrolidone, potassium t-butoxide (0.76 g, 6.8 mmol) was then added, and the resulting mixture was stirred at room temperature for one hour. This mixture was then cooled in an ice bath, the precursor (0.80 g, 2.00 mmol) was added under a stream of nitrogen, and the resulting mixture was stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. The residue was purified by silica gel column chromatography (n-hexane/benzene) to obtain 2.25 g of a crudely purified product of the target product. Subsequently, n-hexane was added to the crudely purified product, the mixture was subjected to ultrasonic irradiation, the precipitated crystals were collected by filtration, and the solvent was removed by distillation to obtain 1.52 g of a light yellow white solid of the target product (yield: 64.7%).

$^1$H-NMR (400 MHz, CDCl$_3$, δ): 7.96 (d, J=2.0 Hz, 4H), 7.77 (d, J=2.0 Hz, 2H), 7.41 (dd, J=8.4 Hz, 2.0 Hz, 4H), 7.26 (dd, J=8.4 Hz, 2.0 Hz, 2H), 6.93 (d, J=8.0 Hz, 2H), 6.50 (d, J=8.4 Hz, 4H), 6.28 (d, J=8.4 Hz, 4H), 1.99 (s, 6H), 1.40 (s, 36H), 1.34 (s, 18H)

[Evaluation of Light Emission]

With the exception of altering the dopant to 3Y-BCz-PBN-SMe, a light emission evaluation was conducted using the same method as Example 1. The results are shown in FIGS. 17 and 18. EQEmax was 20.9%.

Example 30

Synthesis of 3F-BCz-PBN-tBu

[Chemical formula 210]

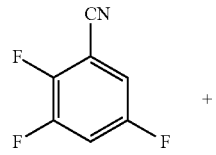
+
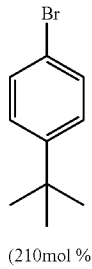
(210 mol %)

Pd(OAc)$_2$ (5 mol %)
PCy$_3$ (15 mol %)
ethylhexanoic acid (10 mol %)
K$_2$CO$_3$ (3 eq.)
───────────→
Xylene
140° C., 22 h

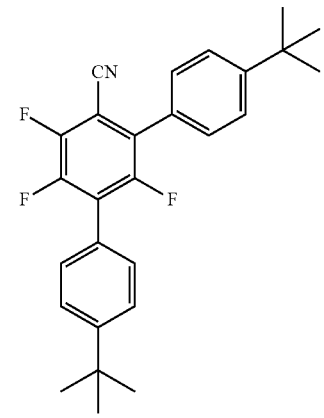

A 100 ml round-bottom flask was charged with 2,3,5-trifluorobenzonitrile (1.00 g, 6.4 mmol), 1-bromo-4-t-butyl-benzene (2.85 g, 13.4 mmol), 2-ethylhexanoic acid (94.7 mg, 0.66 mmol), potassium carbonate (2.64 g, 19.1 mmol) and 20 ml of anhydrous xylene. The flask was degassed and flushed with nitrogen, tricyclohexylphosphine (1.6 ml of a 20% toluene solution, 0.95 mmol) and palladium acetate (72.4 mg, 0.32 mmol) were then added, and the resulting mixture was stirred at 140° C. for 22 hours. The reaction liquid was then returned to room temperature, ethyl acetate was added, and the insoluble matter was removed by filtration using celite. The filtrate was washed with water, dried over magnesium sulfate, and then concentrated. The residue was purified by silica gel column chromatography (n-hexane/benzene) to obtain 2.54 g of a white solid precursor (yield: 94.7%).

$^1$H-NMR (400 MHz, CDCl$_3$, δ): 7.53 (d, J=10.4 Hz, 4H), 7.45 to 7.43 (m, 4H), 1.37 (s, 18H)

[Chemical formula 211]

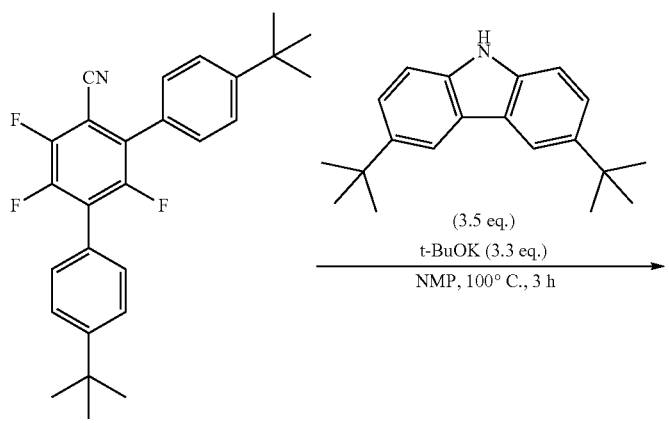

(3.5 eq.)
t-BuOK (3.3 eq.)
───────────→
NMP, 100° C., 3 h

-continued

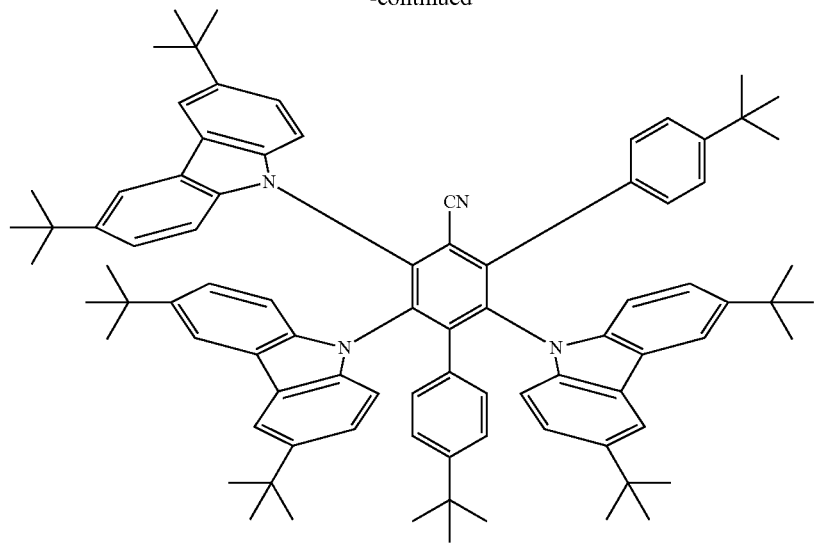

In a 200 mL three-neck flask that had been flushed with nitrogen, 3,6-di-t-butylcarbazole (1.16 g, 4.2 mmol) was dissolved in 24 mL of anhydrous N-methyl-2-pyrrolidone, potassium t-butoxide (0.44 g, 3.9 mmol) was then added, and the resulting mixture was stirred at room temperature for one hour. This mixture was then cooled in an ice bath, the precursor (0.50 g, 1.19 mmol) was added under a stream of nitrogen, and the resulting mixture was stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. The residue was purified by silica gel column chromatography (n-hexane/ethyl acetate) to obtain 0.76 g of a crudely purified product. Next, 1.44 g of the crudely purified product prepared using the same method was dissolved in ethyl acetate, and the solvent was removed by distillation to obtain 1.41 g of a light yellow-green-white solid of the target product (yield: 49.5%).

$^1$H-NMR (400 MHz, CDCl$_3$, δ): 7.80 (s, 2H), 7.54 (s, 2H), 7.38 (s, 2H), 7.26 (d, J=8.8 Hz, 2H), 7.15 (d, J=8.4 Hz, 2H), 6.99 (t, J=8.0 Hz, 4H), 6.91 (d, J=8.8 Hz, 4H), 6.85 (d, J=8.4 Hz, 2H), 6.76 (d, J=8.0 Hz, 2H), 6.59 (dd, J=10.4 Hz, 8.8 Hz, 4H), 6.38 (d, J=8.0 Hz, 2H), 1.37 (s, 18H), 1.34 (s, 18H), 1.27 (s, 18H), 1.09 (s, 9H), 0.73 (s, 9H)

[Evaluation of Light Emission]

Figure 19:
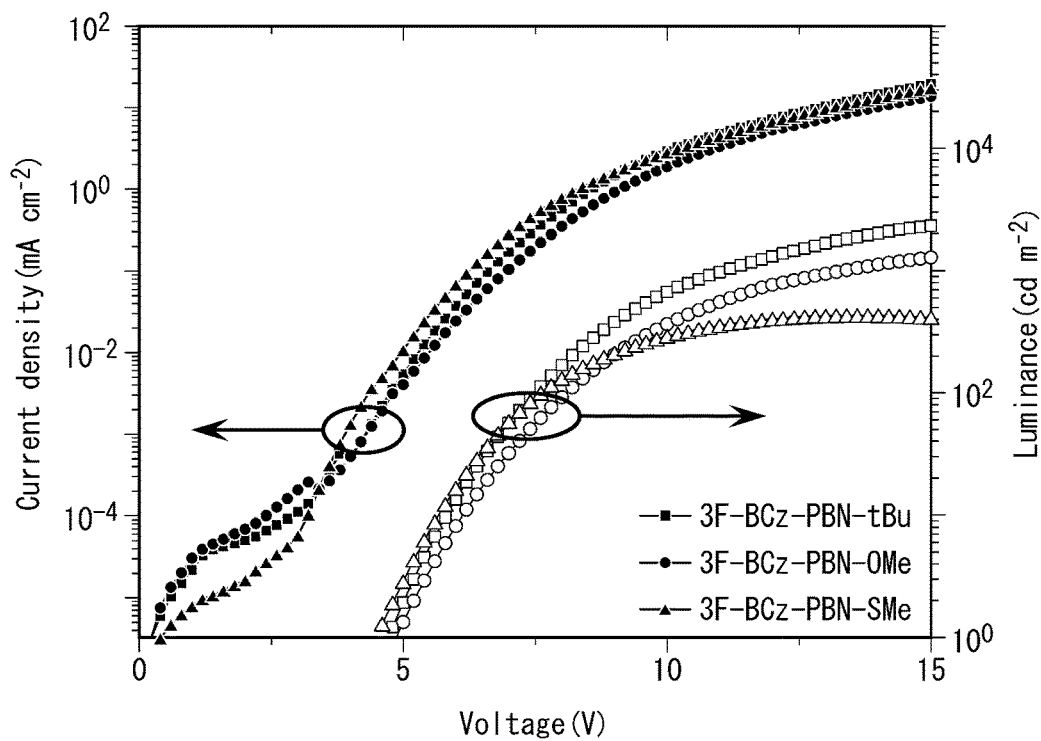
FIG. 19 is a diagram illustrating the voltage-current density-luminance characteristics for 3F-BCz-PBN-tBu, 3F-BCz-PBN-OMe and 3F-BCz-PBN-SMe.
Figure 20:
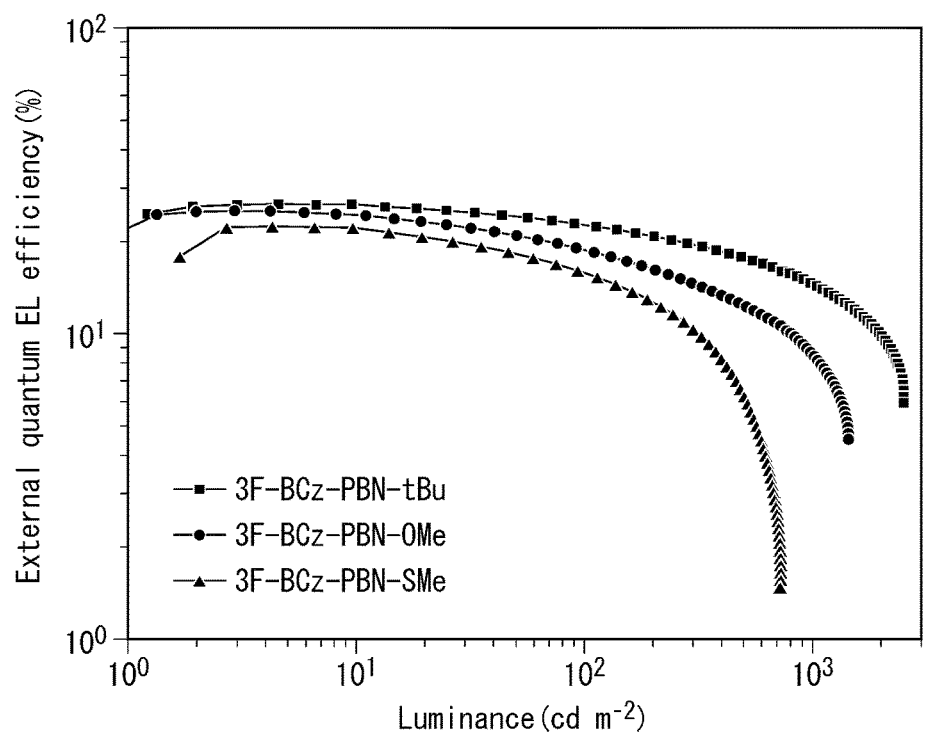
FIG. 20 is a diagram illustrating the luminance-external quantum efficiency characteristics for 3F-BCz-PBN-tBu, 3F-BCz-PBN-OMe and 3F-BCz-PBN-SMe.

With the exception of altering the dopant to 3F-BCz-PBN-tBu, a light emission evaluation was conducted using the same method as Example 1. The results are shown in FIGS. 19 and 20. EQEmax was 26.5%.

Example 31

Synthesis of 3F-BCz-PBN-OMe

[Chemical formula 212]

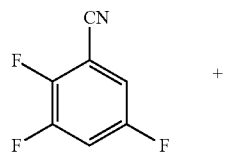
+
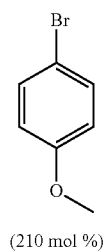
(210 mol %)

-continued
Pd(OAc)$_2$ (5 mol %)
PCy$_3$ (15 mol %)
ethylhexanoic acid (10 mol %)
K$_2$CO$_3$ (3 eq.)
———————→
Xylene
140° C., 22 h

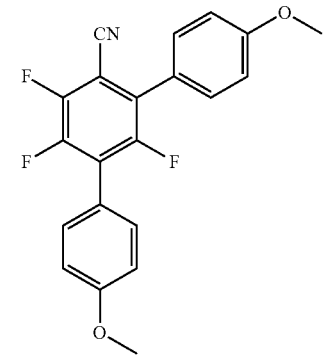

A 100 ml round-bottom flask was charged with 2,3,5-trifluorobenzonitrile (1.00 g, 6.4 mmol), 4-bromoanisole (2.50 g, 13.4 mmol), 2-ethylhexanoic acid (96.5 mg, 0.67 mmol), potassium carbonate (2.64 g, 19.1 mmol) and 20 ml of anhydrous xylene. The flask was degassed and flushed with nitrogen, tricyclohexylphosphine (1.6 ml of a 20% toluene solution, 0.95 mmol) and palladium acetate (72.3 mg, 0.32 mmol) were then added, and the resulting mixture was stirred at 140° C. for 22 hours. The reaction liquid was then returned to room temperature, ethyl acetate was added, and the insoluble matter was removed by filtration using celite. The filtrate was washed with water, dried over magnesium sulfate, and then concentrated. The residue was purified by silica gel column chromatography (n-hexane/benzene) to obtain 1.51 g of a white solid precursor (yield: 64.2%).

$^1$H-NMR (400 MHz, CDCl$_3$, δ): 7.46 to 7.42 (m, 4H), 7.05 to 7.02 (m, 4H), 3.87 (s, 6H)

129

[Chemical formula 213]

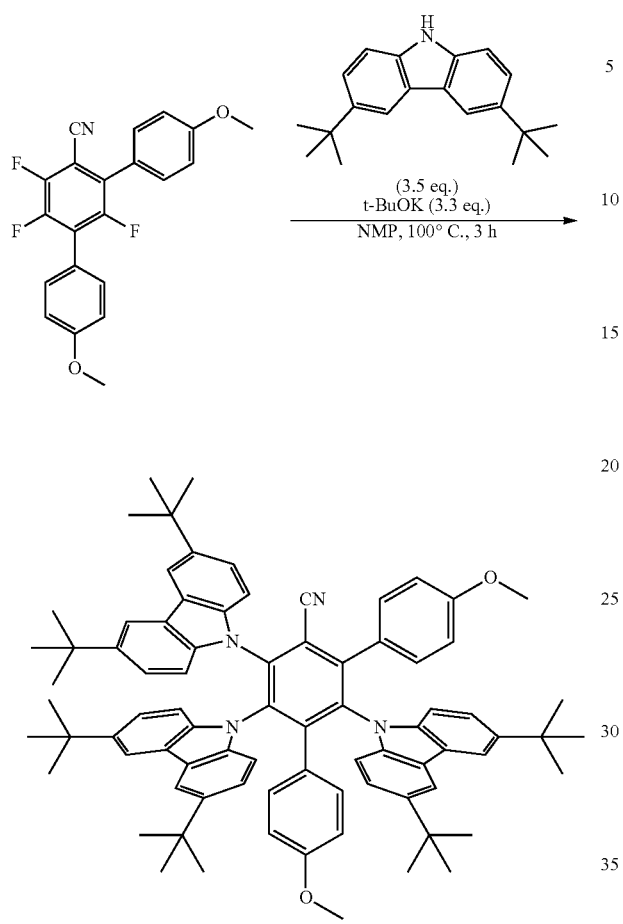

In a 200 mL three-neck flask that had been flushed with nitrogen, 3,6-di-t-butylcarbazole (1.51 g, 5.4 mmol) was dissolved in 25 mL of anhydrous N-methyl-2-pyrrolidone, potassium t-butoxide (0.58 g, 5.2 mmol) was then added, and the resulting mixture was stirred at room temperature for one hour. This mixture was then cooled in an ice bath, a solution containing the precursor (0.57 g, 1.54 mmol) dissolved in 6 mL of anhydrous N-methyl-2-pyrrolidone was added under a stream of nitrogen, and the resulting mixture was stirred at 100° C. for 3 hours. The reaction liquid was then cooled in an ice bath, cold water was added to the flask, and the precipitated solid was collected by filtration. This solid was dissolved in ethyl acetate, dried over magnesium sulfate, and then concentrated. The residue was purified by silica gel column chromatography (n-hexane/benzene) to obtain 0.80 g of a crudely purified product. Next, n-hexane/ethyl acetate was added to 2.07 g of the crudely purified product prepared using the same method, the mixture was subjected to ultrasonic irradiation, the precipitated crystals were collected by filtration, and the solvent was removed by distillation to obtain 1.82 g of the target product as a light yellow white solid (yield: 64.7%).

$^1$H-NMR (400 MHz, CDCl$_3$, δ): 7.85 (d, J=1.6 Hz, 2H), 7.53 (d, J=2.0 Hz, 2H), 7.38 (d, J=2.0 Hz, 2H), 7.31 (dd, J=8.8 Hz, 2.0 Hz, 2H), 7.19 (d, J=8.4 Hz, 2H), 7.01 (d, J=8.8 Hz, 2H), 6.90 (dd, J=8.0 Hz, 1.6 Hz, 2H), 6.81 to 6.77 (m, 4H), 6.64 to 6.55 (m, 6H), 5.94 (d, J=8.8 Hz, 2H), 3.62 (s, 3H), 3.25 (s, 3H), 1.39 (s, 18H), 1.34 (s, 18H), 1.28 (s, 18H)

130

[Evaluation of Light Emission]

With the exception of altering the dopant to 3F-BCz-PBN-OMe, a light emission evaluation was conducted using the same method as Example 1. The results are shown in FIGS. 19 and 20. EQEmax was 25.2%.

Example 32

Synthesis of 3F-BCz-PBN-SMe

[Chemical formula 214]

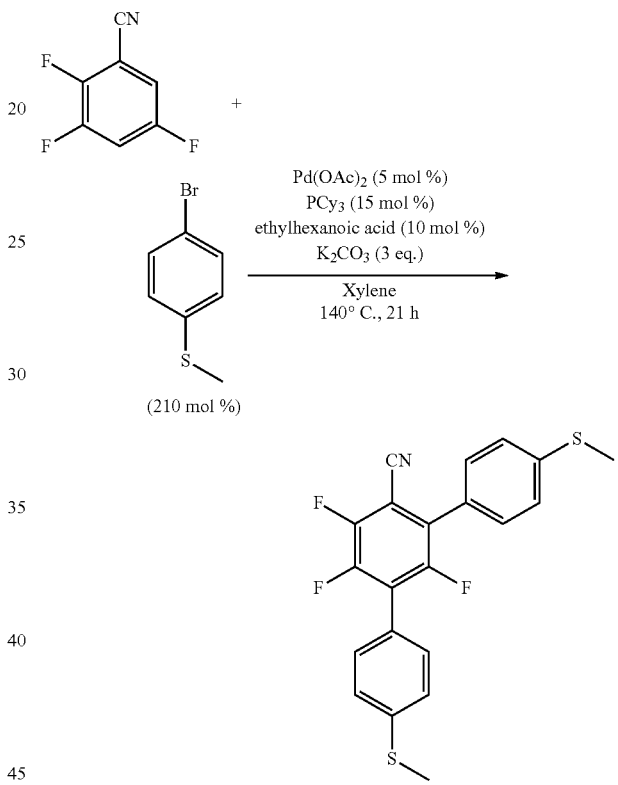

A 100 ml round-bottom flask was charged with 2,3,5-trifluorobenzonitrile (1.00 g, 6.4 mmol), 4-bromothioanisole (2.72 g, 13.4 mmol), 2-ethylhexanoic acid (95.0 mg, 0.66 mmol), potassium carbonate (2.65 g, 19.2 mmol) and 20 ml of anhydrous xylene. The flask was degassed and flushed with nitrogen, tricyclohexylphosphine (1.6 ml of a 20% toluene solution, 0.95 mmol) and palladium acetate (73.0 mg, 0.33 mmol) were then added, and the resulting mixture was stirred at 140° C. for 21 hours. The reaction liquid was then returned to room temperature, ethyl acetate was added, and the insoluble matter was removed by filtration using celite. The filtrate was washed with water, dried over magnesium sulfate, and then concentrated. The residue was purified by silica gel column chromatography (n-hexane/benzene) and then washed with n-hexane/ethyl acetate to obtain 2.05 g of a precursor in the form of a white solid (yield: 80.2%).

$^1$H-NMR (400 MHz, CDCl$_3$, δ): 7.42 to 7.34 (m, 8H), 2.54 (s, 6H)

[Chemical formula 215]

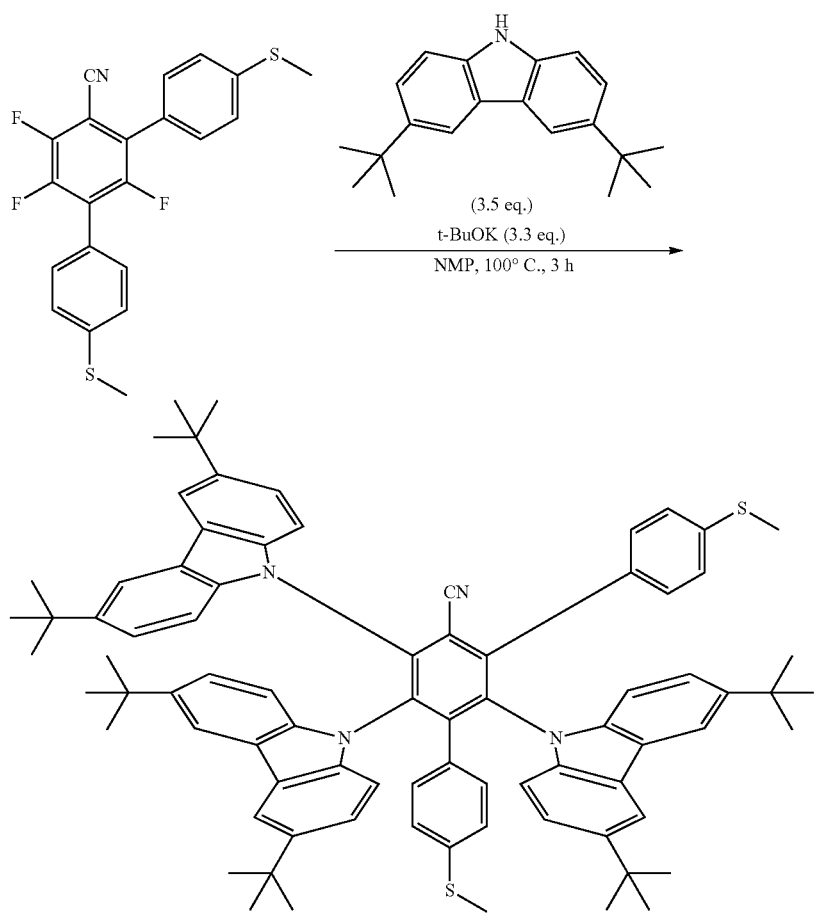

In a 200 mL three-neck flask that had been flushed with nitrogen, 3,6-di-t-butylcarbazole (1.95 g, 7.0 mmol) was dissolved in 32 mL of anhydrous N-methyl-2-pyrrolidone, potassium t-butoxide (0.76 g, 6.8 mmol) was then added, and the resulting mixture was stirred at room temperature for one hour. This mixture was then cooled in an ice bath, the precursor (0.80 g, 2.00 mmol) was added under a stream of nitrogen, and the resulting mixture was stirred at 100° C. for 3 hours. The reaction liquid was then cooled in an ice bath, cold water was added to the flask, and the precipitated solid was collected by filtration. This solid was dissolved in dichloromethane, dried over magnesium sulfate, and then concentrated. The residue was purified by silica gel column chromatography (n-hexane/dichloromethane) to obtain a crudely purified product. Subsequently, n-hexane/diethyl ether was added to the crudely purified product, the mixture was subjected to ultrasonic irradiation, the precipitated crystals were collected by filtration, and the solvent was removed by distillation to obtain 1.85 g of the target product as a light yellow solid (yield: 78.7%).

$^{1}$H-NMR (400 MHz, CDCl$_{3}$, δ): 7.85 (d, J=1.6 Hz, 2H), 7.53 (d, J=2.0 Hz, 2H), 7.38 (d, J=1.2 Hz, 2H), 7.31 (dd, J=8.8 Hz, 2.0 Hz, 2H), 7.18 (d, J=8.4 Hz, 2H), 6.99 (d, J=8.8 Hz, 2H), 6.92 to 6.89 (m, 4H), 6.80 to 6.77 (m, 4H), 6.60 (d, J=8.4 Hz, 2H), 6.57 (d, J=8.4 Hz, 2H), 6.29 (d, J=8.4 Hz, 2H), 2.30 (s, 3H), 1.95 (s, 3H), 1.39 (s, 18H), 1.34 (s, 18H), 1.28 (s, 18H)

[Evaluation of Light Emission]

With the exception of altering the dopant to 3F-BCz-PBN-SMe, a light emission evaluation was conducted using the same method as Example 1. The results are shown in FIGS. 19 and 20. EQEmax was 22.0%.

INDUSTRIAL APPLICABILITY

The present invention is able to provide a 2,3,4,5,6-pentasubstituted benzonitrile compound having excellent light emission characteristics, a light-emitting material, and a light-emitting element using the same.

The invention claimed is:

1. A compound represented by formula (IIa), formula (IIb), formula (IIc), formula (IIIa), or formula (IIIb):

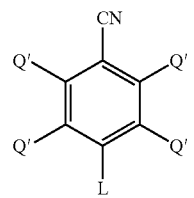

(IIa)

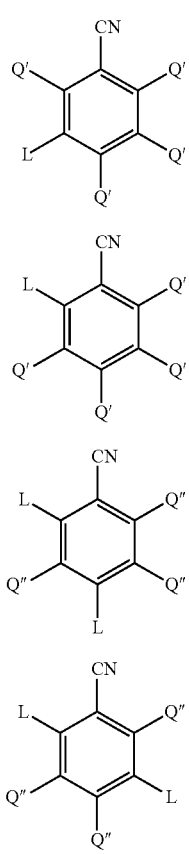

wherein in formula (IIa), formula (IIb), formula (IIc), formula (IIIa), and formula (IIIb):

each L independently represents a substituted or unsubstituted, nitrogen-containing 5-membered ring or 6-membered ring heteroaryl group, each Q' independently represents a substituted or unsubstituted 3,6-di-t-butyl-9H-carbazol-9-yl group, each Q" independently represents a substituted or unsubstituted 3,6-di-t-butyl-9H-carbazol-9-yl group, or a substituted or unsubstituted 3,6-diphenyl-9H-carbazol-9-yl group.

2. The compound according to claim 1, wherein L represents a substituted or unsubstituted pyridinyl group, a substituted or unsubstituted pyrimidinyl group, a substituted or unsubstituted oxazolyl group, a substituted or unsubstituted thiazolyl group, or a substituted or unsubstituted imidazolyl group.

3. The compound according to claim 1, wherein L represents a substituted or unsubstituted pyridinyl group, or a substituted or unsubstituted pyrimidinyl group.

4. A light-emitting material comprising the compound according to claim 1.

5. A light-emitting element comprising the light-emitting material according to claim 4.

* * * * *